United States Patent
Angell et al.

(10) Patent No.: US 7,425,555 B2
(45) Date of Patent: Sep. 16, 2008

(54) HETEROARYL SUBSTITUTED BIPHENYL DERIVATIVES AS P38 KINASE INHIBITORS

(75) Inventors: Richard Martyn Angell, London (GB); Paul Bamborough, Stevenage (GB); Ian Robert Baldwin, Stevenage (GB); Anne-Marie Li-Kwai-Cheung, Harlow (GB); Timothy Longstaff, Stevenage (GB); Suzanne Joy Merrick, Stevenage (GB); Kathryn Jane Smith, Stevenage (GB); Stephen Swanson, Stevenage (GB); Ann Louise Walker, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 489 days.

(21) Appl. No.: 10/513,095

(22) PCT Filed: Apr. 29, 2003

(86) PCT No.: PCT/GB03/01834

§ 371 (c)(1),
(2), (4) Date: Aug. 26, 2005

(87) PCT Pub. No.: WO03/093248

PCT Pub. Date: Nov. 13, 2003

(65) Prior Publication Data

US 2006/0089393 A1     Apr. 27, 2006

(30) Foreign Application Priority Data

Apr. 30, 2002 (GB) .................. 0209891.1

(51) Int. Cl.
*A61K 31/5377* (2006.01)
*C07D 413/12* (2006.01)

(52) U.S. Cl. .............. 514/236.2; 544/106; 544/111; 544/132; 544/133; 548/125; 548/143; 548/146; 548/190; 548/195; 514/231.2; 514/231.5; 514/364; 514/365; 514/371

(58) Field of Classification Search ............... 544/106, 544/111, 132, 133; 548/125, 143, 146, 190, 548/195; 514/231.2, 231.5, 235.5, 236.2, 514/361, 364, 365, 370, 371
See application file for complete search history.

(56) References Cited

U.S. PATENT DOCUMENTS

| | | | |
|---|---|---|---|
| 7,151,118 B2 * | 12/2006 | Angell et al. | 514/617 |
| 7,208,629 B2 * | 4/2007 | Angell et al. | 564/156 |
| 2004/0053942 A1 | 3/2004 | Alberti et al. | |

FOREIGN PATENT DOCUMENTS

| | | |
|---|---|---|
| WO | WO 03/032970 | 4/2003 |
| WO | WO 03/032971 | 4/2003 |
| WO | WO 03/032972 | 4/2003 |
| WO | WO 03/032980 | 4/2003 |
| WO | WO 03/032986 | 4/2003 |
| WO | WO 03/032987 | 4/2003 |
| WO | WO 03/033457 | 4/2003 |
| WO | WO 03/033482 | 4/2003 |
| WO | WO 03/033483 | 4/2003 |
| WO | WO 03/068747 | 8/2003 |
| WO | WO 03/093248 | 11/2003 |
| WO | WO 2004/010995 | 2/2004 |

* cited by examiner

*Primary Examiner*—Golam M Shameem
(74) *Attorney, Agent, or Firm*—Dara L. Dinner; Stephen Venetianer; Charles M. Kinzig

(57) ABSTRACT

Compounds of formula (I):

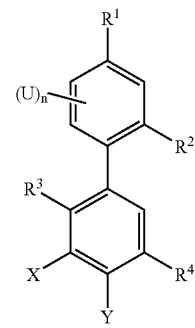

are inhibitors of p38 kinase and are useful in the treatment of conditions or disease states mediated by p38 kinase activity or mediated by cytokines produced by the activity of p38.

16 Claims, No Drawings

HETEROARYL SUBSTITUTED BIPHENYL DERIVATIVES AS P38 KINASE INHIBITORS

This application is a §371 national stage entry of PCT/GB03/01834, filed 29 Apr. 2003.

This invention relates to novel compounds and their use as pharmaceuticals, particularly as p38 kinase inhibitors, for the treatment of conditions or disease states mediated by p38 kinase activity or mediated by cytokines produced by the activity of p38 kinase.

We have now found a group of novel compounds that are inhibitors of p38 kinase.

According to the invention there is provided a compound of formula (I):

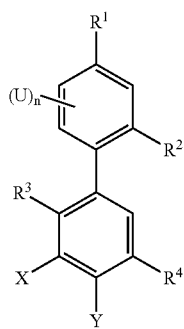

(I)

wherein $R^1$ is a 5- or 6-membered monocyclic heteroaryl ring containing up to 4 heteroatoms independently selected from oxygen, nitrogen and sulfur, which ring is optionally substituted by up to two substituents selected from $C_{1-6}$alkyl, —$(CH_2)_m$—$C_{3-7}$cycloalkyl, halogen, cyano, trifluoromethyl, imino, oxo, —$(CH_2)_m OR^5$, —$(CH_2)_m COR^5$, —$(CH_2)_m S(O)_t R^5$, —$(CH_2)_m NR^5 R^6$, —$(CH_2)_m CONR^5 R^6$, —$(CH_2)_m NHCOR^5$, —$(CH_2)_m SO_2 NR^5 R^6$, —$(CH_2)_m NHSO_2 R^5$, and a 5-membered heteroaryl ring optionally substituted by $C_{1-2}$alkyl;

$R^2$ is selected from hydrogen, methyl, chloro and fluoro;

$R^3$ is selected from methyl and chloro;

$R^4$ is selected from —NH—CO—$R^7$ and —CO—NH—$(CH_2)_q$—$R^8$;

$R^5$ is selected from hydrogen, $C_{1-6}$alkyl optionally substituted by up to two OH groups, —$(CH_2)_m$—$C_{3-7}$cycloalkyl, —$(CH_2)_m$phenyl optionally substituted by $R^{16}$ and —$(CH_2)_m$heteroaryl optionally substituted by $R^{16}$, $R^6$ is selected from hydrogen and $C_{1-6}$alkyl, or $R^5$ and $R^6$, together with the nitrogen atom to which they are bound, form a 5- or 6-membered heterocyclic ring optionally containing one additional heteroatom independently selected from oxygen, sulfur and N—$R^9$;

$R^7$ is selected from hydrogen, $C_{1-6}$alkyl, —$(CH_2)_q$—$C_{3-7}$cycloalkyl, trifluoromethyl, —$(CH_2)_r$heteroaryl optionally substituted by $R^{10}$ and/or $R^{11}$, and —$(CH_2)_r$phenyl optionally substituted by $R^{10}$ and/or $R^{11}$;

$R^8$ is selected from hydrogen, $C_{1-6}$alkyl, $C_{3-7}$cycloalkyl, $CONHR^{12}$, phenyl optionally substituted by $R^{10}$ and/or $R^{11}$, and heteroaryl optionally substituted by $R^{10}$ and/or $R^{11}$;

$R^9$ is selected from hydrogen and methyl;

$R^{10}$ is selected from $C_{1-6}$alkyl, $C_{1-6}$alkoxy, —$(CH_2)_q$—$C_{3-7}$cycloalkyl, —$CONR^{12}R^{13}$, —$NHCOR^{13}$, halogen, CN, —$(CH_2)_s NR^{14}R^{15}$, trifluoromethyl, phenyl optionally substituted by one or more $R^{11}$ groups, and heteroaryl optionally substituted by one or more $R^{11}$ groups;

$R^{11}$ is selected from $C_{1-6}$alkyl, $C_{1-6}$alkoxy, halogen, trifluoromethyl, and —$(CH_2)_s NR^{14}R^{15}$;

$R^{12}$ and $R^{13}$ are each independently selected from hydrogen and $C_{1-6}$alkyl, or $R^{12}$ and $R^{13}$, together with the nitrogen atom to which they are bound, form a 5- or 6-membered heterocyclic ring optionally containing one additional heteroatom independently selected from oxygen, sulfur and N—$R^9$, wherein the ring may be substituted by up to two $C_{1-6}$alkyl groups;

$R^{14}$ is selected from hydrogen, $C_{1-6}$alkyl and —$(CH_2)_q$—$C_{3-7}$cycloalkyl optionally substituted by $C_{1-6}$alkyl, $R^{15}$ is selected from hydrogen and $C_{1-6}$alkyl, or $R^{14}$ and $R^{15}$, together with the nitrogen atom to which they are bound, form a 5- or 6-membered heterocyclic ring optionally containing one additional heteroatom selected from oxygen, sulfur and N—$R^9$;

$R^{16}$ is selected from halogen, $C_{1-6}$alkyl, hydroxy, $C_{1-6}$alkoxy and trifluoromethyl;

U is selected from methyl and halogen;

X and Y are each selected independently from hydrogen, methyl and halogen;

m is selected from 0, 1, 2 and 3;

n is selected from 0, 1 and 2;

q is selected from 0, 1 and 2;

r is selected from 0 and 1;

s is selected from 0, 1, 2 and 3; and t is selected from 0, 1 and 2.

According to a further embodiment of the invention there is provided a compound of formula (IA):

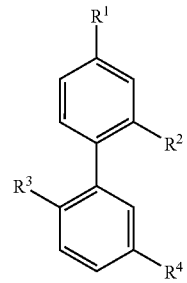

(IA)

wherein $R^1$, $R^2$, $R^3$ and $R^4$ are as defined above.

In one embodiment, $R^1$ is a 5- or 6-membered monocyclic heteroaryl ring containing up to 3 heteroatoms independently selected from oxygen, nitrogen and sulfur, which ring is optionally substituted by up to two substituents selected from $C_{1-6}$alkyl, —$(CH_2)_m$—$C_{3-7}$cycloalkyl, halogen, cyano, trifluoromethyl, —$(CH_2)_m OR^5$, —$(CH_2)_m NR^5 R^6$, —$(CH_2)_m CONR^5 R^6$, —$(CH_2)_m NHCOR^5$, —$(CH_2)_m SO_2 NR^5 R^6$, —$(CH_2)_m NHSO_2 R^5$, and a 5-membered heteroaryl ring optionally substituted by $C_{1-2}$alkyl.

Representative examples of $R^1$ include 5-membered monocyclic heteroaryl rings containing 2, 3 or 4 heteroatoms independently selected from oxygen, nitrogen and sulfur, in particular pyrrolyl, thiazolyl, pyrazolyl, imidazolyl, 1,2,4-oxadiazolyl, 1,3,4-oxadiazolyl, 1,3,4-triazolyl or tetrazolyl. Further representative examples of $R^1$ include 5-membered monocyclic heteroaryl rings containing up to 3 heteroatoms independently selected from oxygen, nitrogen and sulfur. In one embodiment, $R^1$ is a 5-membered monocyclic heteroaryl ring containing 2 or 3 heteroatoms independently selected from oxygen, nitrogen and sulfur, in particular thiazolyl, imidazolyl, 1,2,4oxadiazolyl or 1,3,4-oxadiazolyl. In another embodiment, $R^1$ is pyrrolyl, pyrazolyl, imidazolyl, 1,2,4-oxadiazolyl, 1,3,4-oxadiazolyl, 1,3,4-triazolyl or tetrazolyl.

The 5- or 6-membered monocyclic heteroaryl ring may be optionally substituted by up to two substituents, located on any position on the ring. In one embodiment, the 5- or 6-membered monocyclic heteroaryl ring is optionally substituted by one substituent, located on any position on the ring. Representative examples of the substituents include $C_{1-4}$alkyl, in particular methyl or ethyl; —$(CH_2)_m$—$C_{3-7}$cycloalkyl, in particular —$CH_2$-cyclopropyl; imino; —$(CH_2)_mOR^5$, in particular —$CH_2OH$, —$CH_2OC_{1-4}$alkyl such as —$CH_2OCH_3$ or —$CH_2OCH_2CH_3$, and —$CH_2O(CH_2)_m$—$C_{3-7}$cycloalkyl such as —$CH_2OCH_2$-cyclopropyl; —$(CH_2)_mCOR^5$, in particular —$COCH_3$; —$(CH_2)_mNR^5R^6$, in particular —$NH_2$, —$NHC_{1-4}$alkyl such as —$NHCH_3$, —$CH_2NH_2$, —$CH_2NHCH_3$, —$CH_2NHCH_2CH_3$, —$CH_2N(CH_3)_2$, —$CH_2N(CH_2CH_3)_2$, —$CH_2NHCH(CH_2OH)_2$, —$CH_2NH$—$(CH_2)_m$—$C_{3-7}$cycloalkyl such as —$CH_2NH$-cyclopropyl, —$CH_2NHCH_2$-cyclopropyl or —$CH_2NH$-cyclohexyl, or —$(CH_2)_mNR^5R^6$ wherein $R^5$ and $R^6$, together with the nitrogen atom to which they are bound, form a 5- or 6-membered heterocyclic ring optionally containing one additional heteroatom independently selected from oxygen, sulfur and N—$R^9$; —$(CH_2)_mNHCOR^5$, in particular —$CH_2NHCOR^5$ wherein $R^5$ is $C_{1-4}$alkyl optionally substituted by up to two OH groups such as ethyl, 2,2-dimethylpropyl or methyl substituted by OH, —$(CH_2)_m$—$C_{3-7}$cycloalkyl such as —$CH_2$-cyclopropyl, —$(CH_2)_m$phenyl optionally substituted by $R^{16}$ such as phenyl or —$CH_2$phenyl, and —$(CH_2)_m$heteroaryl optionally substituted by $R^{16}$ such as —$CH_2$isoxazole substituted by methyl; —$(CH_2)_mNHSO_2R^5$, in particular —$CH_2NHSO_2R^5$ wherein $R^5$ is $C_{1-4}$alkyl such as methyl or —$(CH_2)_m$phenyl optionally substituted by $R^{16}$ such as —$CH_2$phenyl; and a 5-membered heteroaryl ring optionally substituted by $C_{1-2}$alkyl, in particular pyrrole substituted by methyl. Further representative substituents for the 5- or 6-membered monocyclic heteroaryl ring include $C_{1-4}$alkyl, in particular methyl, and —$(CH_2)_mNR^5R^6$.

In a preferred embodiment, $R^1$ is 5-methyl-1,3,4-oxadiazol-3-yl or 5-methyl-1,2,4-oxadiazol-3-yl.

In one embodiment, $R^2$ is selected from hydrogen, methyl and chloro. Representative examples of $R^2$ include hydrogen and methyl. In particular, $R^2$ is hydrogen.

A representative example of $R^3$ is methyl.

In one embodiment, $R^5$ is selected from hydrogen and $C_{1-6}$alkyl optionally substituted by up to two OH groups.

Representative examples of $R^5$ include hydrogen; $C_{1-4}$alkyl optionally substituted by up to two OH groups, in particular methyl optionally substituted by OH, ethyl, 2,2-dimethylpropyl or 1,3-dihydroxyprop-2-yl; —$(CH_2)_m$—$C_{3-7}$cycloalkyl, in particular cyclopropyl, —$CH_2$-cyclopropyl or cyclohexyl; —$(CH_2)_m$phenyl optionally substituted by $R^{16}$, in particular phenyl or —$CH_2$phenyl; and —$(CH_2)_m$heteroaryl optionally substituted by $R^{16}$, in particular —$CH_2$isoxazole substituted by methyl. Further representative examples of $R^5$ include hydrogen, $C_{1-4}$alkyl, in particular methyl, and $C_{1-4}$alkyl substituted by up to two OH groups, in particular 1,3-dihydroxyprop-2-yl. Additional representative examples of $R^5$ include hydrogen; $C_{1-4}$alkyl optionally substituted by up to two OH groups, in particular methyl optionally substituted by OH, ethyl or 2,2-dimethylpropyl; —$(CH_2)_m$—$C_{3-7}$cycloalkyl, in particular cyclopropyl, —$CH_2$-cyclopropyl or cyclohexyl; —$(CH_2)_m$phenyl optionally substituted by $R^{16}$, in particular phenyl or —$CH_2$phenyl; and —$(CH_2)_m$heteroaryl optionally substituted by $R^{16}$, in particular —$CH_2$isoxazole substituted by methyl.

Representative examples of $R^6$ include hydrogen and $C_{1-4}$alkyl, in particular methyl or ethyl. Further representative examples of $R^6$ include hydrogen and $C_{1-4}$alkyl, in particular methyl. An additional representative example of $R^6$ is ethyl.

In one embodiment, $R^5$ and $R^6$, together with the nitrogen atom to which they are bound, form a 5- or 6-membered heterocyclic ring optionally further containing one additional oxygen or sulphur atom, in particular pyrrolidinyl, piperidinyl, morpholino or thiomorpholino. In another embodiment, $R^5$ and $R^6$, together with the nitrogen atom to which they are bound, form a 5- or 6-membered heterocyclic ring optionally further containing one additional oxygen atom, in particular pyrrolidinyl, piperidinyl or morpholino. In a further embodiment, $R^5$ and $R^6$, together with the nitrogen atom to which they are bound, form a 5- or 6-membered heterocyclic ring optionally further containing one additional sulphur atom, in particular thiomorpholino.

In one embodiment, $R^7$ is selected from hydrogen, $C_{1-6}$alkyl, —$(CH_2)_q$—$C_{3-7}$cycloalkyl, trifluoromethyl, —$(CH_2)_r$heteroaryl optionally substituted by $R^{10}$ and/or $R^{11}$, and —$CH_2$phenyl optionally substituted by $R^{10}$ and/or $R^{11}$. Representative examples of $R^7$ include —$(CH_2)_r$heteroaryl optionally substituted by $R^{10}$ and/or $R^{11}$, in particular a 5- or 6-membered heteroaryl containing at least one heteroatom selected from oxygen, nitrogen and sulfur, for example, pyridinyl optionally substituted by —$(CH_2)_sNR^{14}R^{15}$, furyl or thiophenyl.

In one embodiment, $R^8$ is selected from hydrogen, $C_{1-6}$alkyl, $C_{3-7}$cycloalkyl, $CONHR^{12}$, heteroaryl optionally substituted by $R^{10}$ and/or $R^{11}$ and, when q is 1 or 2, phenyl optionally substituted by $R^{10}$ and/or $R^{11}$. In another embodiment, $R^8$ is selected from $C_{3-7}$cycloalkyl, phenyl optionally substituted by $R^{10}$ and/or $R^{11}$, and heteroaryl optionally substituted by $R^{10}$ and/or $R^{11}$. In a further embodiment, $R^8$ is selected from $C_{3-7}$cycloalkyl, and heteroaryl optionally substituted by $R^{10}$ and/or $R^{11}$. Representative examples of $R^8$ include $C_{3-6}$cycloalkyl such as cyclopropyl, cyclobutyl, cyclopentyl or cyclohexyl, in particular cyclopropyl; phenyl optionally substituted by $C_{1-4}$alkoxy, in particular methoxy, or —$(CH_2)_sNR^{14}R^{15}$; and heteroaryl optionally substituted by $R^{10}$ and/or $R^{11}$, in particular a 5- or 6-membered heteroaryl containing at least one heteroatom selected from oxygen, nitrogen and sulfur, for example, thiazolyl or thiadiazolyl.

Representative examples of $R^{10}$ and $R^{11}$ include $C_{1-4}$alkoxy, in particular methoxy, and —$(CH_2)_sNR^{14}R^{15}$.

In one embodiment $R^{14}$ and $R^{15}$, together with the nitrogen atom to which they are bound, form a 5- or 6-membered heterocyclic ring optionally further containing one additional oxygen atom, in particular pyrrolidinyl or morpholino.

In one embodiment, $R^{16}$ is selected from halogen, in particular fluorine, and $C_{1-6}$alkyl. A representative example of $R^{16}$ is $C_{1-4}$alkyl, in particular methyl.

In a preferred embodiment, X and Y are each independently selected from hydrogen, chlorine and fluorine. In a further preferred embodiment, X is fluorine. In another preferred embodiment, Y is hydrogen.

In one embodiment, n is 0.

In one embodiment, m is selected from 0, 1 and 2, in particular 0 and 1.

Representative examples of q are 0 and 1.

A representative example of r is 0.

A representative example of s is 0.

In one embodiment, t is selected from 1 and 2.

It is to be understood that the present invention covers all combinations of particular and preferred groups described hereinabove.

Particular compounds according to the invention include those mentioned in the Examples.

Preferred compounds of the invention include:
N-Cyclopropyl-2',6-dimethyl-4'-(5-methyl-1,3,4-oxadiazol-2-yl)[1,1'-biphenyl]-3-carboxamide;
6,2'-Dimethyl-4'-(5-methyl-[1,3,4]oxadiazol-2-yl)biphenyl-3-carboxylic acid cyclopropylmethyl-amide;
6,2'-Dimethyl-4'-(5-methyl-[1,3,4]oxadiazol-2-yl)-biphenyl-3-carboxylic acid thiazol-2-ylamide;
6-Methyl-4'-(5-methyl-[1,3,4]oxadiazol-2-yl)-biphenyl-3-carboxylic acid [1,3,4]thiadiazol-2-ylamide;
Furan-3-carboxylic acid[6-methyl-4'-(5-methyl-[1,3,4]oxadiazol-2-yl)-biphenyl-3-yl]-amide;
6-Methyl-4'-(5-methyl-[1,3,4]oxadiazol-2-yl)-biphenyl-3-carboxylic acid (3-morpholin-4-yl-phenyl)-amide; and
6-Methyl-4'-(5-methyl-[1,3,4]oxadiazol-2-yl)-biphenyl-3-carboxylic acid cyclopropylamide.

Further preferred compounds which may be mentioned include:
4'-(5-Amino-1,3,4-oxadiazol-2-yl)-N-cyclopropyl-5-fluoro-6-methyl-1,1'-biphenyl-3-carboxamide;
N-Cyclopropyl-5-fluoro-4'-[5-(methoxymethyl)-1,3,4-oxadiazol-2-yl]-6-methyl-1,1'-biphenyl-3-carboxamide;
N-Cyclopropyl-4'-{5-[(cyclopropylamino)methyl]-1,3,4-oxadiazol-2-yl}-5-fluoro-6-methyl-1,1'-biphenyl-3-carboxamide;
4'-[5-(Aminomethyl)-1,3,4-oxadiazol-2-yl]-N-cyclopropyl-5-fluoro-6-methyl-1,1'-biphenyl-3-carboxamide;
N-Cyclopropyl-6-methyl-4'-[5-(methylamino)-1,3,4-oxadiazol-2-yl]-1,1'-biphenyl-3-carboxamide;
N-Cyclopropyl-6-methyl-4'-[5-(1-methyl-1H-pyrrol-2-yl)-1,3,4-oxadiazol-2-yl]-1,1'-biphenyl-3-carboxamide;
N-Cyclopropyl-4'-(5-ethyl-1,3,4-oxadiazol-2-yl)-6-methyl-1,1'-biphenyl-3-carboxamide;
N-Cyclopropyl-6-methyl-4'-(1,3,4-oxadiazol-2-yl)-1,1'-biphenyl-3-carboxamide;
N-Cyclopropyl-5-fluoro-6-methyl-4'-(5-methyl-1,3,4-oxadiazol-2-yl)-1,1'-biphenyl-3-carboxamide;
N-Cyclopropyl-6-methyl-4'-[5-({[(3-methylisoxazol-5-yl)acetyl]amino}methyl)-1,3,4-oxadiazol-2-yl]-1,1'-biphenyl-3-carboxamide;
N-Cyclopropyl-4'-{5-[(diethylamino)methyl]-1,3,4-oxadiazol-2-yl}-6-methyl-1,1'-biphenyl-3-carboxamide;
N-Cyclopropyl-4'-{5-[(cyclopropylamino)methyl]-1,3,4-oxadiazol-2-yl}-6-methyl-1,1'-biphenyl-3-carboxamide;
N-Cyclopropyl-6-methyl-4'-[5-(thiomorpholin-4-ylmethyl)-1,3,4-oxadiazol-2-yl]-1,1'-biphenyl-3-carboxamide;
N-Cyclopropyl-4'-(5-{[(3,3-dimethylbutanoyl)amino]methyl}-1,3,4-oxadiazol-2-yl)-6-methyl-1,1'-biphenyl-3-carboxamide;
4'-(5-{[(Benzylsulfonyl)amino]methyl}-1,3,4-oxadiazol-2-yl)-N-cyclopropyl-6-methyl-1,1'-biphenyl-3-carboxamide;
N-Cyclopropyl-4'-{5-[(ethylamino)methyl]-1,3,4-oxadiazol-2-yl}-6-methyl-1,1'-biphenyl-3-carboxamide;
N-Cyclopropyl-6-methyl-4'-(5-{[(methylsulfonyl)amino]methyl}-1,3,4-oxadiazol-2-yl)-1,1'-biphenyl-3-carboxamide;
N-Cyclopropyl-4'-(5-{[(cyclopropylacetyl)amino]methyl}-1,3,4-oxadiazol-2-yl)-6-methyl-1,1'-biphenyl-3-carboxamide;
N-Cyclopropyl-6-methyl-4'-(5-{[(phenylacetyl)amino]methyl}-1,3,4-oxadiazol-2-yl)-1,1'-biphenyl-3-carboxamide;
N-Cyclopropyl-4'-[5-(hydroxymethyl)-1,3,4-oxadiazol-2-yl]-6-methyl-1,1'-biphenyl-3-carboxamide;
N-Cyclopropyl-4'-(5-{[(cyclopropylmethyl)amino]methyl}-1,3,4-oxadiazol-2-yl)-6-methyl-1,1'-biphenyl-3-carboxamide;
4'-(5-Amino-1,3,4-oxadiazol-2-yl)-N-cyclopropyl-6-methyl-1,1'-biphenyl-3-carboxamide;
N-Cyclopropyl-4'-[5-(ethoxymethyl)-1,3,4-oxadiazol-2-yl]-6-methyl-1,1'-biphenyl-3-carboxamide;
N-Cyclopropyl-4'-[5-(cyclopropylmethyl)-1,3,4-oxadiazol-2-yl]-6-methyl-1,1'-biphenyl-3-carboxamide;
N-Cyclopropyl-4'-[5-(methoxymethyl)-1,3,4-oxadiazol-2-yl]-6-methyl-1,1'-biphenyl-3-carboxamide;
N-Cyclopropyl-4'-{5-[(cyclopropylmethoxy)methyl]-1,3,4-oxadiazol-2-yl}-6-methyl-1,1'-biphenyl-3-carboxamide; and
N-Cyclopropyl-5-fluoro-6-methyl-4'-(tetrazol-5-yl)-1,1'-biphenyl-3-carboxamide.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A $C_{1-4}$alkyl group is preferred, for example methyl, ethyl, isopropyl or t-butyl. The said alkyl groups may be optionally substituted with one or more fluorine atoms for example, trifluoromethyl.

As used herein, the term "alkoxy" refers to a straight or branched chain alkoxy group, for example, methoxy, ethoxy, propoxy, prop-2-oxy, butoxy, but-2-oxy, 2-methylprop-1-oxy, 2-methylprop-2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$cycloalkyl group is preferred, for example, cyclopropyl, cyclopentyl or cyclohexyl.

As used herein, the terms "heteroaryl ring" and "heteroaryl" refer to a monocyclic 5- to 7-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the terms "heterocyclic ring" or "heterocyclyl" refer to a monocyclic 3- to 7-membered saturated hydrocarbon ring containing at least one heteroatom independently selected from oxygen, nitrogen and sulfur. Preferably, the heterocyclyl ring has five or six ring atoms. Examples of heterocyclyl groups include, but are not limited to, pyrrolidinyl, imidazolidinyl, pyrazolidinyl, piperidinyl, piperazinyl, morpholino, tetrahydropyranyl, tetrahydrofuranyl, and thiomorpholino. The said ring may be optionally substituted by one or more substituents independently selected from $C_{1-6}$alkyl and oxy.

As used herein, the terms "halogen" or "halo" refer to the elements fluorine, chlorine, bromine and iodine. Preferred halogens are fluorine, chlorine and bromine. A particularly preferred halogen is fluorine or chlorine.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid Preferably the solvent used is a pharmaceutically acceptable solvent. Examples of suitable pharmaceutically acceptable solvents include water, ethanol and acetic acid. All such solvates are included within the scope of the present invention.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Salts of the compounds of the present invention are also encompassed within the scope of the invention and may, for example, comprise acid addition salts resulting from reaction of an acid with a basic nitrogen atom present in a compound of formula (1).

Salts encompassed within the term "pharmaceutically acceptable salts" refer to non-toxic salts of the compounds of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

A compound of formula (I) may be prepared by reacting a compound of formula (II)

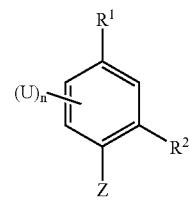

(II)

in which $R^1$, $R^2$, U and n are as hereinbefore defined and Z is halogen, in particular bromine or iodine, with a compound of formula (III)

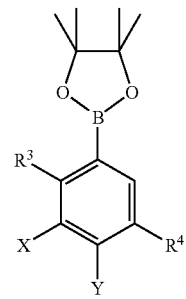

(III)

in which $R^3$, $R^4$, X and Y are as hereinbefore defined, in the presence of a catalyst, for example tetrakis(triphenylphosphine)palladium.

A compound of formula (III) may be prepared by, for example, reacting a compound of formula (IV)

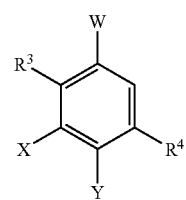

(IV)

in which $R^3$, $R^4$, X and Y are as hereinbefore defined and W is halogen, in particular bromine or iodine, with bis(pinnacolato)diboron, [1,1'-bis(diphenylphosphino)ferrocene]dichloropalladium (II) complex ($PdCl_2(ppdf)$) and potassium acetate in a solvent such as DMF.

When $R^4$ is —NH—CO—$R^7$, a compound of formula (IV) maybe prepared by reacting an amine of formula (V)

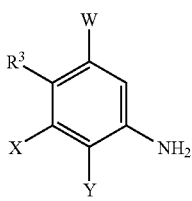

in which R³, X, Y and W are as hereinbefore defined, with an acid compound of formula (VI)

in which R⁷ is as hereinbefore defined, under amide forming conditions.

Suitable amide forming conditions are well known in the art and include adding a base such as DIPEA to a mixture of the amine of formula (V), the acid of formula (VI), and HATU in a solvent such as DMF.

Alternatively, when R⁴ is —CO—NH—$(CH_2)_q$—R⁸ a compound of formula (IV) may readily be prepared from a corresponding acid compound of formula (VII)

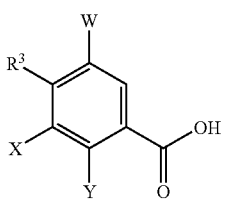

in which R³, X, Y and W are as hereinbefore defined, by converting the acid to an activated form of the acid, for example the acid chloride, by treatment with, for example, thionyl chloride, and then reacting the activated acid thus formed with an amine compound of formula (VIII)

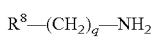

in which R⁸ is as hereinbefore defined, under amide forming conditions.

Suitable amide forming conditions are well known in the art and include treating a solution of the acid of formula (VII), or the activated form thereof, in for example DMF, with an amine of formula (VIII) in the presence of a base such as triethylamine.

It will be appreciated that in the preparation methods described above, R¹, R², R³, R⁴, U, X and Y may be R¹, R², R³, R⁴, U, X and Y as hereinbefore defined or groups convertible to R¹, R², R³, R⁴, U, X and Y. Conversion of a R¹, R², R³, R⁴, U, X or Y group may arise if, for example, a protecting group is needed during the reactions described above. A comprehensive discussion of the ways in which such groups may be protected and methods for cleaving the resulting protected derivatives is given by for example T. W. Greene and P. G. M. Wuts in Protective Groups in Organic Synthesis 2$^{nd}$ ed., John Wiley & Son, Inc 1991 and by P. J. Kocienski in Protecting Groups, Georg Thieme Verlag 1994.

Additionally, a further general method comprises final stage modification of one compound of formula (I) into another compound of formula (I). Suitable functional group transformations for converting one compound of formula (I) into another compound of formula (I) are well known in the art and are described in, for instance, *Comprehensive Organic Functional Group Transformations*, eds. A. R Katritzky, O. Meth-Cohn and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989).

For example, one general method for preparing the compounds of formula (I) comprises the reactions set out in Scheme 1 below.

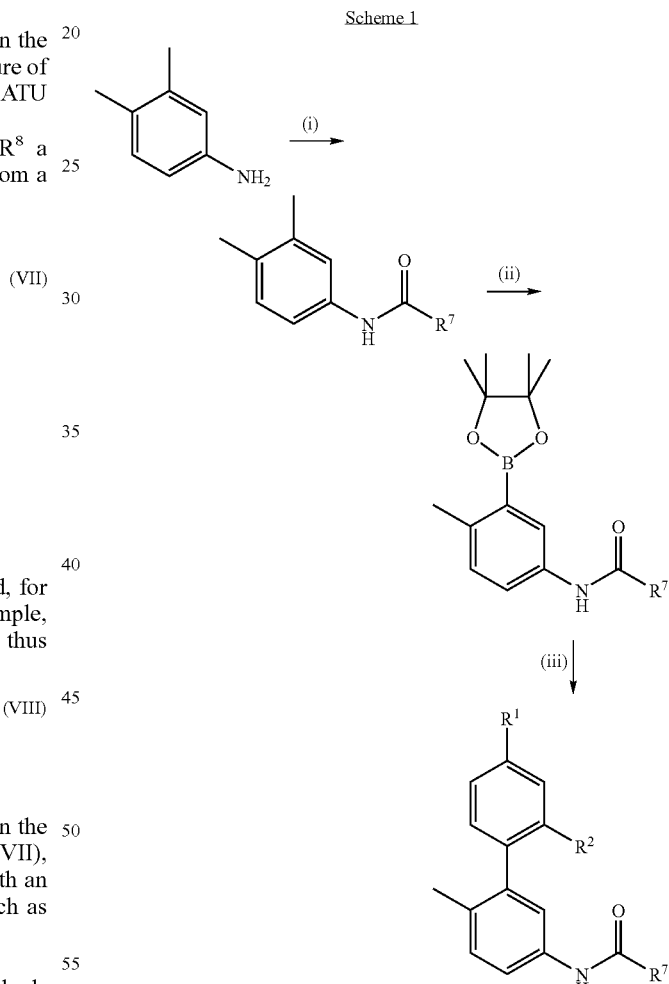

(i) HATU, R⁷CO₂H, DIPEA, DMF.

(ii) Bis(pinacolato)diboron, KOAc, PdCl₂(ppdf), DMF, 80° C.

(iii) R¹R²C₆H₃-Br/I, Pd(PPh₃)₄, 10% aq Na₂CO₃, DME, 80° C.

For example, a further general method for preparing the compounds of formula (I) comprises the reactions set out in Scheme 2 below.

Scheme 2

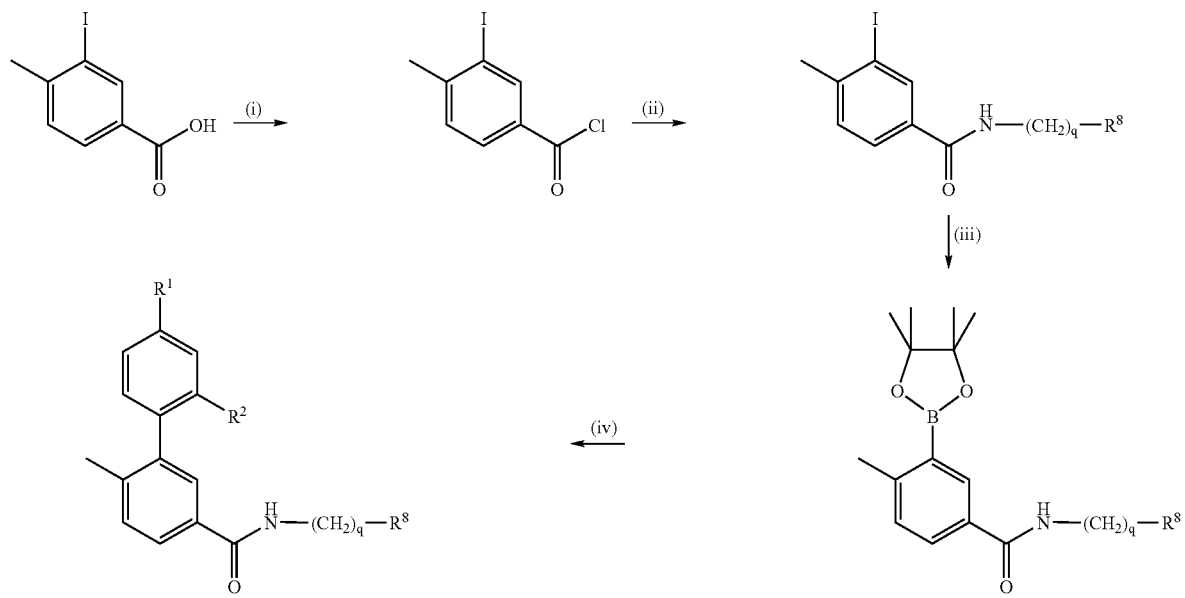

(i) SOCl$_2$, CHCl$_3$, 80 °C.
(ii) R$^8$—(CH$_2$)$_q$—NH$_2$, Et$_3$N, DMF, 80° C.
(iii) Bis(pinacolato)diboron, KOAc, PdCl$_2$(ppdf), DMF, 80° C.
(iv) R$^1$R$^2$C$_6$H$_3$—Br/I, Pd(PPh$_3$)$_4$, 10% aq Na$_2$CO$_3$, DME, 80° C.

Whilst it is possible for the compounds of the present invention to be administered as the new chemical, the compounds of formula (I) are conveniently administered in the form of pharmaceutical compositions. Thus, in another aspect of the invention, we provide a pharmaceutical composition comprising a compound of formula (I), in admixture with one or more pharmaceutically acceptable carriers, diluents or excipients.

The compounds of formula (I) may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I). A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymnethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0. 1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention.

For conditions or disease states as are treated by the present invention, maintaining consistent daily levels in a subject over an extended period of time, e.g., in a maintenance regime, can be particularly beneficial.

In another aspect, the present invention provides a compound of formula (I) for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I). The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I).

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I).

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I).

A further aspect of the invention provides a method of treatment of a human or animal subject suffering from rheumatoid arthritis, asthma, chronic pulmonary inflammation, chronic obstructive pulmonary disease, neurodegenerative disease, Alzheimer's disease, Parkinson's disease and epilepsy which comprises administering to said subject a therapeutically effective amount of a compound of formula (I).

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable salt or solvate thereof.

The compounds of formula (I) may be employed alone or in combination with other therapeutic agents for the treatment of the above-mentioned conditions. In particular, in rheumatoid arthritis therapy, combination with other chemotherapeutic or antibody agents is envisaged. Combination therapies according to the present invention thus comprise the administration of at least one compound of formula (I) and at least one other pharmaceutically active agent. The compound(s) of formula (I) and the other pharmaceutically active agent(s) may be administered together or separately and, when administered separately, this may occur separately or sequentially in any order. The amounts of the compound(s) of formula (I) and the other pharmaceutically active agent(s) and the relative timings of administration will be selected in order to achieve the desired combined therapeutic effect. Examples of other pharmaceutically active agents which may be employed in combination with compounds of formula (I) for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying antirheumatic drugs (DMARDs) such as methotrexate, sulphasalazine, cyclosporin A, hydroxychoroquine, auranofin, aurothioglucose, gold sodium thiomalate and penicillamine.

EXAMPLES

The following Examples are illustrative embodiments of the invention, not limiting the scope of the invention in any way. Reagents are commercially available or are prepared according to procedures in the literature.

LCMS was conducted on a column (3.3 cm×4.6 mm ID, 3 um ABZ+PLUS), at a Flow Rate of 3 ml/min, Injection Volume of 5 μl, at room temperature and UV Detection Range at 215 to 330 nm.

4-(4-Bromophenyl)-2-thiazolamine monohydrobromide and 3-iodo-4-methylaniline were purchased from Lancaster.

2-(4-Bromophenyl)-1H-imidazole and 5-(4iodophenyl)-1H-tetrazole were purchased from Peakdale Fine Chemicals.

2-Chloroisonicotinic acid was purchased from Maybridge Chemicals.

3-(4-Bromo-3-methylphenyl)-5-methyl-1,2,4-oxadiazole was prepared by the procedure described in EP 0 533 268 (Intermediate 1).

2-(4-Bromo-3-methylphenyl)-5-methyl-1,3,4-oxadiazole was prepared by the procedure described in EP 0 533 268 (Intermediate 10).

3-(4-Bromophenyl)-5-methyl-1,2,4-oxadiazole was prepared by the procedure described in WO 97/43262 (Description 11).

Intermediate 1: 3-Iodo-4methylbenzoyl chloride

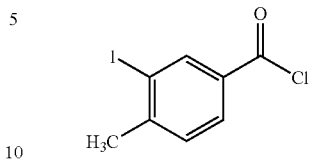

Thionyl chloride (8.2 ml, 112.5 mmol) was added to a mixture of 3-iodo-4-methylbenzoic acid (18.5 g, 75 mmol) in chloroform (100 ml) and heated at 61° C. for 16 hours. The solvent was removed in vacuo and excess thionyl chloride removed by azeotroping with toluene (3×30 ml). The desired product was formed as a beige solid (19.5 g 93%) and used in subsequent reactions without further purification.

NMR: δH [$^2$H$_6$]—DMSO 8.31 (1H, d), 7.87 (1H, dd), 7.46 (1H, d), 2.43 (3H, s) ppm.

Intermediate 2: 4-(3-Nitrophenyl)morpholine

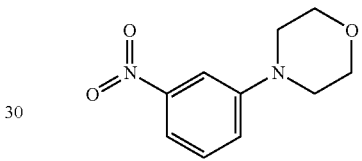

3-Fluoronitrobenzene (10 g, 71 mmol) was added to a solution of morpholine (34 ml, 390 mmol) in dimethylsulfoxide (120 ml) and heated at 110° C. for 60 hours. The reaction was cooled and poured onto water (800 ml). The desired product precipitated and was collected by filtration. The orange solid was dried in vacuo and used in subsequent reactions without further purification (13.7 g, 66 mmol).

NMR: δH [$^2$H$_6$]—DMSO 7.68 (1H, dd), 7.62 (1H, dd), 7.49 (1H, t), 7.42 (1H, dd), 3.76 (4H, dd), 3.24 (4H, dd) ppm.

Intermediate 3: 3-(4Morpholinyl)benzenamine

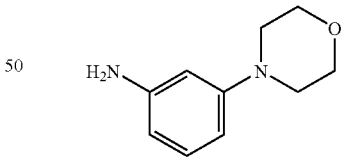

A flask containing 5% palladium on carbon (1.95 g) was evacuated and refilled with hydrogen. 4-(3-Nitrophenyl)morpholine (intermediate 2) (19.5 g, 93.75 mmol) was introduced into the flask as a solution in ethanol and dimethylformamide (1000 ml, 4:1 v/v). The reaction was stirred at room temperature until further uptake of hydrogen ceased (after approximately 7 L). The reaction was then filtered through celite and solvent removed in vacuo to yield the desired product (12.6 g, 70.6 mmol) as a beige solid.

NMR: δH [$^2$H$_6$]—DMSO 6.85 (1H, t), 6.12 (2H, m), 6.06 (1H, dd), 4.88 (2H, brs), 3.70 (4H, apparent t), 2.98 (4H, apparent t) ppm. LCMS: retention time 1.08 min MH$^+$179.

Intermediate 4: 3-Iodo-4-methyl-N-[3-(4-morpholinyl)phenyl]benzamide

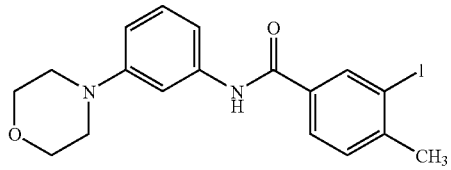

3-Iodo4-methylbenzoyl chloride (Intermediate 1) (19.5 g, 69.6 mmol) was added portion-wise to a mixture of triethylamine (48 ml, 350 mmol) and 3-(4-morpholinyl)benzenamine (Intermediate 3) (12.6 g, 70.6 mmol) in dimethyl formamide (150 ml) and the mixture was heated at 80° C. for 16 hours. The solvent was removed in vacuo and the residue taken up in chloroform (200 ml). The organic layer was washed with water (2×100 ml), 2M sodium hydroxide solution (100 ml) and brine (100 ml), dried over magnesium sulfate, filtered and solvent removed in vacuo. The resulting yellow solid was titurated with diethyl ether and collected by filtration to yield the desired product as an off-white solid (20.0 g, 47.0 mmol). The product was used in subsequent reactions without further purification.

NMR: δH [$^2$H$_6$]—DMSO 10.10 (1H,s), 8.39 (1H, d), 7.90 (1H, dd), 7.49 (1H, d), 7.38 (1H, t), 7.28 (1H, brd), 7.19 (1H, t), 6.71 (1H, dd), 3.75 (4H, apparent t), 3.10 (4H, apparent t), 2.44 (3H, s) ppm. LCMS: retention time 3.52 min MH$^+$423.

Intermediate 5: 4-Methyl-N-[3-(4-morpholinyl)phenyl]-3-(4,4,5,5-tetramethyl-[1,3,2]-dioxaborolan-2-yl)benzamide

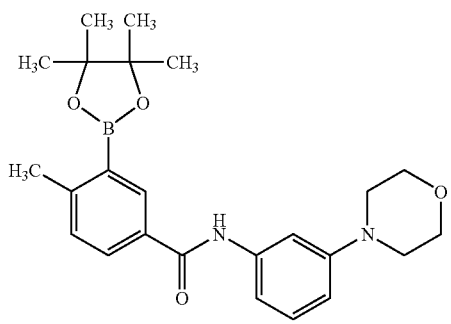

3-Iodomethyl-N-[3-(4-morpholinyl)phenyl]benzamide (Intermediate 4) (8.00 g, 18.9 mmol), triethylamine (7.9 ml, 56.7 mmol) and bis(pinacolato)diboron (4.13 ml, 28.4 mmol) were added to a solution of [1,1'-bis(diphenylphosphino)ferrocene]dichloropalladium (II) complex with dichloromethane (1:1) (770 mg, 945 mmol) in dioxane (100 ml) and the mixture was heated under nitrogen at 80° C. for 3 hours. The reaction was cooled and the solvent removed in vacuo and the residue taken up in dichloromethane (50 ml). The organic solution was washed with water (100 ml×3), brine (100 ml), dried over magnesium sulfate, filtered and solvent removed in vacuo. The residue was purified by column chromatography (30% ethyl acetate/cyclohexane v:v to 50% ethyl acetate/cyclohexane v:v). The desired product was yielded as a white solid (4.05 g, 9.45 mmol).

NMR: δH [$^2$H$_6$]—DMSO 10.11 (1H,s), 8.19 (1H, d), 7.93 (1H, dd), 7.40 (1H, brs), 7.33 (1H, d), 7.28 (1H, brd), 7.19 (1H, t), 6.70 (1H, dd), 3.75 (4H, apparent t), 3.09 (4H, apparent t), 2.54 (3H, s), 1.33 (12H, s) ppm. LCMS: retention time 3.65 min MH$^+$423.

Intermediate 6: N-(3-Methoxy-phenyl)-4-methyl-3-(4,4,5,5-tetramethyl-[1,3,2]dioxaborolan-2-yl)-benzamide

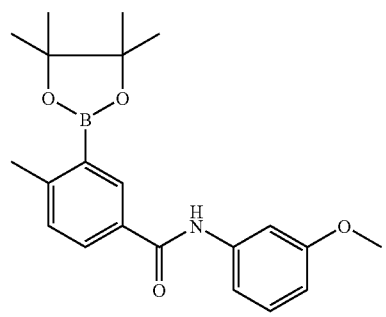

4-Methyl-3-(4,4,5,5-tetramethyl-[1,3,2]dioxaborolan-2-yl)-benzoic acid (Intermediate 21) (2 g) was dissolved in dimethylformamide (20 ml). To this was added 3-methoxyaniline (0.985 g), di-isopropylethylamine (4 ml) and HATU (3.05 g). The mixture was stirred for 18 hours at room temperature. The solvent was removed in vacuo and the residue partitioned between ethyl acetate (250 ml) and water (50 ml). The organic layer was dried over magnesium sulfate, filtered and removed in vacuo to give the crude material. The product was purified using silica Biotage cartridge (90 g) eluting with 1:4 ethylacetate/cyclohexane to give a white solid (2.06 g, 5.61 mmol).

NMR: δH [$^2$H$_6$]—DMSO 10.20, (1H, s), 8.17, (1H, s), 7.94-7.91, (1H, dd), 7.45 (1H, s), 7.36-7.32, (2H, t), 7.25-7.21, (1H, t), 6.68-6.65, (1H, dd), 3.74, (3H, s), 2.53, (3H, s), 1.32, (12H, s) ppm. LCMS retention time 3.80 min MH$^+$ 368.

Intermediate 7: 2-Chloromethyl-5-(4-iodophenyl)-[1,3,4]oxadiazole

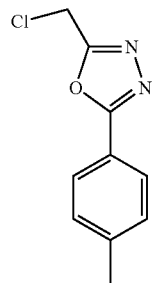

5-(4-Iodophenyl)-1H-tetrazole (1.00 g, 3.68 mmol) and chloroacetic anhydride (3.77 g, 22.1 mmol) were heated at 95° C. for 3 hours. The crude product was purified on a 10 g silica SPE cartridge with 5:95 ethyl acetate:cyclohexane to 20:80 ethyl acetate:cyclohexane. The desired product crystallised spontaneously. The title compound was isolated as white crystals, which were filtered off and washed with cold cyclohexane (690 mg, 59%)

NMR: δH CDCl₃ 7.89 (2H, d), 7.80 (2H,d), 4.78 (2H,s) ppm. LCMS: retention time 3.23 min, MH⁺ 321.

Intermediate 8: 2-(4-Iodophenyl)-5-pyrrolidin-1-ylmethyl-[1,3,4]oxadiazole

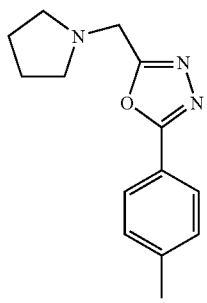

2-Chloromethyl-5-(4-iodophenyl)-[1,3,4]oxadiazole (Intermediate 7) (48 mg, 0.15 mmol) and potassium iodide (25 mg, 0.15 mmol) were dissolved in pyrrolidine (2 ml) and stirred for 18 hours at 20° C. The amine was then removed in vacuo and the product was purified on a 10 g silica SPE cartridge (stepped solvent gradient 80:20 ethyl acetate:cyclohexane, 100% ethyl acetate, 95:5 ethyl acetate:methanol).

NMR: δH [²H₆]—DMSO 7.84 (2H, d), 7.62 (2H, d), 3.80 (2H, s), 2.44 (4H, br), 1.57 (4H, br) ppm. LCMS: retention time 2.15 min, MH⁺ 356.

Intermediate 9: 1-[5-(4-Iodophenyl)-[1,3,4]oxadiazol-2-ylmethyl]-piperidine

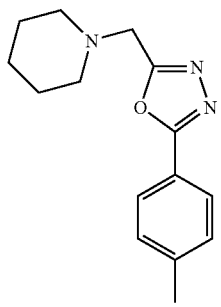

2-Chloromethyl-5-(4-iodophenyl)-[1,3,4]oxadiazole (Intermediate 7) (48 mg, 0.15 mmol) and potassium iodide (25 mg, 0.15 mmol) were dissolved in piperidine (2 ml) and stirred for 18 hours at 20° C. The amine was then removed in vacuo and the product was purified on a 10 g silica SPE cartridge (stepped solvent gradient 80:20 ethyl acetate:cyclohexane, 100% ethyl acetate, 95:5 ethyl acetate:methanol).

NMR: δH—CDCl₃ 7.87 (2H, d), 7.80 (2H, d), 3.87 (2H, brs), 2.56 (4H, br), 1.64 (4H, br), 1.45 (2H, br) ppm. LCMS: retention time 2.25 min, MH⁺ 370.

Intermediate 10: 4-[5-(4-Iodophenyl)-[1,3,4]oxadiazol-2-ylmethyl]-morpholine

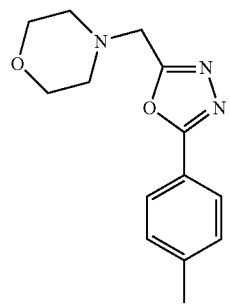

2-Chloromethyl-5-(4-iodophenyl)-[1,3,4]oxadiazole (Intermediate 7) (48 mg, 0.15 mmol) and potassium iodide (25 mg, 0.15 mmol) were dissolved in morpholine (2 ml) and stirred for 18 hours at 20° C. The amine was then removed in vacuo and the product was purified on a 10 g silica SPE cartridge (stepped solvent gradient 80:20 ethyl acetate:cyclohexane, 100% ethyl acetate, 95:5 ethyl acetate:methanol).

NMR: δH—CDCl₃ 7.88 (2H, d), 7.79 (2H, d), 3.89 (2H, s), 3.76 (4H, br), 2.65 (4H, br) ppm. LCMS: retention time 2.73 min MH⁺ 372.

Intermediate 11: [5-(4-Iodophenyl)-[1,3,4]oxadiazol-2-ylmethyl]-dimethylamine

2-Chloromethyl-5-(4-iodophenyl)-[1,3,4]oxadiazole (Intermediate 7) (48 mg, 0.15 mmol) and potassium iodide (25 mg, 0.15 mmol) were dissolved in 2M dimethylamine in tetrahydrofuran (2 ml) and stirred for 18 hours at 20° C. The reaction was evaporated to dryness in vacuo and the product was purified on a 10 g silica SPE cartridge (stepped solvent gradient 80:20 ethyl acetate:cyclohexane, 100% ethyl acetate, 95:5 ethyl acetate:methanol).

NMR: δH—CDCl₃ 7.87 (2H, d), 7.80 (2H, d), 3.85 (2H, s), 2.42 (6H, s) ppm. LCMS: retention time 2.09 min, MH⁺ 330.

Intermediate 12:
5(4Iodophenyl)-3-methyl-[1,2,4]oxadiazole

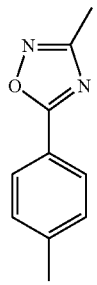

1,1'-Carbonyldiimidazole (0.49 g, 3 mmol) was added to a solution of 4-iodobenzoic acid (0.5 g, 2 mmol) in dry dimethylformamide (4 ml) and stirred at room temperature for 30 minutes. N-hydroxy-acetamidine (0.224 g, 3 mmol) was added and stirring at room temperature continued for 16 hours. Sodium methoxide in methanol (25% wt solution; 1.1 ml, 5 mmol) was added and the mixture heated at 80° C. for 6 hours. Once cool, ethyl acetate (50 ml) and water (50 ml) were added. The organic layer was washed with water (50 ml), brine (50 ml), dried over magnesium sulfate, filtered and solvent removed in vacuo. The residue was purified by silica SPE cartridge (5 g) (100% cyclohexane, 20:1 cyclohexane/ethyl acetate v:v to 10:1 cyclohexane/ethyl acetate v:v) to yield the desired product as a white solid (0.15 g, 0.52 mmol).

NMR: $\delta$H—CDCl$_3$ 7.89, (2H, d), 7.83, (2H, d), 2.48, (3H, s) ppm. LCMS: Retention time 3.33 mins.

Intermediate 13: 4Iodo-benzoic acid N'-(2,2-dimethyl-propionyl)-hydrazide

4-Iodobenzoic acid (5 g, 20.2 mmol) was dissolved in dimethylformamide (50 ml). To this was added tert-butyl carbazate (2.66 g, 20.2 mmol), HATU (9.2 g, 24.2 mmol), 1-hydroxybenzotriazole (2.7 g, 20.2 mmol) and N,N-diisopropylethylamine (10.5 ml, 60.5 mmol). The mixture was stirred for 17 hours at room temperature. The solvent was removed in vacuo and the residue partitioned between dichloromethane (75 ml) and saturated aqueous sodium bicarbonate solution (75 ml). The organic layer was washed with water (100 ml), brine (100 ml), dried over magnesium sulfate, filtered and the solvent removed in vacuo. The desired product was obtained as a cream solid (4.6 g, 12.7 mmol).

NMR: $\delta$H [$^2$H$_6$]—DMSO 10.25, (1H, s), 8.92, (1H, bs), 7.87, (2H, d), 7.61, (2H, d), 1.41, (9H, s) ppm. LCMS: Retention time 3.06 mins, M–H$^+$ 361.

Intermediate 14: 4-Iodobenzoic acid hydrazide

Trifluoroacetic acid (10 ml) was added to 4iodo-benzoic acid N'-(2,2-dimethyl-propionyl)-hydrazide (Intermediate 13) (1 g, 2.76 mmol) and stirred at room temperature for 2 hours. The trifluoroactic acid was removed in vacuo and the residue partitioned between ethyl acetate (50 ml) and saturated aqueous sodium bicarbonate solution (50 ml). The organic layer was washed with water (50 ml), brine (50 ml), dried over magnesium sulfate, filtered and the solvent removed in vacuo. The desired product was obtained as a white solid (0.55 g, 2.1 mmol).

NMR: $\delta$H [$^2$H$_6$]—DMSO 9.82, (1H, s), 7.82, (2H, d), 7.58, (2H, d), 4.49, (2H, bs) ppm. LCMS: Retention time 2.34 mins.

Intermediate 15:
2(4-Iodophenyl)-5-methyl-[1,3,4]oxadiazole

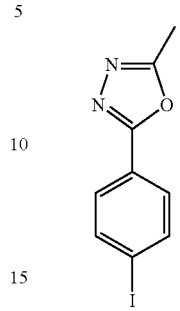

Triethyl orthoacetate (10 ml) was added to 4-iodo-benzoic acid hydrazide (Intermediate 14) (0.55 g, 2.1 mmol) and heated under nitrogen at 130° C. for 3 hours. The triethyl orthoacetate was removed in vacuo and the residue partitioned between ethyl acetate (30 ml) and water (30 ml). The organic layer was washed with water (50 ml), brine (50 ml), dried over magnesium sulfate filtered and the solvent removed in vacuo. The residue was purified by silica SPE cartridge (10 g) eluting with 20:1 cyclohexane/ethyl acetate v:v to 5:1 cyclohexane/ethyl acetate v:v. The desired product was obtained as a white solid (0.31 g, 1.1 mmol).

NMR: $\delta$H [$^2$H$_6$]—DMSO 7.96, (2H, d), 7.72, (2H, d), 2.56, (3H, s) ppm. LCMS: Retention time 3.02 mins.

Intermediate 16:
N-Cyclopropyl-3-iodo-4-methylbenzamide

3-Iodo-4-methylbenzoic acid (1.0 g, 3.8 mmol) was heated at 80° C. in thionyl chloride (10 ml) for 2 hrs. The reaction was allowed to cool to room temperature and the excess thionyl chloride evaporated under vacuum. The residue was dissolved in DCM (10 ml), cyclopropylamine (0.32 ml) and sodium carbonate (2.0 g) were added to the solution. The reaction was stirred at room temperature for 18 hrs, filtered and the filtrate reduced to dryness under vacuum. The residue was triturated with ether to give N-cyclopropyl-3-iodo-4-methylbenzamide as a white solid (1.1 g).

NMR: $\delta$H [$^2$H$_6$]—DMSO 8.46, (1H, d), 8.24, (1H, d), 7.74, (1H, dd), 7.38, (1H, d), 2.82, (1H, m), 2.38, (3H, s), 0.67, (2H, m), 0.55, (2H, m).

Intermediate 17: N-Cyclopropyl-4-methyl-3-(4,4,5,5-tetramethyl-[1,3,2]dioxaborolan-2-yl)-benzamide N-Cyclopropyl-3-iodo-4-methylbenzamide (Intermediate 16) (1.1 g, 3.64 mmol), bis(pinnacolato)diboron (1.85 g, 7.28 mmol), potassium acetate (1.79 g, 18.2 mmol) and PdCl$_2$dppf (55 mg) were heated at 85° C. in DMF (30 ml) for 4.5 hrs. The cooled reaction was absorbed onto silica, applied to a bond-elut (10 g, silica) and eluted with an ethylacetate/cyclohexane gradient (0 to 100%). The solvent was evaporated from the product fractions under vacuum and the residue triturated with cyclohexane to give N-cyclopropyl-4-methyl-3-(4,4,5,5-tetramethyl-[1,3,2]dioxaborolan-2-yl)-benzamide as a white solid (650 mg).

NMR: $\delta$H [$^2$H$_6$]—DMSO 8.40, (1H, d), 8.06, (1H, d), 7.76, (1H, dd), 7.23, (1H, d), 2.82, (1H, m), 2.48, (3H, s), 1.30, (12H, s), 0.66, (2H, m), 0.56, (2H, m).

Intermediate 18: 2-Chloro-N-(3-iodo-4-methylphenyl)-isonicotinamide

2-Chloroisonicotinic acid (3.3 g, 21 mmol), HATU (8.75 g, 23 mmol), diisopropylethyl amine (10.9 ml, 63 mmol) and 3-iodo-4-methylaniline (5.00 g, 21 mmol) in dimethylformamide (50 ml) were heated under nitrogen for 16 hours. The reaction was cooled, solvent removed in vacuo and the residue taken up in dichloromethane (150 ml). The organic solution was washed with water (3×100 ml) and brine (100 ml), dried over magnesium sulfate, filtered and solvent removed in vacuo. The residue was purified by column chromatography (40:60 ethyl acetate:cyclohexane) to give 2-chloro-N-(3-iodo-4-methylphenyl)-isonicotinamide as a white solid (7.00 g, 18.8 mmol).

LCMS: retention time 3.59 min MH$^+$373. NMR: δH [$^2$H$_6$]—DMSO 10.52 (1H, s), 8.62 (1H, d), 8.29 (1H, d), 7.99 (1H, b), 7.87 (1H, dd), 7.70 (1H, dd), 7.34 (1H, d), 2.36 (3H, s).

Intermediate 19: N-(3-Iodo-4-methylphenyl)-2-pyrrolidin-1-yl-isonicotinamide A solution of N-(3-iodo-4-methylphenyl)-2-chloro-isonicotinamide (Intermediate 18) (7.00 g, 18.8 mmol) in pyrrolidine (20 ml) was heated at 80° C. under an atmosphere of nitrogen for 16 hours. Excess pyrrolidine was removed in vacuo and the residue was titurated with diethyl ether (20 ml). The resulting solid was collected by filtration and dried in vacuo to give N-(3-iodo-4-methylphenyl)-2-pyrrolidin-1-yl-isonicotinamide as a pale yellow solid (7.73 g, 18 mmol). LCMS: retention time 2.77 min MH$^+$408. NMR: δH [$^2$H$_6$]—DMSO 10.29 (1H, s), 8.29 (1H, d), 8.20 (1H, d), 7.71 (1H, dd), 7.72 (1H, dd), 6.97 (1H, brd), 6.88 (1H, b), 3.45 (2H, apparent t), 3.09 (2H, m), 2.35 (3H, s), 1.98 (2H, m), 1.82 (2H, m).

Intermediate 20: N-[4-Methyl-3-(4,4,5,5-tetramethyl-[1,3,2]-dioxaborolan-2-yl)phenyl]-2-(1-pyrrolidinyl)-4-pyridinecarboxamide Bis(pinacolato)diborane (7.24 g, 28.5 mmol) was added to a mixture of N-(3-iodo-4-methylphenyl)-2-pyrrolidin-1-yl-isonicotinamide (Intermediate 19) (7.73 g, 19 mmol) in dimethylformamide (100 ml) potassium acetate (9.32 g, 95 mmol) and PdCl$_2$dppf and the reaction was heated under an atmosphere of nitrogen at 80° C. for 16 hours. The reaction was cooled and the solvent removed in vacuo. The residue was taken up in chloroform (150 ml), washed with water (3×100 ml) and brine (100 ml), dried over magnesium sulfate, filtered and solvent removed in vacuo. The residue was purified by column chromatography (20:80 ethyl acetate:cyclohexane to 50:50 ethyl acetate:cyclohexane) to give N-[4-methyl-3-(4,4,5,5-tetramethyl-[1,3,2]-dioxaborolan-2-yl)phenyl]-2-(1-pyrrolidinyl)-4-pyridinecarboxamide as a white solid (1.5 g, 3.7 mmol).

LCMS: retention time 2.90 min MH$^+$408. NMR: δH—CDCl$_3$ 8.27 (1H, d), 7.99 (1H, dd), 7.76 (1H, b), 7.65 (1H, d), 6.20 (1H, d), 6.82 (1H, b), 6.77 (1H, b), 3.52 (4H, apparent t), 2.52 (3H, s), 2.25 (4H, m), 1.35 (12H, s).

Intermediate 21: 4-Methyl-3-(4,4,5,5-tetramethyl-[1,3,2]dioxaborolan-2-yl)benzoic acid 3-Iodo-4-methylbenzoic acid (10 g, 38.16 mmol), bis(pinacolato)diboron (14.5 g, 57.24 mmol), potassium acetate (18.73 g, 190.8 mmol) and PdCl$_2$dppf (3.12 g, 3.8 mmol) in DMF (200 ml) were heated at 80° C. for 21 hrs. The solvent was evaporated from the cooled reaction under vacuum, the residue dissolved in ethyl acetate (300 ml) and hydrochloric acid (2N, 300 ml) and filtered through celite. The organic phase was separated and the aqueous extracted with ethyl acetate (2×300ml). The combined organic extracts were washed with brine (500 ml) and dried (magnesium sulphate). The solvent was evaporated under vacuum and the residue absorbed onto silica and applied to a silica flash column. This was eluted with cyclohexane/ethyl acetate (5:1). The product fractions were concentrated under vacuum to give 4-methyl-3-(4,4,5,5-tetramethyl-[1,3,2]dioxaborolan-2-yl)benzoic acid.

LCMS: retention time 3.65 min. NMR: δH [$^2$H$_6$]—DMSO 12.83, (1H, b), 8.23, (1H, d), 7.89, (1H, dd), 7.29, (1H, d), 2.51, (3H, s), 1.30, (12H, s).

Intermediate 22: 4-Methyl-3-(4,4,5,5-tetramethyl-[1,3,2]dioxaborolan-2-yl)-N-(thiazol-2-yl)-benzamide 4-Methyl-3-(4,4,5,5-tetramethyl-[1,3,2]dioxaborolan-2-yl)-benzoic acid (Intermediate 21) (2.0 g, 7.63 mmol), DIPEA (4 ml, 22.89 mmol) and HATU (3.05 g, 8.02 mmol) were dissolved in DMF (20 ml) and stirred at room temperature for 15 mins. 2-Aminothiazole (801 mg, 8.01 mmol) was added and the reaction stirred at room temperature for 18 hours. The solvent was evaporated under vacuum and the reaction partitioned between ethyl acetate (250 ml) and water (50 ml). The organic phase was washed with hydrochloric acid (2N, 50 ml) and aqueous sodium bicarbonate (1M, 50 ml), then dried (magnesium sulphate) and the solvent evaporated under vacuum. The residue was absorbed onto silica and purified by flash column chromatography eluting with cyclohexane/ethyl acetate (4:1). The solvent was evaporated from the product fractions under vacuum to give 4-methyl-3-(4,4,5,5-tetramethyl-[1,3,2]dioxaborolan-2-yl)-N-(thiazol-2-yl)-benzamide (1.72 g).

LCMS: retention time 3.66 min, MH$^+$ 345. NMR: δH [$^2$H$_6$]—DMSO 12.65, (1H, b), 8.32, (1H, d), 8.08, (1H, dd), 7.56(1H, d), 7.35(1h, d), 7.28(1H, d), 2.54, (3H, s), 1.34, (12H, s).

Intermediate 23: 4-Methyl-3-(4,4,5,5-tetramethyl-[1,3,2]dioxaborolan-2-yl)-N-([1,3,4]thiadiazol-2-yl)-benzamide 4-Methyl-3-(4,4,5,5-tetramethyl-[1,3,2]dioxaborolan-2-yl)-benzoic acid (Intermediate 21) (2.0 g, 7.63 mmol), DIPEA (4 ml, 22.89 mmol) and HATU (3.05 g, 8.02 mmol) were dissolved in DMF (20 ml) and stirred at room temperature for 15 mins. 2-Aminothiadiazole (810 mg, 8.01 mmol) was added and the reaction stirred at room temperature for 18 hours. The solvent was evaporated under vacuum and the reaction partitioned between ethyl acetate (250 ml) and hydrochloric acid (2N, 150 ml). The aqueous phase was extracted with ethylacetate (2×250 ml). The combined organic extracts were dried (magnesium sulphate) and the solvent evaporated under vacuum. The residue was absorbed onto silica and purified by flash column chromatography eluting with cyclohexane/ethyl acetate (4:1 then 1:1). The solvent was evaporated from the product fractions under vacuum to give 4-methyl-3-(4,4,5,5-tetramethyl-[1,3,2]dioxaborolan-2-yl)-N-([1,3,4]thiadiazol-2-yl)-benzamide (0.95 g).

LCMS: retention time 3.34 min, MH$^+$ 346. NMR: δH [$^2$H$_6$]—DMSO 13.08, (1H, b), 9.22, (1H, s), 8.35, (1H, d), 8.11(1H, dd), 7.38(1H, d), 2.55(3H, s), 1.34, (12H, s).

Intermediate 24:
N-(3-Iodo-4-methylphenyl)-3-furamide

3-Furoic acid (2.4 g, 21.45 mmol) and HATU (8.15 g, 21.45 mmol) in DMF (25 ml) were stirred at room temperature for 15 mins. HOBT (2.9 g, 21.45 mmol), 3-iodo-4-methylaniline (5.0 g, 21.45 mmol) and DIPEA (11.2 ml, 64.35 mmol) were added and the reaction stirred at room temperature for 16 hrs. The solvent was evaporated under vacuum and the residue partitioned between ethyl acetate (100 ml) and aqueous sodium carbonate (10%, 100 ml). The aqueous layer was extracted with ethyl acetate (50 ml) and the combined organic phases washed with hydrochloric acid (2N, 75 ml), water (75 ml) and brine (75 ml). The organic phase was dried (magnesium sulphate) and absorbed onto silica. The silica was applied to a flash silica column and eluted with cyclohexane/ethyl acetate (3:1). The solvent was evaporated from the product fractions under vacuum to give N-(3-iodomethylphenyl)-3-furamide.

LCMS: retention time 3.52 min, MH$^+$ 328. NMR: δH [$^2$H$_6$]—DMSO 9.92, (1H, b), 8.36, (1H, d), 8.23, (1H, d), 7.80, (1H, t), 7.66, (1H, dd), 7.29, (1H, d), 6.98, (1H, d), 2.33, (3H, s).

Intermediate 25: N-[4-Methyl-3-(4,4,5,5-tetramethyl-[1,3,2]dioxaborolan-2-yl)-phenyl]-3-furamide N-(3-Iodo-4-methylphenyl)-3-furamide (Intermediate 24) (2.5 g, 7.64 mmol), bis(pinnacolato)diboron (2.13 g, 8.41 mmol), potassium acetate (825 mg, 8.41 mmol) and PdCl$_2$dppf (312 mg, 0.38 mmol) in DMF (20 ml) were heated at 80° C. for 20 hrs. The cooled reaction was absorbed onto silica and applied to a bond-elut (silica, 10 g) and eluted with a cyclohexane/ethyl acetate gradient. The product fractions were concentrated under vacuum, dissolved in DMP (40 ml) and reacted with bis(pinnacolato)diboron (7.76 g, 30.57 mmol), potassium acetate (3.0 g, 30.57 mmol) and PdCl$_2$dppf (249 mg, 0.306 mmol) at 80° C. for 23 hrs. The cooled reaction was absorbed onto silica and applied to bond-eluts (silica, 2×10 g) and eluted with a cyclohexane/ethyl acetate gradient. The product fractions were concentrated under vacuum to give N-[4-methyl-3-(4,4,5,5-tetramethyl-[1,3,2]dioxaborolan-2-yl)-phenyl]-3-furamide.

LCMS: retention time 3.55 min, MH$^+$ 328. NMR: δH [$^2$H$_6$]—DMSO 9.86, (1H, b), 8.36, (1H, m), 7.86-7.82, (2H, m), 7.77, (1H, t), 7.14(1H, d), 6.99(1H, m), 2.41, (3H, s), 1.30, (12H, s).

Intermediate 26:
N-(3-Iodo-4-methylphenyl)thiophene-3-amide

Thiophene-3-carboxylic acid (2.75 g, 21.45 mmol) and HATU (8.15 g, 21.45 mmol) in DMF (25 ml) were stirred at room temperature for 15 mins. HOBT (2.9 g, 21.45 mmol), 3-iodo-4-methylaniline (5.0 g, 21.45 mmol) and DIPEA (11.2 ml, 64.35 mmol) were added and the reaction stirred at room temperature for 16 hrs. The solvent was evaporated under vacuum and the residue partitioned between ethyl acetate (100 ml) and aqueous sodium carbonate (10%, 100 ml). The aqueous layer was extracted with ethyl acetate (50 ml) and the combined organic phases washed with hydrochloric acid (2N, 75 ml), water (75 ml) and brine (75 ml). The organic phase was dried (magnesium sulphate) and absorbed onto silica. The silica was applied to a flash silica column and eluted with cyclohexane/ethyl acetate (4:1). The solvent was evaporated from the product fractions under vacuum to give N-(3-iodo-4-methylphenyl)thiophene-3-amide.

LCMS: retention time 3.69 min, MH$^+$ 344. NMR: δH [$^2$H$_6$]—DMSO 10.06, (1H, b), 8.34, (1H, m), 8.29, (1H, d), 7.70, (1H, dd), 7.66, (1H, dd), 7.62, (1H, dd), 7.30, (1H, d), 2.34, (3H, s).

Intermediate 27: N-[4-Methyl-3-(4,4,5,5-tetramethyl-[1,3,2]dioxaborolan-2-yl)-phenyl]thiophene-3-amide N-(3-Iodo-4-methylphenyl)thiophene-3-amide (Intermediate 26) (2.64 g, 7.64 mmol), bis(pinnacolato)diboron (2.13 g, 8.41 mmol), potassium acetate (825 mg, 8.41 mmol) and PdCl$_2$dppf (312 mg, 0.38 mmol) in DMF (20 ml) were heated at 80° C. for 20 hrs. The cooled reaction was absorbed onto silica and applied to a bond-elut (silica, 10 g) and eluted with a cyclohexane/ethyl acetate gradient. The product fractions were concentrated under vacuum, dissolved in DMF (20 ml) and reacted with bis(pinnacolato)diboron (1.77 g, 7.0 mmol), potassium acetate (687 mg, 7.0 mmol) and PdCl$_2$dppf (143 mg, 0.175 mmol) at 80° C. for 16 hrs. The cooled reaction was absorbed onto silica and applied to a bond-elut (silica, 10 g) and eluted with a cyclohexane/ethyl acetate gradient. The product fractions were concentrated under vacuum to give N-[4-methyl-3-(4,4,5,5-tetramethyl-[1,3,2]dioxaborolan-2-yl)-phenyl]thiophene-3-amide.

LCMS: retention time 3.65 min, MH$^+$ 344. NMR: δH [$^2$H$_6$]—DMSO 9.99, (1H, b), 8.35, (1H, s), 7.90, (1H, d), 7.85(1H, dd), 7.63(2H, m), 7.14(1H, d), 2.42, (3H, s), 1.30, (12H, s).

Intermediate 28: N-Cyclopropylmethyl-4-methyl-3-(4,4,5,5-tetramethyl-[1,3,2]dioxaborolan-2-yl)-benzamide 4-Methyl-3-(4,4,5,5-tetramethyl-[1,3,2]dioxaborolan-2-yl)-benzoic acid (Intermediate 21) (2.0 g, 7.63 mmol), DIPEA (4 ml, 22.89 mmol) and HATU (3.05 g, 8.02 mmol) were dissolved in DMF (20 ml) and stirred at room temperature for 15 mins. Cyclopropylmethylamine (568 mg, 8.01 mmol) was added and the reaction stirred at room temperature for 18 hours. The solvent was evaporated under vacuum and the reaction partitioned between ethyl acetate (250 ml) and water (50 ml). The organic phase was washed with hydrochloric acid (2N, 50 ml) and aqueous sodium bicarbonate (1M, 50 ml), then dried (magnesium sulphate) and the solvent evaporated under vacuum. The residue was absorbed onto silica and purified by flash column chromatography eluting with cyclohexane/ethyl acetate (4:1). The solvent was evaporated from the product fractions under vacuum to give N-cyclopropylmethyl-4-methyl-3-(4,4,5,5-tetramethyl-[1,3,2]dioxaborolan-2-yl)-benzamide (1.73 g).

LCMS: retention time 3.47 min, MH$^+$ 316. NMR: δH [$^2$H$_6$]—DMSO 8.54, (1H, t), 8.11, (1H, d), 7.82, (1H, dd), 7.26, (1H, d), 3.12, (2H, t), 1.32, (12H, s), 1.03, (1H, m), 0.42, (2H, m), 0.22, (2H, m).

Intermediate 29: N-Cyclopropyl-5-fluoro-4'-(hydrazinocarbonyl)-6-methyl-1,1'-biphenyl-3-carboxamide A solution of tert-butyl 2-({5'-[(cyclopropylamino)carbonyl]-3'-fluoro-2'-methyl-1,1'-biphenyl-4-yl}carbonyl)hydrazinecarboxylate (Intermediate 30) (400 mg) in hydrogen chloride (4.0M solution in dioxane, 5 ml) was stirred at room temperature under nitrogen for 16 hours. Methanol was added to form a solution and the solvents evaporated under vacuum. The residue was partially dissolved in water, basified with sodium hydroxide solution (2N, 10 ml) and extracted with ethyl acetate (120 ml). The organic phase was dried and the solvent removed under vacuum to give the N-cyclopropyl-5-fluoro-4'-(hydrazinocarbonyl)-6-methyl-1,1'-biphenyl-3-carboxamide.

LCMS: MH+ 328, retention time 2.53 minutes.

Intermediate 30: tert-Butyl 2-({5'-[(cyclopropylamino)carbonyl]-3'-fluoro-2'-methyl-1,1'-biphenyl-4-yl}carbonyl)hydrazinecarboxylate N-Cyclopropyl-5-fluoro-4-methyl-3-(4,4,5,5-tetramethyl-[1,3,2]dioxaborolan-2-yl)-benzamide (Intermediate 32) (3.27 g), 4-bromo-benzoic acid N'-(2,2-dimethyl-propionyl)-hydrazide (Intermediate 31) (3.39 g), tetrakis(triphenylphosphine)palladium (238 mg) and aqueous sodium hydrogen carbonate (1M, 21.6 ml) were mixed in propan-2-ol (20 ml) and heated at 90° C. under nitrogen for 18 hours. The cooled reaction mixture was reduced to dryness under vacuum, the residue partially dissolved in ethyl acetate and filtered. The filtrate was absorbed onto silica and purified by chromatography on silica biotage columns (2×100 g), eluting with ethyl acetate/cyclohexane (2:3). The product fractions were reduced to dryness under vacuum to give tert-butyl 2-({5'-[(cyclopropylamino)carbonyl]-3'-fluoro-2'-methyl-1, 1'-biphenyl-4-yl}carbonyl)hydrazinecarboxylate.

LCMS: MH+ 428, retention time 3.14 minutes.

Intermediate 31: 4-Bromo-benzoic acid N'-(2,2-dimethyl-propionyl)-hydrazide t-Butyloxycarbonylhydrazine (1.26 g) was added portionwise to a solution of 4-bromobenzoyl chloride (2.0 g), and DIPEA (2.37 ml) in DCM (20 ml) and the reaction stirred at room temperature for 18 hours. Ammonium chloride solution was added, the organic phase was separated, dried and the solvent evaporated under vacuum to give 4-bromo-benzoic acid N'-(2,2-dimethyl-propionyl)-hydrazide.

LCMS: [M−H]− 313/315, retention time 2.97 minutes.

Intermediate 32: N-Cyclopropyl-5-fluoro-4-methyl-3-(4,4,5,5-tetramethyl-[1,3,2]dioxaborolan-2-yl)-benzamide 3-Bromo-N-cyclopropyl-5-fluoro-4-methylbenzamide (Intermediate 33) (900 mg), bispinnacolatodiboron (4.5 g), potassium acetate (2.1 g) and PdCl$_2$dppf (75 mg) were mixed in DMP (40 ml) and heated at 100° C. for 18 hours. The cooled reaction was absorbed onto silica and applied to bond-eluts (Si 2×10 g) and eluted with an ethyl acetate/cyclohexane gradient (0-6.25% ethylacetate). The solvent was evaporated from the product fractions under vacuum and the residue recrystallized from cyclohexane to give N-cyclopropyl-5-fluoro-4-methyl-3-(4,4,5,5-tetramethyl-[1,3,2]dioxaborolan-2-yl)-benzamide (260 mg).

LCMS: MH+ 320, retention time 3.39 mins.

Intermediate 33: 3-Bromo-N-cyclopropyl-5-fluoro-4-methylbenzamide

3-Fluoro-4-methylbenzoic acid (462 mg, 3.0 mmol) was added to a stirred mixture of bromine (2.31 ml, 45 mmol) and iron powder (252 mg, 4.5 mmol) under nitrogen. The reaction was stirred at 20° C. for 4 hours and then left to stand for 16 hours. Sodium thiosulphate solution (200 ml) was added and the product was extracted into ethyl acetate (3×150 ml). Ethyl acetate extracts were combined and evaporated in vacuo. The crude product (mixture of isomers) was dissolved in dimethylformamide (7 ml). Cyclopropylamine (208 µl, 3.0 mmol), HOBT (405 mg, 3.0 mmol), 1-(3-dimethylaminopropyl)-3-ethylcarbodiimide hydrochloride (575 mg, 3.0 mmol) and DIPEA (525 µl, 3.0 mmol) were added to the stirred solution. The reaction was stirred for 5 hours at 20° C. Solvent was removed in vacuo and the residue was partitioned between ethyl acetate and water. Combined ethyl acetate extracts were washed sequentially with aqueous sodium hydrogen carbonate and hydrochloric acid (0.5M), then dried (magnesium sulphate). The ethyl acetate was evaporated in vacuo and the residue was purified by silica biotage chromatography eluting with cyclohexane:ethyl acetate (6: 1) to give 3-bromo-N-cyclopropyl-5-fluoro4methylbenzamide (359 mg, 44%).

NMR: δH—CDCl$_3$ 7.68, (1H, s), 7.39(1H, d), 6.19(1H, bs), 2.88(1H, m), 2.36, (3H, d), 0.88, (2H, m), 0.63, (2H, m). LCMS: MH+ 272.

Intermediate 34: 4'-[5-(Chloromethyl)-1,3,4-oxadiazol-2-yl]-N-cyclopropyl-5-fluoro-6-methyl-1,1'-biphenyl-3-carboxamide N-Cyclopropyl-5-fluoro-4'-(hydrazinocarbonyl)-6-methyl-1,1'-biphenyl-3-carboxamide (Intermediate 29) (580 mg) in 2-chloro-1,1,1-triethoxyethane (2.5 ml) was heated at 80° C. for 20 hours. The reaction was absorbed onto silica and purified by chromatography on a biotage column (silica, 40 g), eluting with cyclohexane and then with ethyl acetate/cyclohexane (2:3). The product fractions were reduced to dryness under vacuum to give 4'-[5-(chloromethyl)-1,3,4-oxadiazol-2-yl]-N-cyclopropyl-5-fluoro-6-methyl-1,1'-biphenyl-3-carboxamide.

LCMS: MH+ 385, retention time 3.34 minutes.

Intermediate 35: 4'-[5-(Azidomethyl)-1,3,4-oxadiazol-2-yl]-N-cyclopropyl-5-fluoro-6-methyl-1,1'-biphenyl-3-carboxamide A solution of sodium azide (40 mg) in water (3.5 ml) was added to (4'-[5-(chloromethyl)-1,3,4-oxadiazol-2-yl]-N-cyclopropyl-5-fluoro-6-methyl-1,1'-biphenyl-3-carboxamide (Intermediate 34) (200 mg) in DMF (1.5 ml) and ethanol (7 ml) and the reaction mixture stirred for 5 hours at 90° C. The reaction was concentrated under vacuum and the residue partitioned between water (15 ml) and chloroform (15 ml) and the aqueous extracted with chloroform (2×15 ml). The combined organic extracts were dried (magnesium sulphate), and the solvent evaporated under vacuum to give 4'-[5-(azidomethyl)-1,3,4-oxadiazol-2-yl]-N-cyclopropyl-5-fluoro-6-methyl-1,1'-biphenyl-3-carboxamide.

LCMS: MH+ 392, retention time 3.16 minutes.

Intermediate 36: 2-(4-Iodophenyl)-5-(methylamino)-1,3,4-oxadiazole

Phosphorousoxychloride (2 ml) was added to benzoic acid, 4-iodo-2-[(methylamino)carbonyl]hydrazide (Intermediate 37) (100 mg) in acetonitrile (1 ml) and the reaction heated at 100° C. for 18 hours. The cooled reaction was poured onto ice/water (60 ml) and extracted with ethyl acetate (3×40 ml). The combined extracts were reduced to dryness under vacuum and the residue applied to a bond-elut (silica) and eluted with an ethyl acetate/cyclohexane gradient, to give, after evaporation of the solvent 2-(4-iodophenyl)-5-(methylamino)-1,3,4-oxadiazole.

LCMS: MH+ 302.

Intermediate 37: Benzoic acid, 4-iodo-2-[(methylamino)carbonyl]hydrazide

4-Methylsemicarbazide (89 mg), EDC (230 mg), HOBt (162 mg), 4-iodobenzoic acid (248 mg) and DIPRA (0.21 ml) were mixed in DMF (3 ml). The reaction was heated at 40° C. for 6 hours, the DME was evaporated under vacuum and the residue applied to a bond-elut (silica) and eluted with an ethyl acetate/cyclohexane gradient to give, after evaporation of the solvent, benzoic acid, 4-iodo-2-[(methylamino)carbonyl]hydrazide.

LCMS: MH$^+$ 320, retention time 2.29 minutes.

Intermediate 38: 2-(4-Iodophenyl)-5-(1-methyl-1H-pyrrol-2-yl)-1,3,4-oxadiazole Phosphorousoxychloride (2 ml) was added to 1H-pyrrole-2-carboxylic acid, 1-methyl-2-(4-iodobenzoyl)hydrazide (Intermediate 39) (150 mg) in acetonitrile (1 ml) and the reaction heated at 100° C. for 18 hours. The cooled reaction was poured onto ice/water (60 ml) and extracted with ethyl acetate (3×40 ml). The combined extracts were reduced to dryness under vacuum and the residue applied to a bond-elut (silica) and eluted with an ethyl acetate/cyclohexane gradient to give, after evaporation of the solvent, 2-(4-iodophenyl)-5-(1-methyl-1H-pyrrol-2-yl)-1,3,4-oxadiazole.

LCMS: MH$^+$ 352, retention time 3.7 minutes.

Intermediate 39: 1H-Pyrrole-2-carboxylic acid, 1-methyl-2-(4-iodobenzoyl)hydrazide 1H-Pyrrole-2-carboxylic acid, 1-methyl-hydrazide (139 mg), EDC (230 mg), HOBt (162 mg), 4-iodobenzoic acid (248 mg) and DIPEA (0.21 ml) were mixed in DMF (3 ml). The reaction was heated at 40° C. for 6 hours, the DMF was evaporated under vacuum and the residue applied to a bond-elut (silica) and eluted with an ethyl acetate/cyclohexane gradient to give, after evaporation of the solvent, 1H-pyrrole-2-carboxylic acid, 1-methyl-2-(4-iodobenzoyl)hydrazide.

LCMS: MH$^+$ 370, retention time 2.84 minutes.

Intermediate 40: N-Cyclopropyl-4'-(hydrazinocarbonyl)-6-methyl-1,1'-biphenyl-3-carboxamide A solution of tert-butyl 2-({5'-[(cyclopropylamino)carbonyl]-2'-methyl-1,1'-biphenyl-4-yl}carbonyl)hydrazinecarboxylate (Intermediate 41) (2.37 g) in hydrogen chloride (4.0M solution in dioxane, 20 ml) was stirred at room temperature under nitrogen for 6 hours. The solvent was evaporated under vacuum, the residue was dissolved in water, basified with sodium hydroxide solution (2N) and extracted with ethyl acetate. The organic phase was dried (magnesium sulphate) and the solvent removed under vacuum to give the N-cyclopropyl-4'-(hydrazinocarbonyl)-6-methyl-1,1'-biphenyl-3-carboxamide.

LCMS: MH$^+$ 310, retention time 2.40 minutes.

Intermediate 41: tert-Butyl 2-({5'-[(cyclopropylamino)carbonyl]-2'-methyl-1,1'-biphenyl-4-yl}carbonyl)hydrazinecarboxylate 3'-[(Cyclopropylamino)carbonyl]-6'-methyl-1,1'-biphenyl-4-yl)carboxylic acid (1.7 g), tert-butylcarbazate (intermediate 42) (761 mg), HOBT (778 mg), DIPEA (1.2 ml) and EDC (1.33 g) were mixed in DMF (15 ml) and stirred at room temperature for 18 hours. The DMF was evaporated under vacuum, the residue dissolved in ethyl acetate and the solution washed with hydrochloric acid (0.5M, 2×20 ml) and aqueous sodiumhydrogen carbonate (2×20 ml). The organic phase was dried (magnesium sulphate), reduced to dryness under vacuum and purified on a biotage column (silica) eluting with ethyl acetate/cyclohexane (1:1) to give tert-butyl 2-({5'-[(cyclopropylamino)carbonyl]-2'-methyl-1,1'-biphenyl-4-yl}carbonyl)hydrazinecarboxylate.

LCMS: MH$^+$ 410, retention time 2.90 minutes.

Intermediate 42: 3'-[(Cyclopropylamino]carbonyl]-6'-methyl-1,1'-biphenyl-4-yl)carboxylic acid Methyl 3'-[(cyclopropylamino]carbonyl]-6'-methyl-1,1'-biphenyl-4-yl)carboxylate (Intermediate 43) (2.7 g, 8.7 mmol) and lithium hydroxide monohydrate (0.77 g, 18.3 mmol) were mixed in THF (20 ml) and water (10 ml) and heated at 80° C. for 2 h. The THF was evaporated under vacuum and hydrochloric acid (2N) added to the aqueous with vigorous stirring. The solid produced was filtered off, dissolved in methanol and absorbed onto silica. Purified by flash column chromatography eluting with DCM/ethanol/ammonia (20:8:1). The product fractions were concentrated under vacuum to give 3'-[(cyclopropylamino]carbonyl]-6'-methyl-1,1'-biphenyl-yl)carboxylic acid (2.0 g, 78%).

LCMS: MH$^+$ 296, retention time 2.94 minutes.

Intermediate 43: Methyl 3'-[(cyclopropylamino]carbonyl]-6'-methyl-1,1'-biphenyl-4-yl)carboxylate N-Cyclopropyl-3-iodo-4-methylbenzamide (4.7 g, 15.6 mmol), (4-methoxycarbonylphenyl) boronic acid (3.4 g, 18.7 mmol), aqueous sodium carbonate (1M, 50 ml) and tetrakis (triphenylphosphine)palladium (1.8 g, 0.156 mmol) in DME (100 ml) were heated at 95° C. for 18 h. The reaction mixture was absorbed onto silica and purified by flash column chromatography eluting with DCM/ethanol/ammonia (500:8:1). The product fractions were reduced to dryness under vacuum to give methyl 3'-[(cyclopropylamino]carbonyl]-6'-methyl-1,1'-biphenyl-4-yl)carboxylate (2.76 g, 57%).

LCMS: MH$^+$ 310, retention time 3.21 minutes.

Intermediate 44: 4'-[5-(Azidomethyl)-1,3,4-oxadiazol-2-yl]-N-cyclopropyl-6-methyl-1,1'-biphenyl-3-carboxamide A solution of sodium azide (14.8 mg) in water (1.25 ml) was added to 4'-[5-(chloromethyl)-1,3,4-oxadiazol-2-yl]-N-cyclopropyl-6-methyl-1,1'-biphenyl-3-carboxamide (Intermediate 45) (40 mg) in DMF (0.5 ml) and ethanol (2.5 ml) and the mixture heated at reflux for 2 hours. The solvents were evaporated under vacuum and the residue partitioned between water (20 ml) and chloroform (15 ml). The aqueous was extracted with chloroform (15 ml) and the combined organic phases dried (sodium sulphate) and reduced to dryness in vacuo to give 4'-[5-(azidomethyl)-1,3,4-oxadiazol-2-yl]-N-cyclopropyl-6-methyl-1,1'-biphenyl-3-carboxamide, LCMS: MH$^+$ 375, retention time 3.11 minutes.

Intermediate 45: 4'-[5-(Chloromethyl)-1,3,4-oxadiazol-2-yl]-N-cyclopropyl-6-methyl-1,1'-biphenyl-3-carboxamide N-Cyclopropyl-4'-(hydrazinocarbonyl)-6-methyl-1,1'-biphenyl-3-carboxamide (Intermediate 40) (150 mg) in 2-chloro-1,1,1-triethoxyethane (5 ml) was heated at 150° C. for 18 hours. The reaction was applied to a biotage cartridge (silica, 90 g) and eluted with an ethyl acetate/cyclohexane gradient. The product fractions were reduced to dryness under vacuum to give 4'-[5-(chloromethyl)-1,3,4-oxadiazol-2-yl]-N-cyclopropyl-6-methyl-1,1'-biphenyl-3-carboxamide.

LCMS: MH+ 368, retention time 3.15 minutes.

Intermediate 46: N-Cyclopropyl-4'-[(2-ethanimidoylhydrazino)carbonyl]-6-methyl-1,1'-biphenyl-3-carboxamide Sodium (7.5 mg) was dissolved in ethanol (3 ml), to this solution acetamidine hydrochloride (30.5 mg) was added and the reaction stirred at room temperature for 1.5 hours. The reaction was filtered and the filtrate added to a solution of N-cyclopropyl-4'-(hydrazinocarbonyl)-6-methyl-1,1'-biphenyl-3-carboxamide (Intermediate 40) (75 mg) in ethanol (1 ml). The reaction was stirred for 18 hours at room temperature and the ethanol evaporated under vacuum to give N-cyclopropyl-4'-[(2-ethanimidoylhydrazino)carbonyl]-6-methyl-1,1'-biphenyl-3-carboxamide.

LCMS: MH+ 351, retention time 2.13 minutes.

Intermediate 47: {5-[(Cyclopropylamino)carbonyl]-3-fluoro-2-methylphenyl}boronic acid N-Cyclopropyl-5-fluoro-3-iodo-4-methylbenzamide (Intermediate 48) (5 g) in THF (75 ml) was cooled to 0° C. and sodium hydride (60%, 1.23 g) added portionwise over 10 minutes. Once effervescence had ceased the reaction was cooled to −75° C. and n-butyl lithium (1.6M in hexanes, 20 ml) added over 25 minutes maintaining a temperature of ←70° C. Triisopropyl borate (8 ml) was added to the reaction over 10 minutes and the reaction stirred at −70° C. for 4 hours. The reaction was quenched with water (20 ml) and the mixture allowed to warm to 5° C. The reaction was concentrated under vacuum and the residue partitioned between saturated ammonium chloride and ethyl acetate. The organic phase was washed with saturated ammonium chloride, brine, dried (sodium sulphate) and reduced to dryness under vacuum. The residue was dissolved in DCM/ethyl acetate and purified by column chromatography on silica eluting with an ethyl acetate/DCM gradient (5-100% ethyl acetate) and then methanol. The product fractions were combined and the solvent evaporated under vacuum to give {5-[(cyclopropylamino)carbonyl]-3-fluoro-2-methylphenyl}boronic acid. LCMS MH+ 238, retention time 2.19 min.

Intermediate 48:
N-Cyclopropyl-5-fluoro-3-iodo-4-methylbenzamide

N-Iodosuccinimide (22.5 g) was added in portions to a solution of 3-fluoro-4-methylbenzoic acid (15.4 g) in trifluoromethanesulphonic acid (100 ml) at 0° C. over 3 hours and the reaction then allowed to warm to room temperature overnight. The reaction mixture was poured into ice/water (400 ml) and the precipitate filtered off and washed with water. The solid remaining was dissolved in ethyl acetate, washed with aqueous sodium thiosulphate (×2), then brine, dried (magnesium sulphate) and the solvent evaporated under vacuum. The residue was mixed with thionyl chloride (30 ml) and heated at 100° C. for 2.5 hours. The excess thionyl chloride was removed from the cooled reaction under vacuum and the residue dissolved in DCM (100 ml). Sodium carbonate (25 g) and cyclopropylamine (13 ml) were added to the solution and the reaction stirred at room temperature for 72 hours. The reaction was filtered and the residue washed with DCM and ethyl acetate. The solvent was evaporated from the combined filtrate and washings under vacuum. The residue was absorbed onto silica and chromatographed on a flash silica column eluting with an ethyl acetate/cyclohexane gradient (22-28% ethyl acetate). Appropriate fractions were reduced to dryness under vacuum to give N-cyclopropyl-5-fluoro-3-iodo-4-methylbenzamide.

LCMS; MH+ 320, retention time 3.16 minutes.

General Method A

The following method was used to prepare the Examples described below:

Tetrakis(triphenylphosphine)palladium(0) (20 mg) was added to the desired aromatic halide (0.147 mmol) and the desired boronic ester (0.147 mmol) dissolved in 1,2-dimethoxyethane (3 ml) and 10% w:v aqueous sodium carbonate (2 ml). The reaction was heated under nitrogen at 80° C. for 18 hours. The solvent was removed in vacuo. The crude material was purified by silica Biotage chromatography (10g), silica SPE cartridge or mass directed HPLC to give the desired product.

Example 1

4'-(2-Amino-4-thiazolyl)-6-methyl-N-[3-(4-morpholinyl)phenyl][1,1'-biphenyl]-3-carboxamide

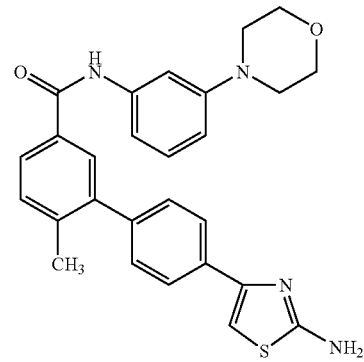

Example 1 was prepared using 4-(4-bromophenyl)-2-thiazolamine monohydrobromide and 4-methyl-N-[3-(4-morpholinyl)phenyl]-3-(4,4,5,5-tetramethyl-[1,3,2]dioxaborolan-2-yl)benzamide (Intermediate 5).

NMR: δH [$^2$H$_6$]—DMSO 10.09 (1H, s), 7.91 (2H, d), 7.88 (2H, m), 7.47 (1H, d), 7.43 (2H, d), 7.40 (1H, brs), 7.30 (1H, brd), 7.18 (1H, t), 7.09 (2H, brs), 6.70 (1H, dd), 3.74 (4H, apparent t), 3.09 (4H, apparent t), 2.34 (3H, s) ppm. LCMS: retention time 3.39 min MH+471.

Example 2

2',6-Dimethyl-4'-(5-methyl-1,3,4-oxadiazol-2-yl)-N-[3-(4-morpholinyl)phenyl][1,1'-biphenyl]-3-carboxamide

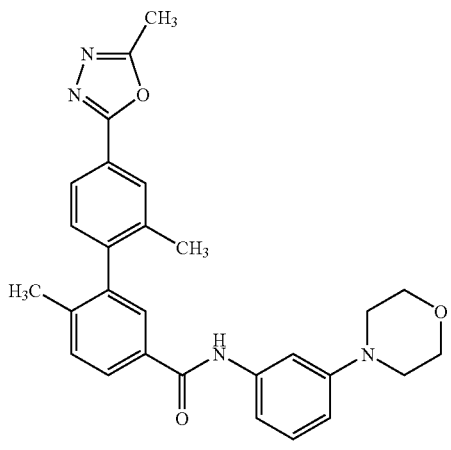

Example 2 was prepared using 2-(4-bromo-3-methylphenyl)-5-methyl-1,3,4-oxadiazole and 4-methyl-N-[3-(4-morpholinyl)phenyl]-3-(4,4,5,5-tetramethyl-[1,3,2]-dioxaborolan-2-yl)benzamide (Intermediate 5).

NMR: δH [$^2$H$_6$]—DMSO 10.05 (1H, s), 7.98 (1H, brs), 7.95 (1H, dd), 7.90 (1H, brd), 7.78 (1H, d), 7.51 (1H, d), 7.36 (2H, m), 7.30 (1H, brd), 7.18 (1H, t), 6.70 (1H, dd), 3.74 (4H, apparent t), 3.09 (4H, apparent t), 2.61 (3H,s), 2.13 (3H, s), 2.09 (3H, s) ppm.

LCMS: retention time 3.26 min MH$^+$469.

Example 3

6-Methyl-4'-(5-methyl-1,2,4-oxadiazol-3-yl)-N-[3-(4-morpholinyl)phenyl][1,1'-biphenyl]-3-carboxamide

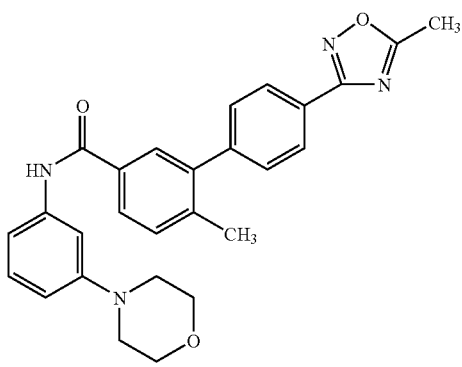

Example 3 was prepared using 3-(4-bromophenyl)-5-methyl-1,2,4oxadiazole and 4-methyl-N-[3-(4-morpholinyl)phenyl]-3-(4,4,5,5-tetramethyl-[1,3,2]-dioxaborolan-2-yl)benzamide (Intermediate 5).

NMR: δH [$^2$H$_6$]—DMSO 10.10 (1H, s), 8.11 (2H, d), 7.91 (1H, d), 7.90 (1H, s), 7.65 (2H, d), 7.50 (1H, d), 7.39 (1H, brs), 7.30 (1H, brd), 7.19 (1H, t), 6.71 (1H, dd), 3.74 (4H, apparent t), 3.09 (4H, apparent t), 2.70 (3H, s), 2.35 (3H, s) ppm.

LCMS: retention time 3.46 min MH$^+$455.

Example 4

4'-(1H-Imidazol-2-yl)-6-methyl-N-[3-(4-morpholinyl)phenyl][1,1'-biphenyl]-3-carboxamide

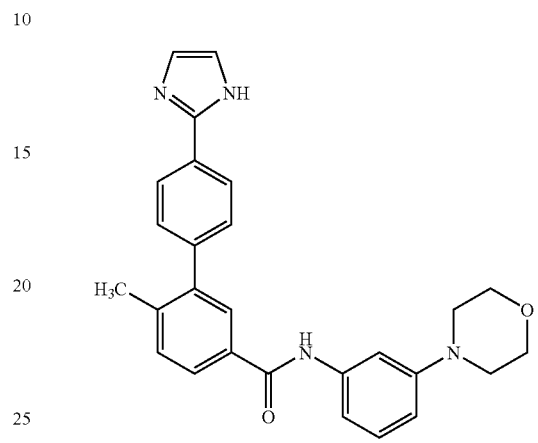

Example 4 was prepared using 2-(4-bromophenyl)-1H-imidazole and 4-methyl-N-[3-(4-morpholinyl)phenyl]-3-(4,4,5,5-tetramethyl-1,3,2-dioxaborolan-2-yl)benzamide (Intermediate 5).

NMR: δH [$^2$H$_6$]—DMSO 12.70 (1H, brs), 10.09 (1H, s), 8.05 (2H, d), 7.89 (2H, m), 7.51 (2H, d), 7.48 (1H, d), 7.40 (1H, brs), 7.30 (1H, brd), 7.19 (3H, apparent t), 6.71 (1H, dd), 3.74 (4H, apparent t), 3.09 (4H, apparent t), 2.35 (3H, s) ppm.

LCMS: retention time 2.47 min MH$^+$439.

Example 5

4'-(2-Amino-4-thiazolyl)-N-cyclopropyl-6-methyl[1,1'-biphenyl]-3-carboxamide

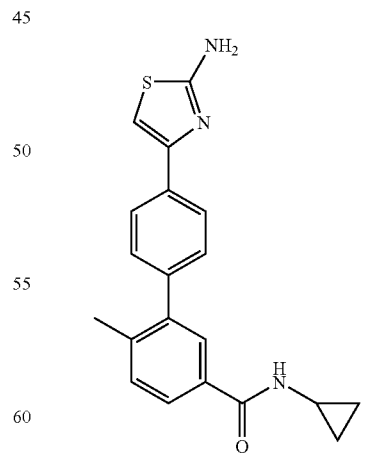

Example 5 was prepared using 4-(4-bromophenyl)-2-thiazolamine monohydrobromide and N-cyclopropyl-4-methyl-3-(4,4,5,5-tetramethyl-[1,3,2]-dioxaborolan-2-yl)benzamide (Intermediate 17).

NMR: δH [²H₆]—DMSO 8.42 (1H, s), 7.87 (2H, d), 7.74 (2H, dd), 7.7 (1H, d), 7.4 (2H, d), 7.38 (1H, d), 7.12 (1H, s), 2.85 (1H, m), 2.3 (3H, s), 0.67 (2H, m), 0.56 (2H, m) ppm. LCMS: retention time 2.99 min MH⁺ 350.

Example 6

N-Cyclopropyl-2',6-dimethyl-4'-(5-methyl-1,3,4-oxadiazol-2-yl)[1,1'-biphenyl]-3-carboxamide

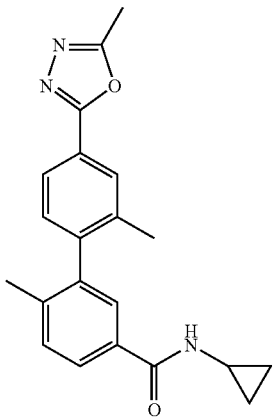

Example 6 was prepared using 2-(4-bromo-3-methylphenyl)-5-methyl-1,3,4-oxadiazole and N-cyclopropyl-4-methyl-3-(4,4,5,5-tetramethyl-[1,3,2]dioxaborolan-2-yl)benzamide (Intermediate 17).

NMR: δH [²H₆]—DMSO 8.43 (1H, d), 7.95 (1H, s), 7.85 (1H, dd), 7.8(1H, dd), 7.6 (1H, s), 7.4 (1H, d) 7.3 (1H, d), 2.85 (1H, m), 2.6 (3H, s), 2.1 (3H, s), 2.05 (3H, s), 0.67 (2H, m), 0.56 (2H, m) ppm. LCMS: retention time 2.93 min MH⁺348.

Example 7

N-Cyclopropyl-6-methyl-4'-(5-methyl-1,2,4-oxadiazol-3-yl)[1,1'-biphenyl]-3-carboxamide

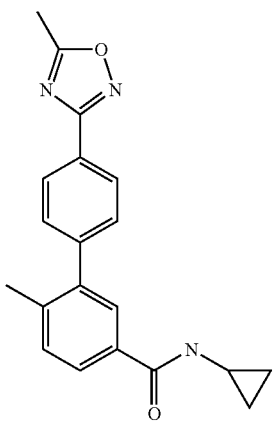

Example 7 was prepared using 3-(4-bromophenyl)-5-methyl-1,2,4-oxadiazole and N-cyclopropyl-4-methyl-3-(4,4,5,5-tetramethyl-[1,3,2]-dioxaborolan-2-yl)benzamide (Intermediate 17).

NMR: δH [²H₆]—DMSO 8.43 (1H, d), 8.10 (2H, d), 7.78 (1H, dd), 7.72(1H, d), 7.58 (2H, d), 7.4 (1H, d), 2.85 (1H, m), 2.7 (3H, s), 2.3 (3H, s), 0.67 (2H, m), 0.56 (2H, m) ppm. LCMS: retention time 3.24 min MH⁺334.

Example 8

N-Cyclopropyl-4'-(1H-imidazol-2-yl)-6-methyl-[1,1'-biphenyl]-3-carboxamide

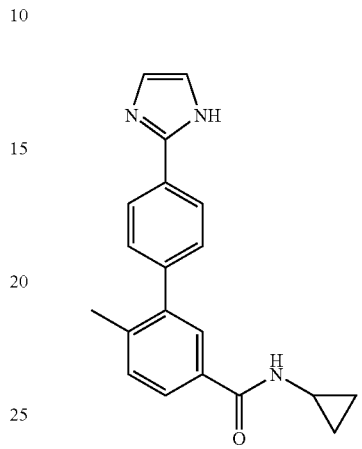

Example 8 was prepared using 2-(4-bromophenyl)-1H-imidazole and N-cyclopropyl-4-methyl-3-(4,4,5,5-tetramethyl-[1,3,2]-dioxaborolan-2-yl)benzamide (Intermediate 17).

NMR: δH [²H₆]—DMSO 12.6 (1H, s), 8.45 (1H, d), 8.05 (2H, d), 7.75 (1H, d), 7.7(1H, s), 7.45(2H, d), 7.4 (1H, d), 7.15 (bd, 2H), 2.85 (1H, m), 2.3 (3H, s), 0.67 (2H, m), 0.56 (2H, m) ppm. LCMS: retention time 2.17 min MH⁺318.

Example 9

N-[4'-(2-Amino-4-thiazolyl)-6-methyl-[1,1'-biphenyl]-3-yl]-2-(1-pyrrolidinyl)-4-pyridinecarboxamide

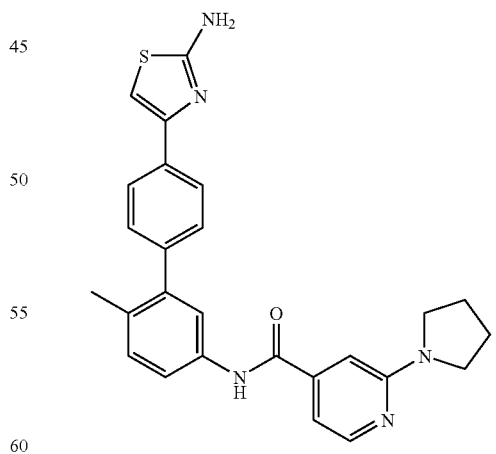

Example 9 was prepared using using 4-(4-bromophenyl)-2-thiazolamine monohydrobromide and N-[4-methyl-3-(4,4,5,5-tetramethyl-[1,3,2]-dioxaborolan-2-yl)phenyl]-2-(1-pyrrolidinyl)-4-pyridinecarboxamide (Intermediate 20).

NMR: δH [²H₆]—DMSO 10.3 (1H, s), 8.2 (1H, d), 7.85 (2H, d), 7.7 (1H, dd), 7.65(1H, d), 7.35(2H, d), 7.3 (1H, d), 7.1(2H,s), 7.05 (1H, s), 6.95 (1H, d), 6.85 (1H, s), 3.4 (4H, m), 2.25 (3H, s), 1.95 (4H, m)ppm. LCMS: retention time 2.68 min MH+456.

Example 10

N-[2',6-Dimethyl-4'-(5-methyl-1,3,4-oxadiazol-2-yl) [1,1'-biphenyl]-3-yl]-2-(1-pyrrolidinyl)-4-pyridinecarboxamide

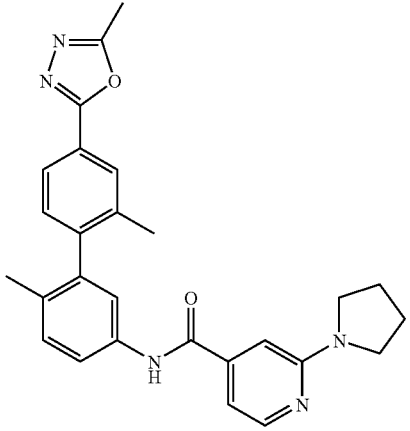

Example 10 was prepared using 2-(4-bromo-3-methylphenyl)-5-methyl-1,3,4-oxadiazole and N-[4-methyl-3-(4,4,5,5-tetramethyl-[1,3,2]-dioxaborolan-2-yl)phenyl]-2-(1-pyrrolidinyl)-4-pyridinecarboxamide (Intermediate 20).

NMR: δH [$^2$H$_6$]—DMSO 10.3 (1H, s), 8.2 (1H, d), 7.95 (1H, s), 7.85 (1H, d), 7.7 (1H, dd), 7.55(1H, d), 7.3(2H, dd), 6.95(1H, d), 6.85 (1H, s), 3.45 (4H, m), 2.6 (3H, s), 2.15 (3H, s), 2.0 (3H, s), 1.95 (4H, m)ppm. LCMS: retention time 2.71 min MH+454.

Example 11

N-[6-Methyl-4'-(5-methyl-1,2,4-oxadiazol-3-yl)[1,1'-biphenyl]-3-yl]-2-(1-pyrrolidinyl)-4-pyridinecarboxamide

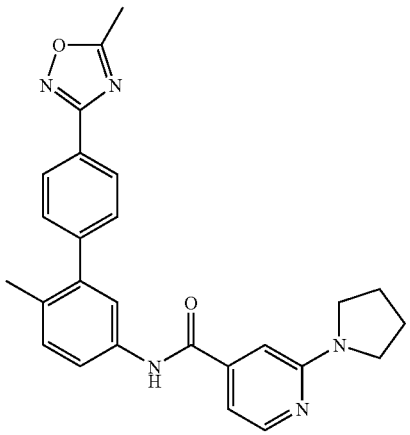

Example 11 was prepared using 3-(4-bromophenyl)-5-methyl-1,2,4-oxadiazole and N-[4-methyl-3-(4,4,5,5-tetramethyl-[1,3,2]-dioxaborolan-2-yl)phenyl]-2-(1-pyrrolidinyl)-4-pyridinecarboxamide (Intermediate 20).

NMR: δH [$^2$H$_6$]—DMSO 10.3 (1H, s), 8.2 (1H, d), 8.1 (2H, d), 7.75 (2H, m), 7.55(2H, d), 7.3 (1H, d), 6.95(1H, d), 6.85 (1H, s), 3.45 (4H, m), 2.7 (3H, s), 2.25 (3H, s), 1.95 (4H, m)ppm. LCMS: retention time 2.90 min MH+440.

Example 12

6-Methyl-4'-(5-pyrrolidin-1-ylmethyl-[1,3,4]oxadiazol-2-yl)-biphenyl-3-carboxylic acid cyclopropylamide

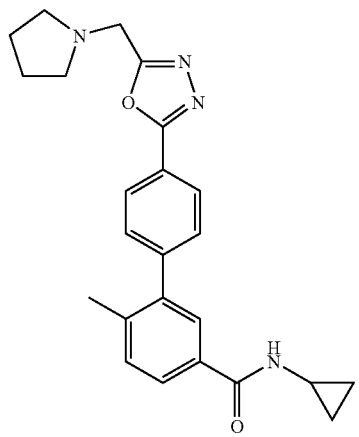

Example 12 was prepared from 2-(4-iodophenyl)-5-pyrrolidin-1-ylmethyl-[1,3,4]oxadiazole (Intermediate 8) and N-cyclopropyl-4-methyl-3-(4,4,5,5-tetramethyl-[1,3,2]-dioxaborolan-2-yl)benzamide (Intermediate 17).

NMR: δH [$^2$H$_6$]—DMSO 8.45 (1H,d), 8.09 (2H, d), 7.78 (1H, dd), 7.73 (1H, s), 7.62 (2H, d), 7.42 (1H, d), 3.98 (2H, brs), 2.85 (1H, m), 2.61 (4H, br), 2.30 (3H, s), 1.73 (4H, br), 0.69 (2H, m), 0.56 (2H, m) ppm. LCMS: retention time 2.28 min, MH+ 403.

Example 13

6-Methyl-4'-(5-piperidin-1-ylmethyl-[1,3,4]oxadiazol-2-yl)biphenyl-3-carboxylic acid cyclopropylamide

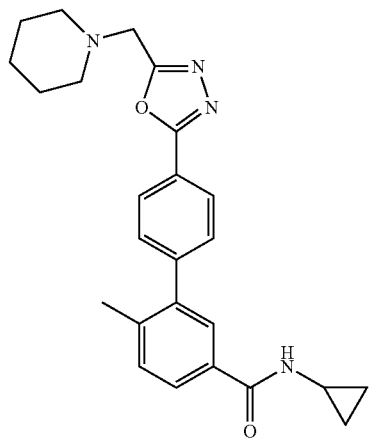

Example 13 was prepared from 1-[5-(4-iodophenyl)-[1,3,4]oxadiazol-2-ylmethyl]-piperidine (intermediate 9) and N-cyclopropyl-4-methyl-3-(4,4,5,5-tetramethyl-[1,3,2]-dioxaborolan-2-yl)benzamide (Intermediate 17).

NMR: δH [$^2$H$_6$]—DMSO 8.45 (1H,d), 8.09 (2H, d), 7.78 (1H, dd), 7.73 (1H, s), 7.63 (2H, d), 7.42 (1H, d), 3.87 (2H, brs), 2.84 (1H, m), 2.50 (4H, br), 2.30 (3H, s), 1.52 (4H, br), 1.38 (2H, br), 0.69 (2H, m), 0.56 (2H, m) ppm. LCMS: retention time 2.40 min, MH+ 417.

Example 14

6-Methyl-4'-(5-morpholin-4-ylmethyl-[1,3,4]oxadiazol-2-yl)-biphenyl-3-carboxylic acid cyclopropylamide

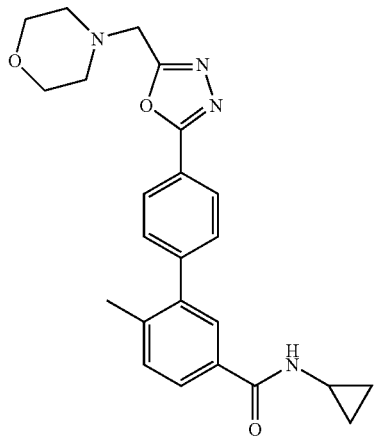

Example 14 was prepared from 4-[5-(4-iodophenyl)-[1,3,4]oxadiazol-2-ylmethyl]-morpholine (Intermediate 10) and N-cyclopropyl-4-methyl-3-(4,4,5,5-tetramethyl-[1,3,2]-dioxaborolan-2-yl)benzamide (Intermediate 17).

NMR: δH [$^2$H$_6$]—DMSO 8.46 (1H, d), 8.09 (2H, d), 7.77 (1H, dd), 7.73 (1H,s), 7.63 (2H, d), 7.42 (1H,d), 3.92 (2H, s), 3.61 (4H, t), 2.84 (1H, m), 2.55 (4H, br), 2.30 (3H, s), 0.69 (2H, m), 0.56 (2H, m) ppm. LCMS: retention time 2.70 min, MH+ 419.

Example 15

6-Methyl-4'-(5-methylaminomethyl-[1,3,4]oxadiazol-2-yl)biphenyl-3-carboxylic acid cyclopropylamide

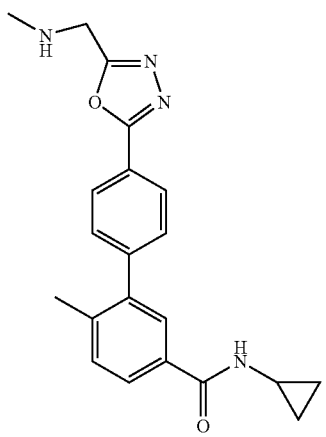

2-Chloromethyl-5-(4-iodophenyl)-[1,3,4]oxadiazole (Intermediate 7) (48 mg, 0.15 mmol) and potassium iodide (25 mg, 0.15 mmol) were dissolved in 2M methylamine in tetrahydrofuran (2 ml) and stirred for 18 hours at 20° C. The reaction was evaporated to dryness in vacuo and the product was purified on a 10 g silica SPE cartridge (stepped solvent gradient 80:20 ethyl acetate:cyclohexane, 100% ethyl acetate, 95:5 ethyl acetate:methanol). The resulting material was dissolved in 1,2 dimethoxyethane (4 ml) with tetrakis(triphenylphosphine)palladium(0) (16 mg, 0.014 mmol), N-cyclopropyl-4-methyl-3-(4,4,5,5-tetramethyl-[1,3,2]dioxaborolan-2-yl)-benzamide (Intermediate 17) (0.15 mmol) and 1M aqueous sodium carbonate (0.15 ml, 0.15 mmol). The reaction was heated under nitrogen at 80° C. for 18 hours. The solvent was removed in vacuo and the residue was purified by silica biotage chromatography eluting with 95:5 ethyl acetate:methanol.

NMR: δH [$^2$H$_6$]—DMSO 8.45 (1H,d), 8.09 (2H, d), 7.78 (1H, dd), 7.74 (1H, s), 7.63 (2H, d), 7.42 (1H, d), 3.96 (2H, s), 2.85 (1H, m), 2.35 (3H, s), 2.30 (3H, s), 0.69 (2H, m), 0.56 (2H, m) ppm. LCMS: retention time 2.20 min, MH+ 363.

Example 16

4'-(5-Dimethylaminomethyl-[1,3,4]oxadiazol-2-yl)-6-methyl-biphenyl-3-carboxylic acid cyclopropylamide

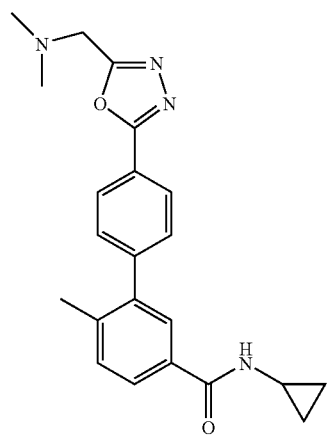

Example 16 was prepared from [5-(4-iodophenyl)-[1,3,4]oxadiazol-2-ylmethyl]-dimethylamine (Intermediate 11) and N-cyclopropyl-4-methyl-3-(4,4,5,5-tetramethyl-[1,3,2]-dioxaborolan-2-yl)benzamide (Intermediate 17).

NMR: δH [$^2$H$_6$]—DMSO 8.45 (1H,d), 8.09 (2H, d), 7.78 (1H, dd), 7.74 (1H, s), 7.63 (2H, d), 7.42 (1H, d), 3.89 (2H, s), 2.85 (1H, m), 2.32 (6H, s), 2.30 (3H, s), 0.69 (2H, m), 0.56 (2H, m) ppm. LCMS: retention time 2.27 min, MH+ 377.

Example 17

4'-{5-[(2-Hydroxy-1-hydroxymethyl-ethylamino)-methyl]-[1,3,4]oxadiazol-2-yl}-6-methyl-biphenyl-3-carboxylic acid cyclopropylamide

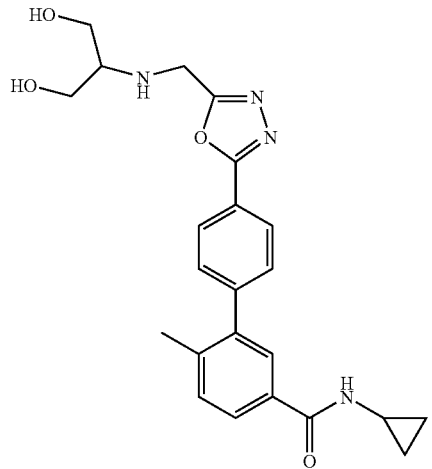

2-Chloromethyl-5-(4-iodophenyl)-[1,3,4]oxadiazole (Intermediate 7) (48 mg, 0.15 mmol), serinol (206 mg, 2.25 mmol) and potassium iodide (25 mg, 0.15 mmol) were dissolved in dimethylformamide (1 ml) and stirred for 18 hours at 20° C. The reaction was evaporated to dryness in vacuo and the product was flushed through a 10 g silica SPE cartridge, eluting with 95:5 ethyl acetate:methanol, to remove inorganic material. Without further purification the crude product was dissolved in 1,2 dimethoxyethane (4 ml). Tetrakis(triphenylphosphine)palladium(0) (16 mg, 0.014 mmol), N-cyclopropyl-4-methyl-3-(4,4,5,5-tetramethyl-[1,3,2]dioxaborolan-2-yl)-benzamide (Intermediate 17) (0.15 mmol) and 1M aqueous sodium carbonate (0.15 ml, 0.15 mmol) were added. The reaction was heated under nitrogen at 80° C. for 18 hours. Solvent was removed in vacuo and the residue was purified by mass-directed HPLC to yield the desired product.

NMR: δH [$^2$H$_6$]—DMSO 8.45 (1H,d), 8.09 (2H, d), 7.78 (1H, dd), 7.74 (1H, s), 7.63 (2H, d), 7.42 (1H, d), 4.51 (2H, t) 4.13 (2H, s), 3.42 (2H, m), 3.36 (2H, m), 2.85 (1H, m), 2.62 (1H, q), 2.30 (3H, s), 0.69 (2H, m), 0.56 (2H, m) ppm. LCMS: retention time 2.22 min, MH+ 423.

Example 18

6,2'-Dimethyl-4'-(5-methyl-[1,3,4]oxadiazol-2-yl)-biphenyl-3-carboxylic acid cyclopropylmethyl-amide

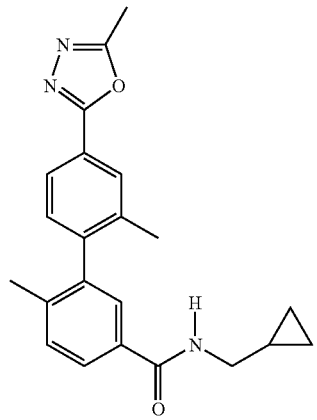

The title compound was prepared using 2-(4-bromo-3-methylphenyl)-5-methyl-[1,3,4]oxadiazole and N-cyclopropylmethyl-4-methyl-3-(4,4,5,5-tetramethyl-[1,3,2]-dioxaborolan-2-yl)benzamide (Intermediate 17).

NMR: δH—CD$_3$OD 8.55, (1H, t), 7.96, (1H, s), 7.85, (2H, m), 7.64, (1H, s), 7.43, (1H, d), 7.34, (1H, d), 3.11, (2H, m), 2.75, (3H, s), 2.10, (3H, s), 2.01, (3H, s), 1.01, (1H, m), 0.41, (2H, m), 0.21, (2H, m) ppm. LCMS: Retention time 3.19 mins MH+ 362.

Example 19

6,2'-Dimethyl-4'-(5-methyl-[1,3,4]oxadiazol-2-yl)-biphenyl-3-carboxylic acid thiazol-2-ylamide

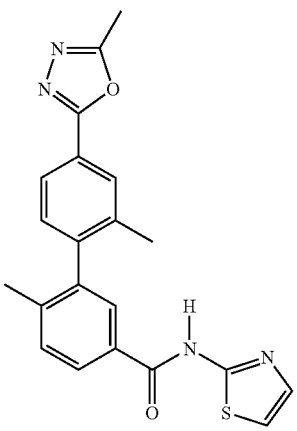

Example 19 was prepared using 2-(4-bromo-3-methylphenyl)-5-methyl-[1,3,4]oxadiazole and 4-methyl-3-(4,4,5,5-tetramethyl-[1,3,2]dioxaborolan-2-yl-N-(thiazol-2-yl)-benzamide (Intermediate 22).

NMR: δH—CD$_3$OD 12.65, (1H, s), 8.03, (1H, d), 7.97, (1H, s), 7.63, (2H, m), 7.58, (2H, m), 7.35, (1H, d), 7.24, (1H, d), 2.61, (3H, s), 2.13, (3H, s), 2.10, (3H, s) ppm.

LCMS: Retention time 3.23 mins MH+ 391.

Example 20

6,2'-Dimethyl-4'-(5-methyl-[1,3,4]oxadiazol-2-yl) biphenyl-3-carboxylic acid (3-methoxy-phenyl)-amide

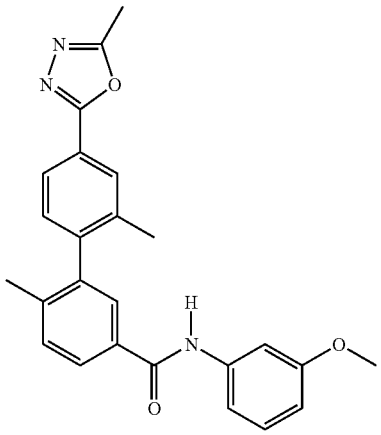

Example 20 was prepared using 2-(4-bromo-3-methylphenyl)-5-methyl-[1,3,4]oxadiazole and N-(3-methoxy-phenyl)-4-methyl-3-(4,4,5,5-tetramethyl-[1,3,2]dioxaborolan-2-yl)-benzamide (Intermediate 6).

NMR: δH—CD$_3$OD 10.15, (1H, s), 7.93, (3H, m), 7.78, (1H, d), 7.51, (1H, d), 7.45, (1H, s), 7.37, (2H, d), 7.23, (1H, t), 6.67, (1H, d), 3.74, (3H, s), 2.61, (3H, s), 2.13, (3H, s), 2.10, (3H, s) ppm. LCMS: Retention time 3.40 mins MH$^+$ 414.

Example 21

6,2'-Dimethyl-4'-(5-methyl-[1,3,4]oxadiazol-2-yl)-biphenyl-3-carboxylic acid[1,3,4]thiadiazol-2-ylamide

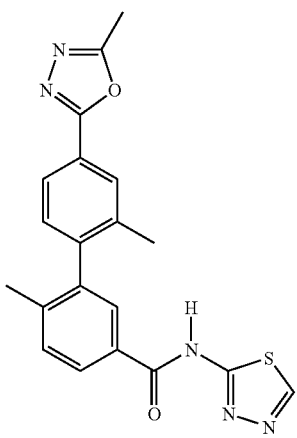

Example 21 was prepared using 2-(4-bromo-3-methylphenyl)-5-methyl-[1,3,4]oxadiazole and 4-methyl-3-(4,4,5,5,-tetramethyl-[1,3,2]dioxaborolan-2-yl)-N-([1,3,4]thiadiazol-2-yl)-benzamide (Intermediate 23).

NMR: δH—CD$_3$OD 9.22, (1H, s), 8.07, (1H, d), 7.98, (1H, s), 7.90, (2H, m), 7.57, (2H, m), 7.36, (1H, d), 2.61, (3H, s), 2.14, (3H, s), 2.12, (3H, s) ppm. LCMS: Retention time 3.11 MH$^+$ 392.

Example 22

Furan-3-carboxylic acid [6,2'-dimethyl-4'-(5-methyl-[1,3,4]oxadiazol-2-yl)biphenyl-3-yl]-amide

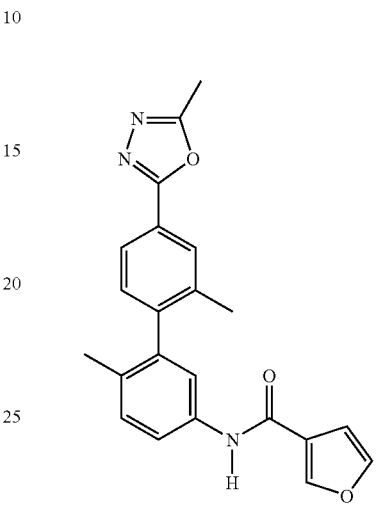

Example 22 was prepared using 2-(4-bromo-3-methylphenyl)-5-methyl-[1,3,4]oxadiazole and N-[4-methyl-3-(4,4,5,5,-tetramethyl-[1,3,2]dioxaborolan-2-yl)-phenyl]-3-furamide (Intermediate 25).

NMR: δH—CD$_3$OD 9.91, (1H, s), 8.35, (1H, s), 7.94, (1H, s), 7.87, (1H, d), 7.79, (1H, s), 7.67, (1H, d), 7.48, (1H, s), 7.32, (2H, m), 6.98, (1H, s), 2.60, (3H, s), 2.13, (3H, s), 1.99, (3H, s) ppm. LCMS: Retention time 3.21 mins MH$^+$ 374.

Example 23

Thiophene-3-carboxylic acid[6,2'-dimethyl-4'-(5-methyl-[1,3,4]oxadiazol-2-yl)-biphenyl-3-yl]-amide

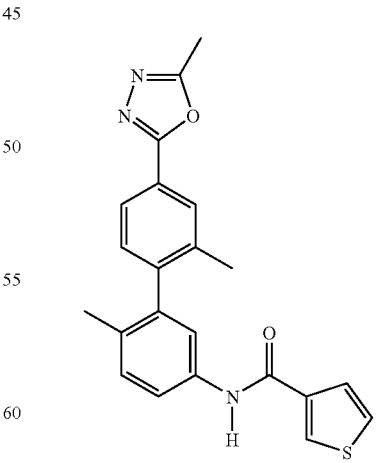

Example 23 was prepared using 2-(4-bromo-3-methylphenyl)-5-methyl-[1,3,4]oxadiazole and N-[4-methyl-3-(4,4,5,5,-tetramethyl-[1,3,2]dioxaborolan-2-yl)-phenyl]thiophene-3-amide (Intermediate 27).

NMR: δH—CD₃OD 10.04, (1H, s), 8.32, (1H, s), 7.95, (1H, s), 7.86, (1H, d), 7.71, (1H, d), 7.62, (2H, m), 7.53, (1H, s), 7.32, (2H, m), 2.60, (3H, s), 2.14, (3H, s), 1.99, (3H, s) ppm. LCMS: Retention time 3.33 mins MH⁺ 390.

Example 24

6-Methyl-4'(3-methyl-[1,2,4]oxadiazol-5-yl)-biphenyl-3-carboxylic acid cyclopropylamide

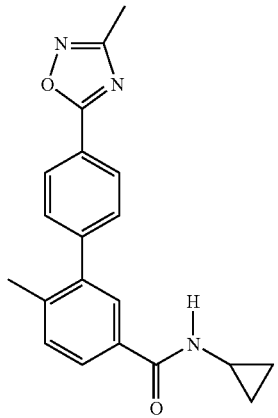

Example 24 was prepared using 5-(4-iodophenyl)-3-methyl-[1,2,4]oxadiazole (Intermediate 12) and N-cyclopropyl-4-methyl-3-(4,4,5,5-tetramethyl-1,3,2-dioxaborolan-2-yl) benzamide (Intermediate 17) using DMF as the solvent.

NMR: δH [²H₆]—DMSO 8.43, (1H, d), 8.17, (2H, d), 7.78, (1H, d), 7.73, (1H, s), 7.64, (2H, d), 7.41, (1H, d), 2.85-2.82, (1H, bm), 2.44, (3H, s), 2.29, (3H, s), 0.70-0.65, (2H, bm), 0.54, (2H, bm) ppm. LC/MS: Retention time 3.16 mins MH⁺ 334.

Example 25

Furan-3-carboxylic acid[6-methyl-4'-(3-methyl-[1,2,4]oxadiazol-5-yl)-biphenyl-3-yl]-amide

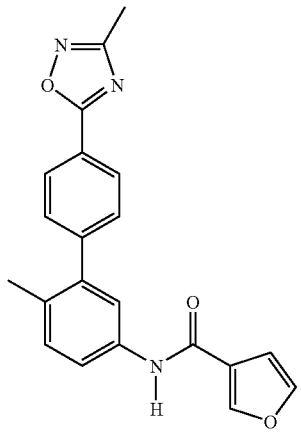

Example 25 was prepared using 5-(4-iodophenyl)-3-methyl-[1,2,4]oxadiazole (Intermediate 12) and N-[4-methyl-3-(4,4,5,5,-tetramethyl-[1,3,2]dioxaborolan-2-yl)-phenyl]-3-furamide (Intermediate 25) using DMF as the solvent.

NMR: δH [²H₆]—DMSO 9.94, (1H, s), 8.35, (1H, s), 8.16, (2H, d), 7.78, (1H, s), 7.70-7.61, (4H, bm), 7.30, (1H, d), 6.98, (1H, s), 2.43, (3H, s), 2.23, (3H, s) ppm.
LCMS: Retention time 3.45 mins MH⁺ 360.

Example 26

Thiophene-3-carboxylic acid[6-methyl-4'-(3-methyl-[1,2,4]oxadiazol-5-yl)-biphenyl-3-yl]-amide

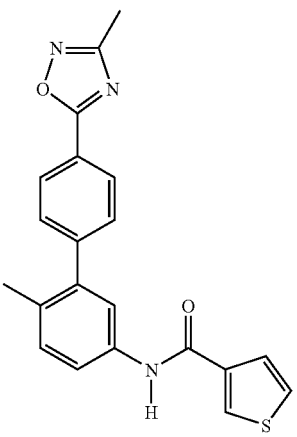

Example 26 was prepared using 5-(4-iodophenyl)-3-methyl-[1,2,4]oxadiazole (Intermediate 12) and N-[4-methyl-3-(4,4,5,5,-tetramethyl-[1,3,2]dioxaborolan-2-yl)-phenyl] thiophene-3-amide (Intermediate 27) using DMF as the solvent.

NMR: δH [²H₆]—DMSO 10.07, (1H, s), 8.33, (1H, s), 8.17, (2H, d), 7.73-7.61, (6H, bm), 7.32-7.29, (1H, bd), 2.43, (3H, s), 2.22, (3H, s) ppm. LCMS: Retention time 3.64 mins MH⁺ 376.

Example 27

6-Methyl-4'(3-methyl-[1,2,4]oxadiazol-5-yl)biphenyl-3-carboxylic acid [1,3,4]thiadiazol-2-ylamide

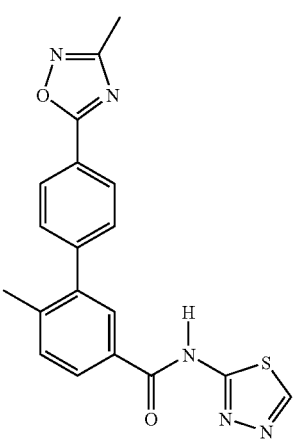

Example 27 was prepared using 5-(4-iodophenyl)-3-methyl-[1,2,4]oxadiazole (Intermediate 12) and 4-methyl-3-(4, 4,5,5,-tetramethyl-[1,3,2]dioxaborolan-2-yl)-N-([1,3,4]thiadiazol-2-yl)-benzamide (Intermediate 23) using DMF as the solvent.

NMR: δH [$^2$H$_6$]—DMSO 13.11, (1H, s), 9.22, (1H, s), 8.20, (2H, d), 8.10, (1H, s), 8.04, (1H, d), 7.73, (2H, d), 7.54, (1H, d), 2.44, (3H, s), 2.37, (3H, s) ppm. LCMS: Retention time 3.35 mins MH$^+$ 378.

Example 28

6-Methyl-4'(3-methyl-[1,2,4]oxadiazol-5-yl)-biphenyl-3-carboxylic acid (3-morpholin-4-phenyl)-amide

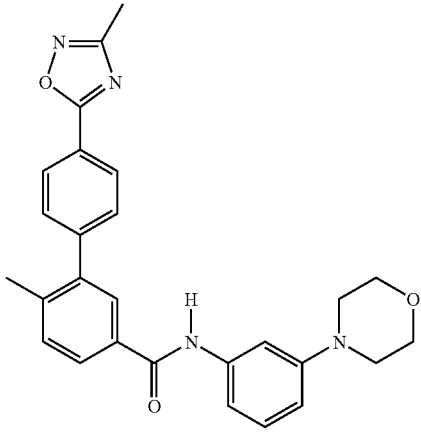

Example 28 was prepared using 5-(4-iodophenyl)-3-methyl-[1,2,4]oxadiazole (Intermediate 12) and 4-methyl-N-(3-morpholin-4-yl-phenyl)-3-(4,4,5,5-tetramethyl-[1,3,2]dioxaborolan-2-yl)-benzamide (Intermediate 5) with propan-2-ol as the solvent.

NMR: δH [$^2$H$_6$]—DMSO 10.08, (1H, s), 8.19, (2H, d), 7.92, (1H, d), 7.89, (1H, s), 7.70, (2H, d), 7.50, (1H, d), 7.38, (1H, s), 7.28, (1H, d), 7.17, (1H, t), 6.70, (1H, s), 3.73, (4H, t), 3.07, (4H, t), 2.44, (3H, s), 2.34, (3H, s) ppm. LCMS: Retention time 3.50 mins MH$^+$ 455.

Example 29

6,2'-Dimethyl-4'-(5-methyl-[1,2,4]oxadiazol-3-yl)-biphenyl-3-carboxylic acid cyclopropylamide

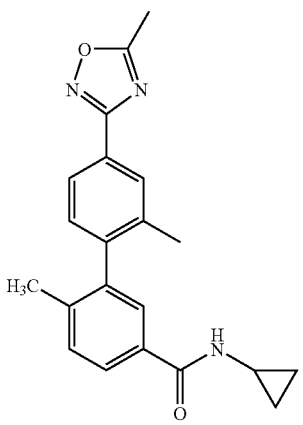

Example 29 was prepared using 3-(4-bromo-3-methylphenyl)-5-methyl-[1,2,4]oxadiazole and N-cyclopropyl-4-methyl-3-(4,4,5,5-tetramethyl-[1,3,2]dioxaborolan-2-yl)-benzamide (Intermediate 17) using DMF as the solvent.

NMR: δH [$^2$H$_6$]—DMSO 8.36, (1H, d), 7.95, (1H, s), 7.86, (1H, d), 7.76, (1H, d), 7.58, (1H, s), 7.39, (1H, d), 7.27, (1H, d), 2.81, (1H, m), 2.67, (3H, s), 2.05, (6H, br), 0.65, (2H, m), 0.54, (2H, m) ppm. LCMS: Retention time 3.22 mins MH$^+$ 348.

Example 30

Furan-3-carboxylic acid[6,2'-dimethyl-4'-(5-methyl-[1,2,4]oxadiazol-3-yl)-biphenyl-3-yl]-amide

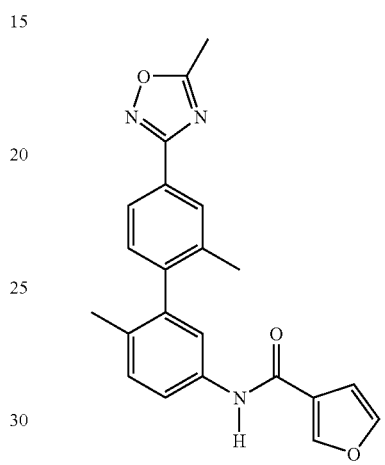

Example 30 was prepared using 3-(4-bromo-3-methylphenyl)-5-methyl-[1,2,4]oxadiazole and N-[4-methyl-3-(4,4,5,5,-tetramethyl-[1,3,2]dioxaborolan-2-yl)-phenyl]-3-furamide (Intermediate 25) using DMF as the solvent.

NMR: δH [$^2$H$_6$]—DMSO 9.89, (1H, s), 8.34, (1H, s), 7.95, (1H, s), 7.88, (1H, d), 7.77, (1H, s), 7.67, (1H, d), 7.46, (1H, s), 7.28, (2H, t), 6.96, (1H, s), 2.67, (3H, s), 2.11, (3H, s), 1.98, (3H, s) ppm. LCMS: Retention time 3.55 mins MH$^+$ 374.

Example 31

Thiophene-3-carboxylic acid[6,2'-dimethyl-4'-(5-methyl-[1,2,4]oxadiazol-3-yl)biphenyl-3-yl]-amide

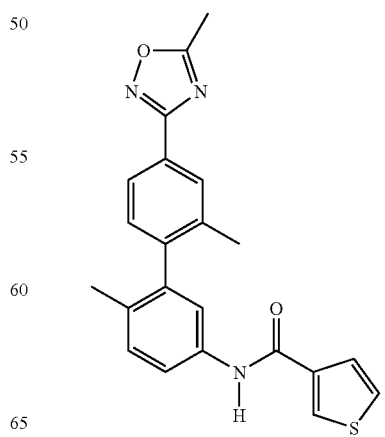

Example 31 was prepared using 3-(4-bromo-3-methylphenyl)-5-methyl-[1,2,4]oxadiazole and N-[4methyl-3-(4,4,5,5,-tetramethyl-[1,3,2]dioxaborolan-2-yl)-phenyl]thiophene-3-amide (Intermediate 27) using DMF as the solvent.

NMR: δH [²H₆]—DMSO 10.03, (1H, s), 8.31, (1H, s), 7.95, (1H, s), 7.87, (1H, d), 7.69, (1H, d), 7.64-7.59, (2H, m), 7.52, (1H, d), 7.30-7.27, (2H, m), 2.67, (3H, s), 2.12, (3H, s), 1.98, (3H, s) ppm. LCMS: Retention time 3.67 mins MH⁺ 390.

Example 32

6,2'-Dimethyl-4'-(5-methyl-[1,2,4]oxadiazol-3-yl)-biphenyl-3-carboxylic acid (3-morpholin-4-yl-phenyl)amide

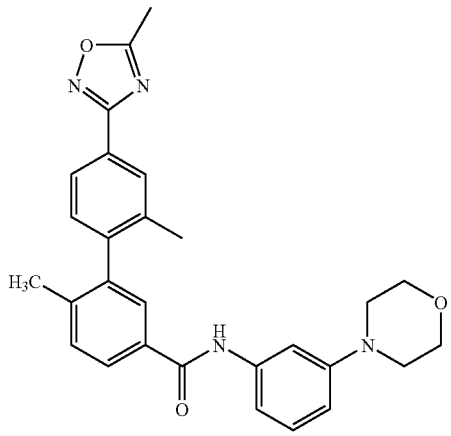

Example 32 was prepared using 3-(4-bromo-3-methylphenyl)-5-methyl-[1,2,4]oxadiazole and 4-methyl-N-(3-morpholin-4-yl-phenyl)-3-(4,4,5,5-tetramethyl-[1,3,2]dioxaborolan-2-yl)-benzamide (Intermediate 5) with propan-2-ol as the solvent.

NMR: δH [²H₆]—DMSO 10.01, (1H, s), 7.98, (1H, s), 7.93-7.89, (2H, m), 7.77, (1H, s), 7.49, (1H, d), 7.36, (1H, s), 7.34-7.28, (2H, m), 7.17, (1H, t), 6.69, (1H, d), 3.73, (4H, t), 3.07, (4H, t), 2.68, (3H, s), 2.11, (3H, s), 2.09, (3H, s) ppm. LCMS: Retention time 3.60 mins MH⁺ 469.

Example 33

6-Methyl-4'-(5-methyl-[1,3,4]oxadiazol-2-yl)-biphenyl-3-carboxylic acid[1,3,4]thiadiazol-2-ylamide

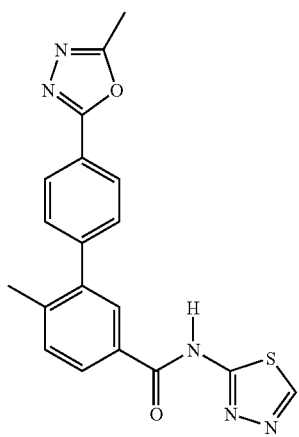

Example 33 was prepared using 2-(4-iodophenyl)-5-methyl-[1,3,4]oxadiazole (Intermediate 15) and 4-methyl-3-4,4,5,5,-tetramethyl-[1,3,2]dioxaborolan-2-yl)-N-([1,3,4]thiadiazol-2-yl)-benzamide (Intermediate 23) with propan-2-ol as the solvent.

NMR: δH [²H₆]—DMSO 9.24, (1H, s), 8.06, (4H,bm), 7.71, (2H, d), 7.55, (2H, d), 2.62, (3H, s), 2.38, (3H, s) ppm. LCMS: Retention time 3.03 mins MH⁺ 378.

Example 34

Thiophene-3-carboxylic acid[6-methyl-4'-(5-methyl-[1,3,4]oxadiazol-2-yl)-biphenyl-3-yl]-amide

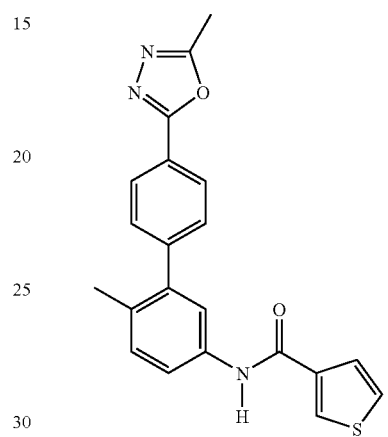

Example 34 was prepared using 2-(4-iodophenyl)-5-methyl-[1,3,4]oxadiazole (Intermediate 15) and N-[4-methyl-3-(4,4,5,5,-tetramethyl-[1,3,2]dioxaborolan-2-yl)-phenyl]thiophene-3-amide (Intermediate 27) with propan-2-ol as the solvent.

NMR: δH [²H₆]—DMSO 10.08, (1H, s), 8.34, (1H, s),8.06, (2H, m), 7.65, (6H, bm) 7.31, (1H, s), 2.61, (3H, s), 2.24, (3H, s) ppm. LCMS: Retention time 3.35 mins MH⁺ 376.

Example 35

Furan-3-carboxylic acid[6-methyl-4'-(5-methyl-[1,3,4]oxadiazol-2-yl)-biphenyl-3-yl]-amide

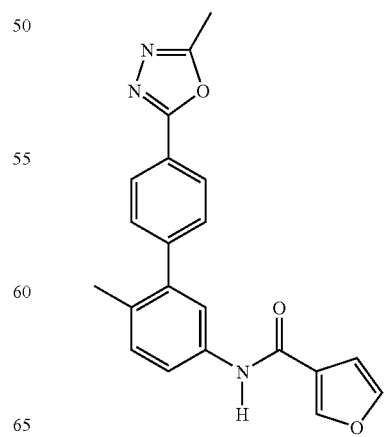

Example 35 was prepared using 2-(4iodophenyl)-5-methyl-[1,3,4]oxadiazole (Intermediate 15) and N-[4-methyl-3-(4,4,5,5,-tetramethyl-[1,3,2]dioxaborolan-2-yl)-phenyl]-3-furamide (Intermediate 25) with propan-2-ol as the solvent.

NMR: δH [$^2$H$_6$]—DMSO 9.94, (1H, s), 8.37, (1H, s), 8.06, (2H, d), 7.79, (1H, s), 7.76-7.68, (1H, m), 7.65, (1H, s), 7.59, (2H, d), 7.31, (1H, d), 6.99, (1H, s), 2.60, (3H, s), 2.22, (3H, s) ppm. LCMS: Retention time 3.21 mins MH$^+$ 360.

Example 36

6-Methyl-4'-(5-methyl-[1,3,4]oxadiazol-2-yl)-biphenyl-3-carboxylic acid (3-morpholin-4yl-phenyl)-amide

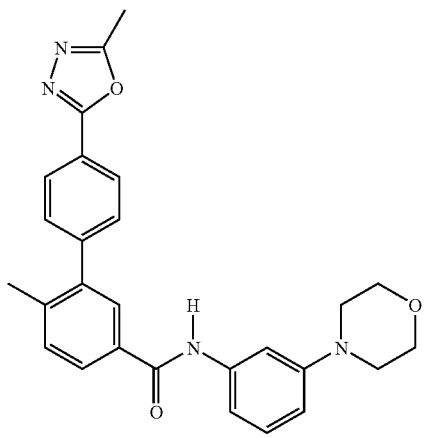

Example 36 was prepared using 2-(4-iodophenyl)-5-methyl-[1,3,4]oxadiazole (Intermediate 15) and 4-methyl-N-(3-morpholin-4-phenyl)-3-(4,4,5,5-tetramethyl-[1,3,2]dioxaborolan-2-yl)-benzamide (Intermediate 5) with propan-2-ol as the solvent.

NMR: δH [$^2$H$_6$]—DMSO 10.08, (1H, s), 8.07, (2H, d), 7.90, (2H, m), 7.66, (2H, d), 7.49, (1H, d), 7.38, (1H, s), 7.27, (1H, d), 7.17, (1H, t), 6.70, (1H, d), 3.73, (4H, t), 3.07, (4H, t), 2.60, (3H, s), 2.33, (3H, s) ppm. LCMS: Retention time 3.29 mins MH$^+$ 455.

Example 37

6-Methyl-4'-(5-methyl-[1,3,4]oxadiazol-2-yl)-biphenyl-3-carboxylic acid (3-methoxy-phenyl)-amide

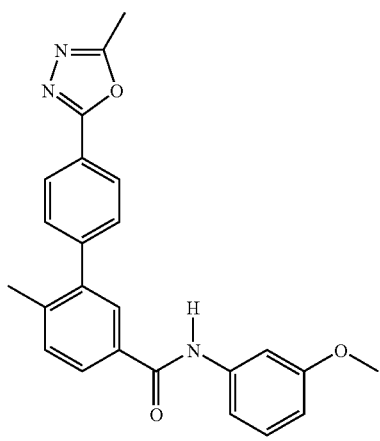

Example 37 was prepared using 2-(4iodophenyl)-5-methyl-[1,3,4]oxadiazole (Intermediate 15) and N-3-methoxyphenyl)-4-methyl-3-(4,4,5,5-tetramethyl-[1,3,2]dioxaborolan-2-yl)-benzamide (Intermediate 6) with propan-2-ol as the solvent.

NMR: δH [$^2$H$_6$]—DMSO 10.19, (1H, s), 8.07, (2H, d), 7.90, (2H, m), 7.66, (2H, d), 7.50, (1H, d), 7.45, (1H, s), 7.36, (1H, d), 7.23, (1H, t), 6.67, (1H, d), 3.74, (3H, s), 2.60, (3H, s), 2.34, (3H, s) ppm. LCMS: Retention time 3.39 mins MH$^+$ 400.

Example 38

6-Methyl-4'-(5-methyl-[1,3,4]oxadiazol-2-yl)biphenyl-3-carboxylic acid thiazol-2-ylamide

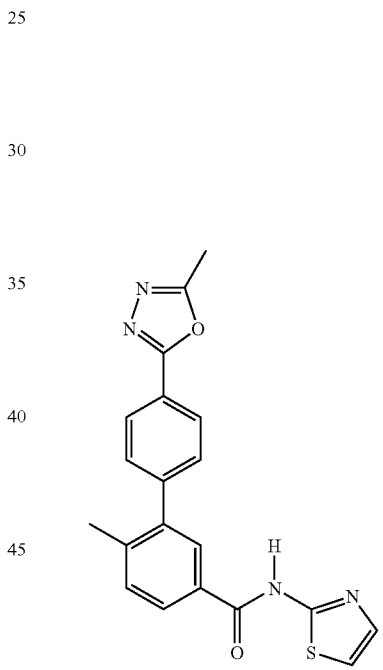

Example 38 was prepared using 2-(4-iodophenyl)-5-methyl-[1,3,4]oxadiazole (Intermediate 15) and 4-methyl-3-(4,4,5,5-tetramethyl-[1,3,2]dioxaborolan-2-yl-N-(thiazol-2-yl)-benzamide (Intermediate 22) with propan-2-ol as the solvent.

NMR: δH [$^2$H$_6$]—DMSO 12.69, (1H, s), 8.07, (3H, m), 8.01, (1H, d), 7.69, (2H, d), 7.55, (1H, d), 7.51, (1H, d), 7.28, (1H, d), 2.61, (3H, s), 2.36, (3H, s) ppm. LCMS: Retention time 3.16 mins MH$^+$ 377.

Example 39

6-Methyl-4'-(5-methyl-[1,3,4]oxadiazol-2-yl)-biphenyl-3-carboxylic acid cyclopropylamide

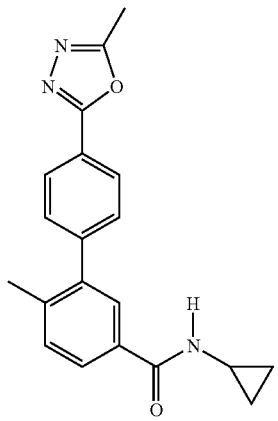

Example 39 was prepared using 2-(4-iodophenyl)-5-methyl-[1,3,4]oxadiazole (Intermediate 15) and N-cyclopropyl-4methyl-3-(4,4,5,5-tetramethyl-[1,3,2]dioxaborolan-2-yl)-benzamide (Intermediate 17) with propan-2-ol as the solvent.

NMR: $\delta$H [$^2$H$_6$]—DMSO 8.44, (1H, d), 8.05, (2H, d), 7.77, (1H, d), 7.72, (1H, s), 7.60, (2H, d), 7.40, (1H, d), 2.83, (1H, m), 2.60, (3H, s), 2.29, (3H, s), 0.68-0.65, (2H, m), 0.57-0.53, (2H, m) ppm. LCMS: Retention time 2.86 mins MH$^+$ 334.

Example 40

6-Methyl-4'-(5-methyl-[1,3,4]oxadiazol-2-yl-biphenyl-3-carboxylic acid cyclopropylmethylamide

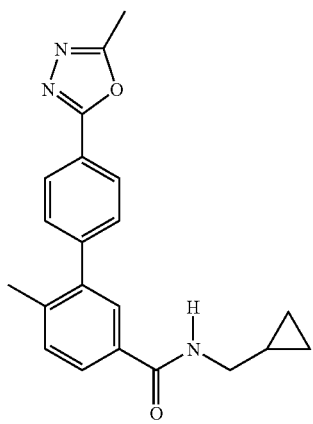

Example 40 was prepared using 2-(4-iodophenyl)-5-methyl-[1,3,4]oxadiazole (Intermediate 15) and N-cyclopropylmethyl-4-methyl-3-(4,4,5,5-tetramethyl-[1,3,2]dioxaborolan-2-yl)-benzamide (intermediate 28) with propan-2-ol as the solvent.

NMR: $\delta$H [$^2$H$_6$]—DMSO 8.59, (1H, t), 8.07, (2H, d), 7.80, (1H, d), 7.77, (1H, s), 7.62, (2H, d), 7.42, (1H, d), 3.12, (2H, m), 2.60, (3H, s), 2.30, (3H, s), 1.01, (1H, m), 0.43-0.39, (2H, m), 0.22-0.19, (2H, m) ppm. LCMS: Retention time 3.03 mins MH$^+$ 348.

Example 41

4'-(5-Amino-1,3,4-oxadiazol-2-yl)-N-cyclopropyl-5fluoro-6-methyl-1,1'-biphenyl-3-carboxamide

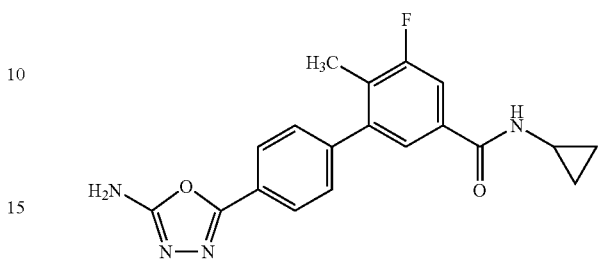

N-Cyclopropyl-5-fluoro-4'-(hydrazinocarbonyl)-6-methyl-1,1'-biphenyl-3-carboxamide (Intermediate 29) (150 mg) and a mixture of di(benzotriazolyl)methanimines (121 mg, Synthesis 6, 2001, 897-903) were dissolved in THF (10 ml) and the solution heated at reflux for 6 hours. The cooled reaction was absorbed onto silica and applied to a silica biotage column (40 g) and eluted with an ethyl acetate/cyclohexane gradient (50-100% ethyl acetate). The product fractions were combined and evaporated to dryness to give 4'-(5-amino-1,3,4-oxadiazol-2-yl)-N-cyclopropyl-5-fluoro-6-methyl-1,1'-biphenyl-3-carboxamide.

NMR: $\delta$H [$^2$H$_6$]—DMSO 8.53, (1H, d), 7.90, (2H, d), 7.65-7.55, (4H, m), 7.31, (2H, b), 2.85, (1H, m), 2.20, (3H, d), 0.70, (2H, m), 0.57, (2H, m). LCMS: MH$^+$ 353, retention time 2.80 minutes.

Example 42

N-Cyclopropyl-5-fluoro-4'-[5-(methoxymethyl)-1,3,4-oxadiazol-2-yl]-6-methyl-1,1'-biphenyl-3-carboxamide

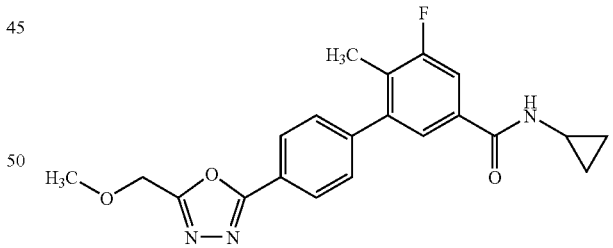

Freshly prepared sodium methoxide in methanol (0.2M, 0.8 ml) was added to a solution of (4'-[5-chloromethyl)-1,3,4-oxadiazol-2-yl]-N-cyclopropyl-5-fluoro-6-methyl-1,1'-biphenyl-3-carboxamide (Intermediate 34) (50 mg) in methanol (1 ml) and the reaction stirred at room temperature for 18 hours. Further sodium methoxide in methanol (0.2M, 1.6 ml) was added and the reaction continued for 72 hours. The reaction was reduced to dryness under vacuum and the residue partitioned between ethyl acetate and water. The organic phase was reduced to dryness and loaded onto a bond-elut (silica, 10 g). Eluted with an ethyl acetate/cyclohexane gradient. The solvent was evaporated from the product fractions under vacuum to give N-cyclopropyl-5-fluoro4'-[5-(methoxymethyl)-1,3,4-oxadiazol-2-yl]-6-methyl-1,1'-biphenyl-3-carboxamide.

NMR: δH [$^2$H$_6$]—DMSO 8.55, (1H, d), 8.12, (2H, d), 7.65, (4H, m), 4.76, (2H, s), 3.41, (3H, s), 2.86, (1H, m), 2.20(3H, d), 0.70(2H, m), 0.57(2H, m). LCMS: MH$^+$ 382, retention time 3.01 minutes.

Example 43

N-Cyclopropyl-4'-{5-[(cyclopropylamino)methyl]-1,3,4-oxadiazol-2-yl}-5-fluoro-6-methyl-1,1'-biphenyl-3-carboxamide

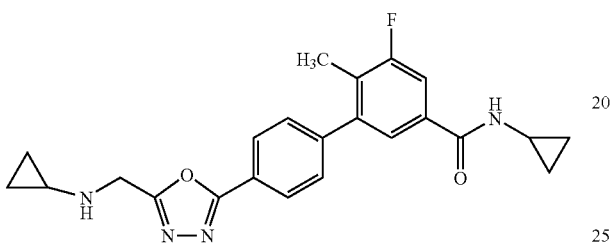

4'-[5-(Chloromethyl)-1,3,4-oxadiazol-2-yl]-N-cyclopropyl-5-fluoro-6-methyl-1,1'-biphenyl-3-carboxamide (Intermediate 34) (50 mg) and potassium iodide (22 mg) were stirred in cyclopropylamine (2 ml) for 48 hours. The reaction was absorbed onto silica and purified by chromatography on a biotage column (silica, 9 g), eluting with DCM/methanol (99:1). The product fractions were reduced to dryness under vacuum to give N-cyclopropyl-4'-{5-[(cyclopropylamino)methyl]-1,3,4-oxadiazol-2-yl}-5-fluoro-6-methyl-1,1'-biphenyl-3-carboxamide.

NMR: δH [$^2$H$_6$]—DMSO 8.55, (1H, d), 8.11, (2H,d), 7.65 (4H, m), 4.04(2H, d), 3.14, (1H, m), 2.86, (1H, m), 2.20, (3H, d), 0.70(2H, m), 0.57(2H, m), 0.39, (2H, m), 0.26, (2H, m). LCMS: MH$^+$ 407, retention time 2.56 minutes.

Example 44

N-Cyclopropyl-4'-[5-(ethoxymethyl)-1,3,4-oxadiazol-2-yl]-5-fluoro-6-methyl-1,1'-biphenyl-3-carboxamide

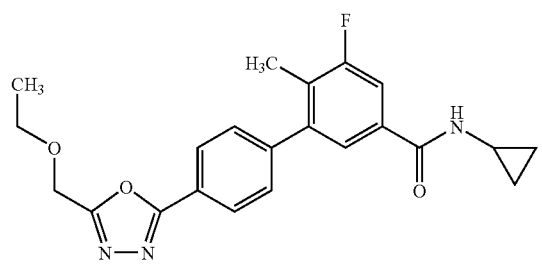

Freshly prepared sodium ethoxide in ethanol (0.2M, 0.8 ml) was added to a solution of (4'-[5-(chloromethyl)-1,3,4-oxadiazol-2-yl]-N-cyclopropyl-5-fluoro-6-methyl-1,1'-biphenyl-3-carboxamide (Intermediate 34) (50 mg) in ethanol (1 ml) and the reaction stirred at room temperature for 18 hours. The reaction was reduced to dryness under vacuum and the residue partitioned between ethyl acetate and water. The organic phase dried (magnesium sulphate) and reduced to dryness under vacuum. The residue was purified by HPLC to give N-cyclopropyl-4'-[5-ethoxymethyl)-1,3,4-oxadiazol-2-yl]-5-fluoro-6-methyl-1,1'-biphenyl-3-carboxamide.

NMR: δH [$^2$H$_6$]—DMSO 8.56, (1H, d), 8.12(2H, d), 7.65 (4H, m), 4.79(2H, s), 3.62, (2H, q), 2.86, (1H, m), 2.20, (3H, d), 1.17(3H, t), 0.70(2H, m), 0.57, (2H, m). LCMS: MH$^+$396, retention time 3.17 minutes.

Example 45

4'-[5-(Aminomethyl)-1,3,4-oxadiazol-2-yl]-N-cyclopropyl-5-fluoro-6-methyl-1,1'-biphenyl-3-carboxamide

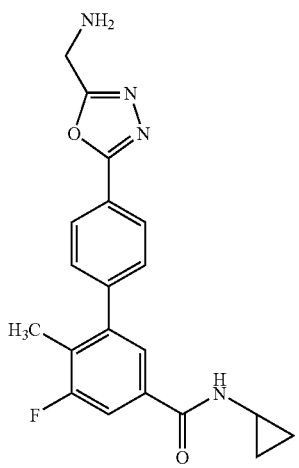

4'-[5-(Azidomethyl)-1,3,4oxadiazol-2-yl]-N-cyclopropyl-5-fluoro-6-methyl-1,1'-biphenyl-3-carboxamide (Intermediate 35) (208 mg) and palladium on carbon (10% w/w, 21 mg) in ethanol (10 ml) were hydrogenated under 1 Atm. of hydrogen for 24 hours at room temperature. The reaction was filtered through celite and the filtrate reduced to dryness under vacuum. The residue was applied to a bond-elut (silica, 10 g) and eluted with an ethyl acetate/cyclohexane gradient (50-100% ethyl acetate) and then with methanol in ethyl acetate (0-50%). The solvent was evaporated from the product fractions under vacuum to give 4'-[5-(aminomethyl)-1,3,4oxadiazol-2-yl]-N-cyclopropyl-5-fluoro-6-methyl-1,1'-biphenyl-3-carboxamide.

NMR: δH CDCl$_3$ 8.12, (2H, d), 7.49-7.42, (4H, m), 6.36 (1H, b), 4.18(2H, s), 2.90, (1H, m), 2.22, (3H, d), 0.88, (2H, m), 0.63, (2H, m). LCMS: MH$^+$367, retention time 2.22 minutes.

Example 46

N-Cyclopropyl-5-fluoro-4'-[5-(hydroxymethyl)-1,3,4-oxadiazol-2-yl]-6-methyl-1,1'-biphenyl-3-carboxamide

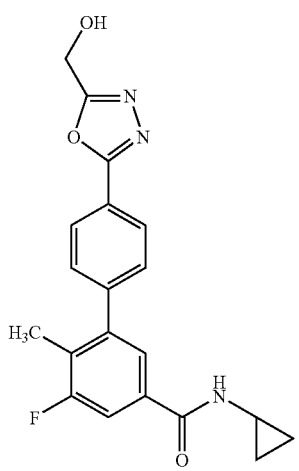

A solution of 4'-[5-(aminomethyl)-1,3,4-oxadiazol-2-yl]-N-cyclopropyl-5-fluoro-6-methyl-1,1'-biphenyl-3-carboxamide (Example 45) (96 mg) in acetic acid/water (1:1 v/v, 7 ml) was cooled to 0° C. Sodium nitrite (206 mg) was added and the solution stirred for 30 minutes at 0° C. and then for a further 16 hours at room temperature. Concentrated sodium hydroxide solution (10 ml) was added to the reaction and the mixture extracted with ether (3×40 ml) and then chloroform (40 ml). The organic phases were combined, dried and reduced to dryness under vacuum. The residue was dissolved in 5% potassium hydroxide in methanol and stirred at room temperature for 90 minutes. The methanol was removed in vacuo, the residue partitioned between ethyl acetate/chloroform (1:1)/water and the organic phase dried and reduced to dryness under vacuum. This material was purified by chromatography on a bond-elut (silica, 2 g), eluting with an ethyl acetate/cyclohexane gradient to give after evaporation of the solvent N-cyclopropyl-5-fluoro-4'-[5-(hydroxymethyl)-1,3,4-oxadiazol-2-yl]-6-methyl-1,1'-biphenyl-3-carboxamide.

NMR: δH [$^2$H$_6$]—DMSO 8.55, (1H, d), 8.11(2H, d), 7.65 (4H, m), 5.99(1H, t), 4.75, (2H, d), 2.86, (1H, m), 2.20(3H, d), 0.70(2H, m), 0.57(2H, m). LCMS: MH$^+$ 367, retention time 2.77 minutes.

Example 47

N-Cyclopropyl-6-methyl-4'-[5-(methylamino)-1,3,4-oxadiazol-2-yl]-1,1'-biphenyl-3-carboxamide

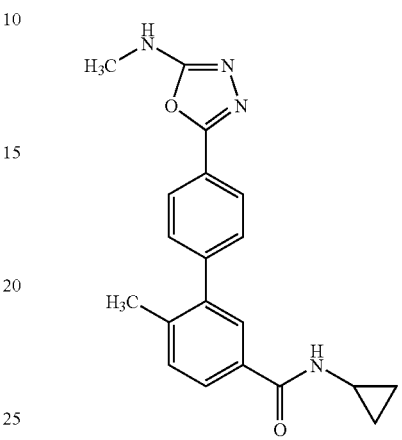

2-(4-Iodophenyl)-5-(methylamino)-1,3,4-oxadiazole (Intermediate 36) (30 mg), N-cyclopropyl-4-methyl-3-(4,4,5,5-tetramethyl-[1,3,2]dioxaborolan-2-yl)-benzamide (33 mg), tetrakis(triphenylphosphine)palladium (13 mg) and aqueous sodium carbonate (1M, 0.11 ml) in DME (3 ml) were mixed and heated at 80° C. for 18 hours. The reaction was purified by HPLC to give N-cyclopropyl-6-methyl-4'-[5-(methylamino)-1,3,4-oxadiazol-2-yl]-1,1'-biphenyl-3-carboxamide.

LCMS: MH$^+$ 349, retention time 2.76 minutes.

Example 48

N-Cyclopropyl-6-methyl-4'-[5-(1-methyl-1H-pyrrol-2-yl)-1,3,4-oxadiazol-2-yl]-1,1'-biphenyl-3-carboxamide

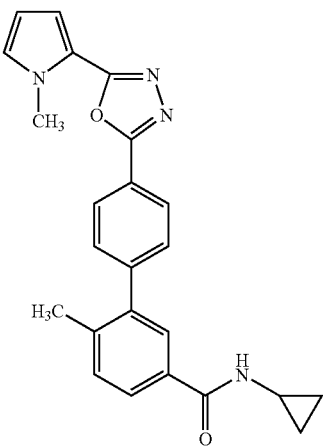

2-(4-Iodophenyl)-5-(1-methyl-1H-pyrrol-2-yl)-1,3,4-oxadiazole (intermediate 38) (35 mg), N-cyclopropyl-4-methyl-3-(4,4,5,5-tetramethyl-[1,3,2]dioxaborolan-2-yl)-benzamide (33 mg), tetrakis(triphenylphosphine)palladium (13 mg) and aqueous sodium carbonate (1M, 0.11 ml) in DME (3 ml) were mixed and heated at 80° C. for 18 hours. The reaction was purified by bond-elut (silica), eluting with an ethyl acetate/cyclohexane gradient to give, after evaporation of the solvent, N-cyclopropyl-6-methyl-4'-[5-(1-methyl-1H-pyrrol-2-yl)-1,3,4-oxadiazol-2-yl]-1,1'-biphenyl-3-carboxamide.

NMR: δH [$^2$H$_6$]—DMSO 8.46, (1H, d), 8.16, (2H, d), 7.79, (1H, dd), 7.75, (1H, d), 7.64, (2H, d), 7.42, (1H, d), 7.21, (1H, m), 7.01, (1H, dd), 6.27, (1H, dd), 4.04, (3H, s), 2.86, (1H, m), 2.31, (3H, s), 0.69, (2H, m), 0.56, (2H, m). LCMS: MH$^+$ 399, retention time 3.41 minutes.

Example 49

N-Cyclopropyl-4'-(5-ethyl-1,3,4-oxadiazol-2-yl)-6-methyl-1,1'-biphenyl-3-carboxeamide

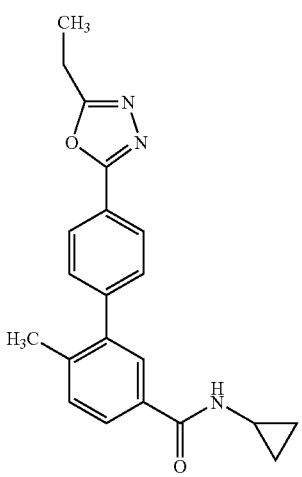

N-Cyclopropyl-4'-(hydrazinocarbonyl)-6-methyl-1,1'-biphenyl-3-carboxamide (Intermediate 40) (50 mg) in triethylorthopropionate (5 ml) was heated at 150° C. for 18 hours. The excess triethylorthopropionate was evaporated under vacuum and the residue purified by bond-elut (silica), eluting with an ethyl acetate/cyclohexane gradient. The solvent was evaporated from the product fractions under vacuum to give N-cyclopropyl-4'-(5-ethyl-1,3,4-oxadiazol-2-yl)-6-methyl-1,1'-biphenyl-3-carboxamide.

NMR: δH [$^2$H$_6$]—DMSO 8.44, (1H, d), 8.08, (2H, d), 7.78, (1H, dd), 7.73, (1H, d), 7.61, (2H, d), 7.42, (1H, d), 2.97, (2H, q), 2.84, (1H, m), 2.30(3H, s), 1.35(3H, t), 0.69, (2H, m), 0.57, (2H, m), LCMS: MH$^+$ 348, retention time 3.04 minutes.

Example 50

N-Cyclopropyl-6-methyl-4'-(1,3,4-oxadiazol-2-yl)-1,1'-biphenyl-3-carboxamide

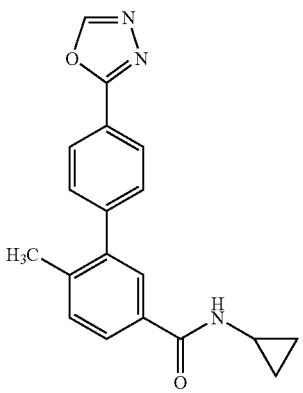

N-Cyclopropyl-4'-(hydrazinocarbonyl)-6-methyl-1,1'-biphenyl-3-carboxamide (Intermediate 40) (50 mg) in triethylorthoformate (5 ml) was heated at 150° C. for 5 hours. The excess triethylorthoformate was evaporated under vacuum and the residue purified by bond-elut (silica), eluting with an ethyl acetate/cyclohexane gradient. The solvent was evaporated from the product fractions under vacuum to give N-cyclopropyl-4'-(1,3,4-oxadiazol-2-yl)-6-methyl-1,1'-biphenyl-3-carboxamide.

NMR: δH [$^2$H$_6$]—DMSO 9.39, (1H, s), 8.45, (1H, d), 8.12, (2H, d), 7.79, (1H, dd), 7.74, (1H, d), 7.64, (2H, d), 7.42, (1H, d), 2.85(1H, m), 2.30(3H, s), 0.69, (2H, m), 0.57, (2H, m). LCMS: MH$^+$ 320, retention time 2.82 minutes.

Example 51

N-Cyclopropyl-5-fluoro-6-methyl-4'-(5-methyl-1,3,4-oxadiazol-2-yl)-1,1'-biphenyl-3-carboxamide

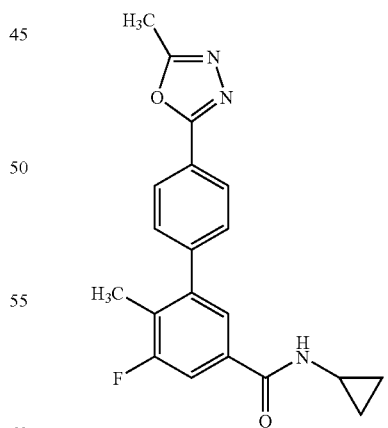

N-Cyclopropyl-5-fluoro-4-methyl-3-(4,4,5,5-tetramethyl-[1,3,2]dioxaborolan-2-yl-benzamide (32 mg), 2-(4-Iodophenyl)-5-methyl-[1,3,4]oxadiazole (29 mg), tetrakis (triphenylphosphine)palladium (2 mg) and aqueous sodiumhydrogen carbonate (0.5 ml) in propan-2-ol (2 ml) were heated at 85° C. for 18 hours. The cooled reaction was diluted with ethyl acetate (6 ml) and applied to a bond-elut (silica, 5 g) and eluted with ethyl acetate. The eluent was reduced to dryness under vacuum, the residue applied to a bond-elut (silica, 1 g) and eluted with ether and then ethyl acetate. The solvent was removed from the ethyl acetate fraction under vacuum to give N-cyclopropyl-5-fluoro-6-methyl-4'-(5-methyl-1,3,4-oxadiazol-2-yl)-1,1'-biphenyl-3-carboxamide.

NMR: δH [²H₆]—DMSO 8.55, (1H, d), 8.08, (2H, d), 7.64, (4H, m), 2.86, (1H, m), 2.61, (3H, s), 2.20, (3H, s), 0.70, (2H, m), 0.57, (2H, m). LCMS: MH⁺ 352, retention time 3.04 minutes.

Example 52

4'-{5-[(Benzoylamino)methyl]-1,3,4-oxadiazol-2-yl}-N-cyclopropyl-6-methyl-1,1'-biphenyl-3-carboxamide

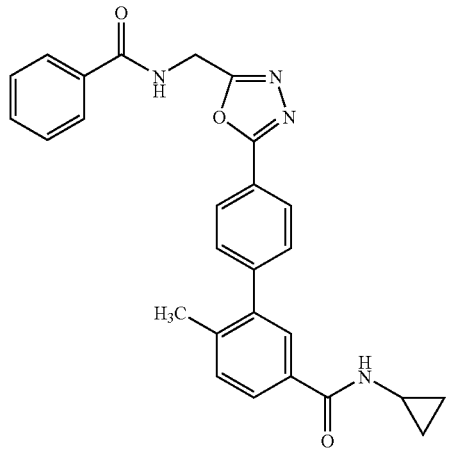

A solution of benzoyl chloride (6.3 μl) in THF (1 ml) was added dropwise to 4'-[5-(aminomethyl)-1,3,4-oxadiazol-2-yl]-N-cyclopropyl-6-methyl-1,1'-biphenyl-3-carboxamide (Example 53) (18.8 mg) and triethylamine (7.5 μl) in THF (4 ml). The reaction was stirred at room temperature for 16 hours, the solvent evaporated, the residue dissolved in water (10 ml) and extracted with DCM (2×10 ml). The combined organics were reduced to dryness under vacuum, the residue dissolved in methanol and the solution applied to a bond-elut (aminopropyl, 1 g), eluting with further methanol. The eluent was reduced to ca 10 ml in vacuo and passed through a bond-elut (SCX, 2 g), eluting with methanol. The solvent was evaporated from the eluent under vacuum. The residue was applied to a bond-elut (silica, 2 g) and eluted with an ethyl acetate/cyclohexane gradient to give, after evaporation of the solvent 4'-{5-[(benzoylamino)methyl]-1,3,4-oxadiazol-2-yl}-N-cyclopropyl-6-methyl-1,1'-biphenyl-3-carboxamide.

NMR: δH MeOD 7.89, (2H, d), 7.69, (2H, d), 7.51, (1H, dd), 7.46, (1H, s), 7.37-7.25, (5H, m), 7.17, (1H, d), 4.69, (2H, s), 2.61, (1H, m), 2.09, (3H, s), 0.57, (2H, m), 0.41, (2H, m), LCMS: MH⁺ 453, retention time 3.05 minutes.

Example 53

4'-[5-(Aminomethyl)-1,3,4-oxadiazol-2-yl]-N-cyclopropyl-6-methyl-1,1'-biphenyl-3-carboxamide

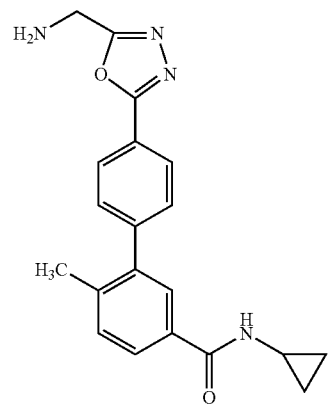

4'-[5-(Azidomethyl)-1,3,4-oxadiazol-2-yl]-N-cyclopropyl-6-methyl-1,1'-biphenyl-3-carboxamide (Intermediate 44) (27.8 mg) and palladium on carbon (10% w/w, 5 mg) in ethanol (5 ml) were hydrogenated under 1 Atm. of hydrogen for 2 hours. The reaction was filtered through celite, the filtrate reduced to dryness under vacuum and the residue applied to a bond-elut (silica, 4 g). The column was eluted with chloroform, ether, ethyl acetate, and methanol. The methanol fraction was reduced to dryness under vacuum to give 4'-[5-(aminomethyl)-1,3,4-oxadiazol-2-yl]-N-cyclopropyl-6-methyl-1,1'-biphenyl-3-carboxamide.

LCMS: MH⁺ 349, retention time 2.16 minutes.

Example 54

N-Cyclopropyl-6-methyl-4'-{[(cyclopropylacetyl)amino]methyl}-1,3,4-oxadiazol-2-yl]-1,1'-biphenyl-3-carboxamide

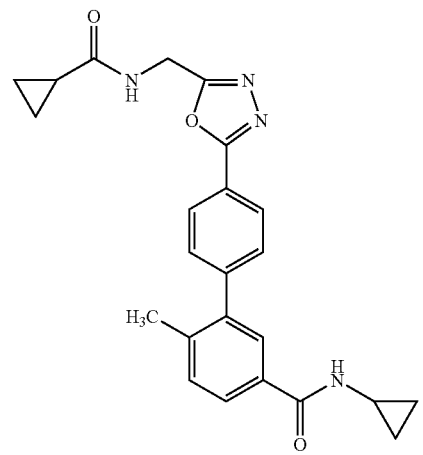

4'-[5-(Aminomethyl)-1,3,4-oxadiazol-2-yl]-N-cyclopropyl-6-methyl-1,1'-biphenyl-3-carboxamide (Example 53)

(30 mg), EDC (19.8 mg), HOBt (11.7 mg), cyclopropylacetic acid (7.4 mg) and DIPEA (0.02 ml) were mixed in DCM (5 ml). The reaction was stirred at room temperature for 48 hours, the reaction was washed with water (2×10 ml) and the DCM was evaporated under vacuum. The residue was dissolved in methanol and filtered through a bond-elut (SCX, 2 g). The solvent was evaporated from the filtrate and the residue applied to a bond-elut (silica) and eluted with an ethyl acetate/cyclohexane gradient to give, after evaporation of the solvent, N-cyclopropyl-6-methyl-4'-{[(cyclopropylacetyl)amino]methyl}-1,3,4-oxadiazol-2-yl]-1,1'-biphenyl-3-carboxamide.

NMR: δH CDCl$_3$ 8.09, (2H, d), 7.66, (1H, dd), 7.61, (1H, d), 7.45, (2H, d), 7.34, (1H, d), 6.45, (1H, bt), 6.27(1H, bs), 4.82(2H, d), 2.91(1H, m), 2.30(3H, s), 1.50, (1H, m), 1.06, (2H, m), 0.86(4H, m), 0.62(2H, m). LCMS: MH$^+$ 417, retention time 2.82 minutes.

Example 55

N-Cyclopropyl-6-methyl-4'-[5-({[(3-methylisoxazol-5-yl)acetyl]amino}methyl)-1,3,4-oxadiazol-2-yl]-1,1'-biphenyl-3-carboxamide

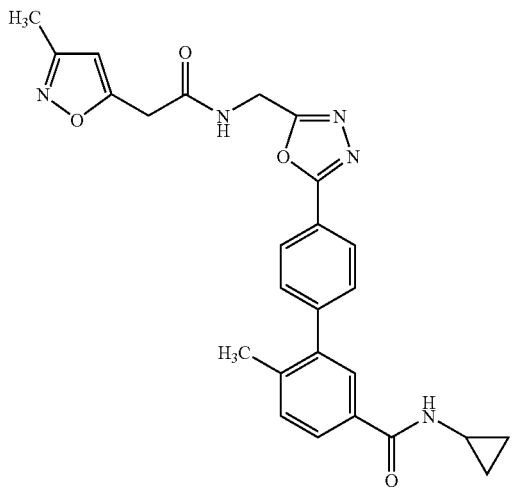

4'-[5-(Aminomethyl)-1,3,4-oxadiazol-2-yl]-N-cyclopropyl-6-methyl-1,1'-biphenyl-3-carboxamide (Example 53) (30 mg), EDC (19.8 mg), HOBt (11.7 mg), 3-methyl-5-isoxazoleacetic acid (12.2 mg) and DIPEA (0.02 ml) were mixed in DMF (5 ml). The reaction was stirred at room temperature for 48 hours, the DMF evaporated under vacuum and the residue dissolved in DCM. The solution was washed with water (2×10 ml) and the DCM was evaporated under vacuum. The residue was dissolved in methanol and filtered through a bond-elut (SCX, 2 g). The solvent was evaporated from the filtrate and the residue applied to a bond-elut (silica) and eluted with an ethyl acetate/cyclohexane gradient to give, after evaporation of the solvent, N-cyclopropyl-6-methyl-4'-[5-({[(3-methylisoxazol-5-yl)acetyl]amino}methyl)-1,3,4-oxadiazol-2-yl]-1,1'-biphenyl-3-carboxamide.

NMR: δH [$^2$H$_6$]—DMSO 9.05, (1H, t), 8.46, (1H, d), 8.06, (2H, d), 7.79, (1H, d), 7.74, (1H, s), 7.63, (2H, d), 7.42, (1H, d), 6.23, (1H, s), 4.66, (2H, d), 2.84, (1H, m), 2.30, (3H, s), 2.19, (3H, s), 0.69(2H, m), 0.57(2H, m). LCMS: MH$^+$ 472, retention time 2.81 minutes.

Example 56

N-Cyclopropyl-4'-{5[-(diethylamino)methyl]-1,3,4-oxadiazol-2-yl}-6-methyl-1,1'-biphenyl-3-carboxamide

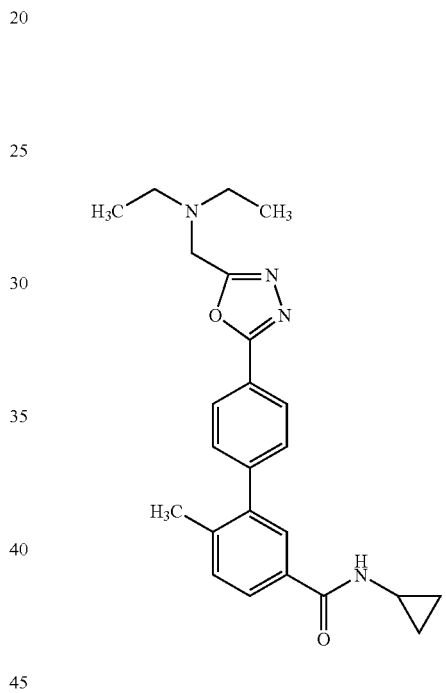

4'-[5-(Chloromethyl)-1,3,4-oxadiazol-2-yl]-N-cyclopropyl-6-methyl-1,1'-biphenyl-3-carboxamide (Intermediate 45) (37 mg) and potassium iodide (5 mg) were mixed in diethylamine (3 ml) and the reaction stirred at room temperature for 18 hours. The excess amine was evaporated under vacuum and the residue purified by bond-elut (silica), eluting with an ethyl acetate/cyclohexane gradient. After evaporation of the solvent this gave N-cyclopropyl-4'-{5-[(diethylamino)methyl]-1,3,4-oxadiazol-2-yl}-6-methyl-1,1'-biphenyl-3-carboxamide.

NMR: δH [$^2$H$_6$]—DMSO 8.46, (1H, d), 8.08, (2H, d), 7.79, (1H, d), 7.73, (1H, s), 7.63, (2H, d), 7.42, (1H, d), 4.00, (2H, s), 2.85, (1H, m), 2.57, (4H, q), 2.30, (3H, s), 1.05, (6H, t), 0.69, (2H, m), 0.57, (2H, m). LCMS: MH$^+$ 405, retention time 2.37 minutes.

Example 57

N-Cyclopropyl-4'-{5-[(cyclopropylamino)methyl]-1,3,4-oxadiazol-2-yl}-6-methyl-1,1'-biphenyl-3-carboxamide

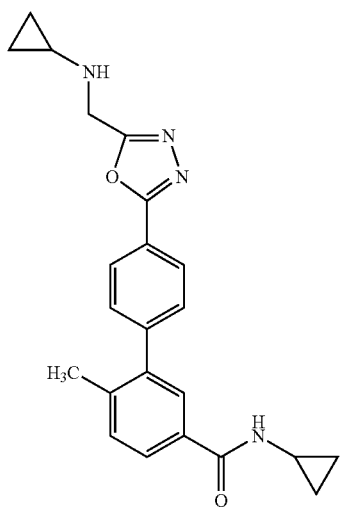

4'-[5-(Chloromethyl)-1,3,4-oxadiazol-2-yl]-N-cyclopropyl-6-methyl-1,1'-biphenyl-3-carboxamide (Intermediate 45) (37 mg) and potassium iodide (5 mg) were mixed in cyclopropylamine (3 ml) and the reaction stirred at room temperature for 18 hours. The excess amine was evaporated under vacuum and the residue purified by bond-elut (silica), eluting with an ethyl acetate/cyclohexane gradient. After evaporation of the solvent this gave N-cyclopropyl-4'-{5-[(cyclopropylamino)methyl]-1,3,4-oxadiazol-2-yl}-6-methyl-1,1'-biphenyl-3-carboxamide.

NMR: δH [$^2$H$_6$]—DMSO 8.46, (1H, d), 8.09, (2H, d), 7.79, (1H, dd), 7.74, (1H, s), 7.63, (2H, d), 7.42, (1H, d), 4.04, (2H, s), 2.85(1H, m), 2.30(3H, s), 2.20, (1H, m), 0.69, (2H, m), 0.57, (2H, m), 0.39, (2H, m), 0.26, (2H, m). LCMS: MH$^+$ 389, retention time 2.53 minutes.

Example 58

N-Cyclopropyl-6-methyl-4'-[5-(thiomorpholin-4-ylmethyl)-1,3,4-oxadiazol-2-yl]-1,1'-biphenyl-3-carboxamide

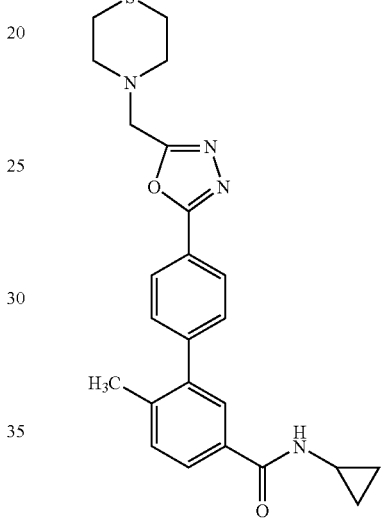

4'-[5-(Chloromethyl)-1,3,4-oxadiazol-2-yl]-N-cyclopropyl-6-methyl-1,1'-biphenyl-3-carboxamide (Intermediate 45) (37 mg) and potassium iodide (5 mg) were mixed in thiomorpholine (2 ml) and DMF (2 ml) and the reaction stirred at room temperature for 18 hours. The solvents were evaporated under vacuum and the residue purified by bond-elut (silica), eluting with an ethyl acetate/cyclohexane gradient. After evaporation of the solvent this gave N-cyclopropyl-6-methyl-4'-[5-(thiomorpholin-4-ylmethyl)-1,3,4-oxadiazol-2-yl]-1,1'-biphenyl-3-carboxamide.

NMR: δH [$^2$H$_6$]—DMSO 8.46, (1H, d), 8.09, (2H, d), 7.78, (1H, d), 7.74, (1H, s), 7.63, (2H, d), 7.42, (1H, d), 3.97, (2H, s), 2.84-2.80, (5H, m), 2.66, (4H, m), 2.30, (3H, s), 0.69, (2H, m), 0.57, (2H, m). LCMS: MH$^+$ 435, retention time 2.96 minutes.

Example 59

4'-{5-[(Cyclohexylamino)methyl]-1,3,4-oxadiazol-2-yl}-N-cyclopropyl-6-methyl-1,1'-biphenyl-3-carboxamide

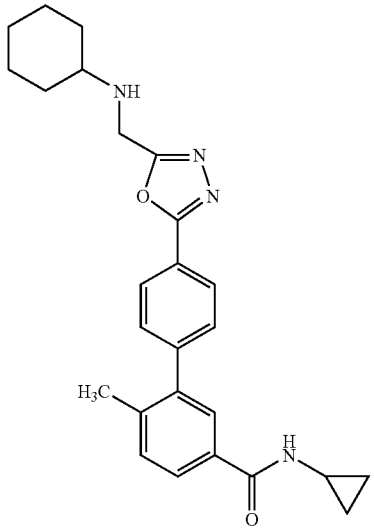

4'-[5-(Chloromethyl)-1,3,4-oxadiazol-2-yl]-N-cyclopropyl-6-methyl-1,1'-biphenyl-3-carboxamide (Intermediate 45) (37 mg) and potassium iodide (5 mg) were mixed in cyclohexylamine (2 ml) and DMF (2 ml) and the reaction stirred at room temperature for 18 hours. The solvents were evaporated under vacuum and the residue purified by bond-elut (silica), eluting with an ethyl acetate/cyclohexane gradient. After evaporation of the solvent this gave 4'-{5-[(cyclohexylamino)methyl]-1,3,4-oxadiazol-2-yl}-N-cyclopropyl-6-methyl-1,1'-biphenyl-3-carboxamide.

NMR: δH [$^2$H$_6$]—DMSO 8.46, (1H, d), 8.14, (1H, s), 8.09, (2H, d), 7.79, (1H, d), 7.74, (1H, s), 7.64, (2H, d), 7.42, (1H, d), 4.17, (2H, s), 2.85, (1H, m), 2.60, (1H, m), 2.30, (3H, s), 1.89, (2H, m), 1.70, (2H, m), 1.56, (1H, m), 1.26-1.05(5H, m), 0.69(2H, m), 0.57, (2H, m).

LCMS: MH$^+$ 432, retention time 2.43 minutes.

Example 60

N-Cyclopropyl-4'-(5-{[(3,3-dimethylbutanoyl)amino]methyl}-1,3,4-oxadiazol-2-yl)-6-methyl-1,1'-biphenyl-3-carboxamide

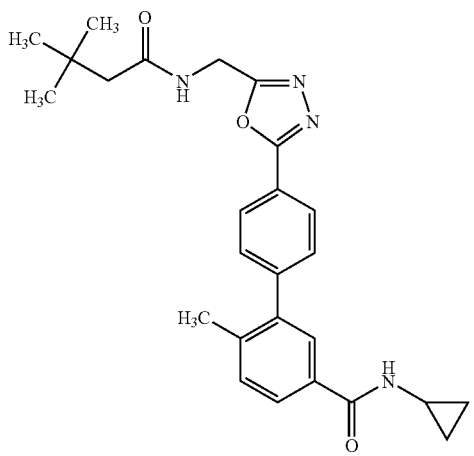

t-Butylacetic acid (10 mg) and HATU (33 mg) in DMF (1 ml) were stirred for 10 minutes at room temperature. To this solution was added HOBt (11.6 mg), DIPEA (0.45 ml) and 4'-[5-(aminomethyl)-1,3,4-oxadiazol-2-yl]-N-cyclopropyl-6-methyl-1,1'-biphenyl-3-carboxamide (Example 53) (30 mg) in DMF (3 ml) and the reaction stirred at room temperature for 72 hours. The solvent was evaporated under vacuum and the residue dissolved in DCM and washed with water (2×5 ml). The organic phase was reduced to dryness and the residue purified by bond-elut (silica, 5 g) eluting with an ethyl acetate/cyclohexane gradient and then by preparative HPLC to give, after evaporation of the solvents, N-cyclopropyl-4'-(5-{[(3,3-dimethylbutanoyl)amino]methyl}-1,3,4-oxadiazol-2-yl)-6-methyl-1,1'-biphenyl-3-carboxamide.

LCMS: MH$^+$ 448, retention time 3.07 minutes.

Example 61

N-Cyclopropyl-4'-{5-[(glycoloylamino)methyl]-1,3,4-oxadiazol-2-yl}-6-methyl-1,1'-biphenyl-3-carboxamide

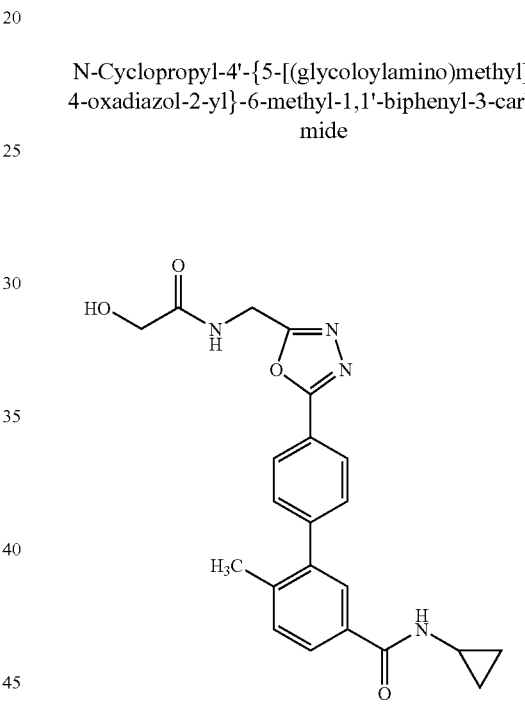

4'-[5-(Aminomethyl)-1,3,4-oxadiazol-2-yl]-N-cyclopropyl-6-methyl-1,1'-biphenyl-3-carboxamide (Example 53) (30 mg), HOBt (11.7 mg), EDC (19.8 mg), DIPEA (0.018 ml) and glycolic acid (6.6 mg) were mixed in DCM (6 ml) and methanol (1 ml) and the reactions stirred at room temperature for 96 hours. The reaction was reduced to dryness under vacuum and the residue partitioned between DCM and water. The organic phase was evaporated and the residue purified by bond-elut (silica, 5 g) eluting with an ethyl acetate/cyclohexane gradient and then by preparative HPLC to give, after evaporation of the solvents, N-cyclopropyl-4'-{5-[(glycoloylamino)methyl]-1,3,4-oxadiazol-2-yl}-6-methyl-1,1'-biphenyl-3-carboxamide.

NMR: δH [$^2$H$_6$]—DMSO 8.60, (1H, t), 8.46, (1H, d), 8.05, (2H, d), 7.79, (1H, dd), 7.74, (1H, d), 7.63, (2H, d), 7.43, (1H, d), 5.67(1H, b), 4.64(2H, d), 3.92, (3H, s), 2.85, (1H, m), 2.30, (3H, s), 0.69, (2H, m), 0.57, (2H, m). LCMS: MH$^+$ 407, retention time 2.56 minutes.

Example 62

4'-(5-{[(Benzylsulfonyl)amino]methyl}-1,3,4-oxadiazol-2-yl)-N-cyclopropyl-6-methyl-1,1'-biphenyl-3-carboxamide

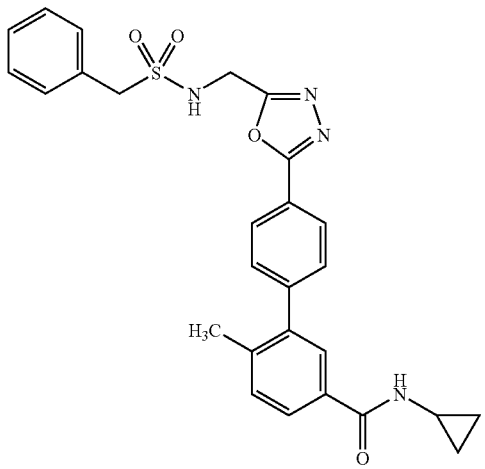

4'-[5-(Aminomethyl)-1,3,4-oxadiazol-2-yl]-N-cyclopropyl-6-methyl-1,1'-biphenyl-3-carboxamide (Example 53) (30 mg) was mixed with α-toluenesulphonyl chloride (33 mg) in pyridine (6 ml) at 0° C. and the reaction stirred at room temperature for 72 hours. Further α-toluenesulphonyl chloride (66 mg) in pyridine (3 ml) was added and stirring continued for 18 hours. The reaction was diluted with DCM and washed with hydrochloric acid (2N, 4×5 ml) and then water (5 ml). The organic phase was reduced to dryness under vacuum and the residue purified by HPLC to give after evaporation of the solvents 4'-(5-{[(benzylsulfonyl)amino]methyl}-1,3,4-oxadiazol-2-yl)-N-cyclopropyl-6-methyl-1,1'-biphenyl-3-carboxamide.

NMR: δH [$^2$H$_6$]—DMSO 8.46, (1H, d), 8.08, (2H, d), 7.79, (1H, dd), 7.74, (1H, d) 7.65, (2H, d), 7.43-7.37, (5H, m), 4.50, (4H, m), 2.85(1H, m), 2.30(3H, s), 0.69, (2H, m), 0.57, (2H, m). LCMS: MH$^+$ 503, retention time 3.11 minutes.

Example 63

N-Cyclopropyl-4'-{5-[(ethylamino)methyl]-1,3,4-oxadiazol-2-yl}-6-methyl-1,1'-biphenyl-3-carboxamide

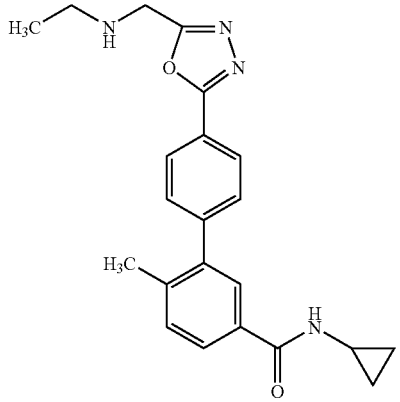

4'-[5-(Chloromethyl)-1,3,4-oxadiazol-2-yl]-N-cyclopropyl-6-methyl-1,1'-biphenyl-3-carboxamide (Intermediate 45) (37 mg) and potassium iodide (5 mg) were mixed in ethylamine in THF (2M, 3 ml) and the reaction stirred at room temperature for 18 hours. The excess amine was evaporated under vacuum and the residue purified by preparative HPLC. After evaporation of the solvent this gave N-cyclopropyl-4'-{5-[(ethylamino)methyl]-1,3,4-oxadiazol-2-yl}-6-methyl-1,1'-biphenyl-3-carboxamide.

NMR: δH [$^2$H$_6$]—DMSO 8.46, (1H, d), 8.18(1H, s), 8.09 (2H, d), 7.79(1H, dd), 7.74, (1H, d), 7.63, (2H, d), 7.42, (1H, d), 4.01(2H, s), 2.85(1H, m), 2.62, (2H, q), 2.30, (3H, s), 1.04, (3H, t), 0.69, (2H, m), 0.57, (2H, m). LCMS: MH$^+$ 377, retention time 2.25 minutes.

Example 64

N-Cyclopropyl-6-methyl-4'-(5-{[(methylsulfonyl)amino]methyl}-1,3,4-oxadiazol-2-yl)-1,1'-biphenyl-3-carboxamide

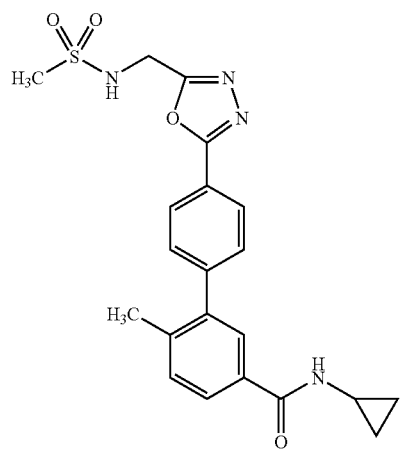

4'-[5-Aminomethyl)-1,3,4-oxadiazol-2-yl]-N-cyclopropyl-6-methyl-1,1'-biphenyl-3-carboxamide (Example 53) (30 mg) was mixed with methanesulphonyl chloride (0.02 ml) and pyridine (0.034 ml) in DCm (3 ml) and the reaction stirred at room temperature for 18 hours. The reaction was washed with water (4×4 ml) and then hydrochloric acid (2N, 5 ml). The organic phase was reduced to dryness under vacuum and the residue purified by HPLC to give after evaporation of the solvents N-cyclopropyl-6-methyl-4'-5-{[(methylsulfonyl)amino]methyl}-1,3,4-oxadiazol-2-yl)-1,1'-biphenyl-3-carboxamide.

NMR: δH [$^2$H$_6$]—DMSO 8.46, (1H, d), 8.09(2H, d), 8.03 (1H, b), 7.79(1H, dd), 7.74, (1H, d), 7.64, (2H, d), 7.42, (1H, d), 4.58(2H, s), 3.05(3H, s), 2.85, (1H, m), 2.30, (3H, s), 0.69(2H, m), 0.57(2H, m). LCMS: MH$^+$ 427, retention time 2.78 minutes.

Example 65

N-Cyclopropyl-6-methyl-4'-{5-[(propionylamino)methyl]-1,3,4-oxadiazol-2-yl}-1,1'-biphenyl-3-carboxamide

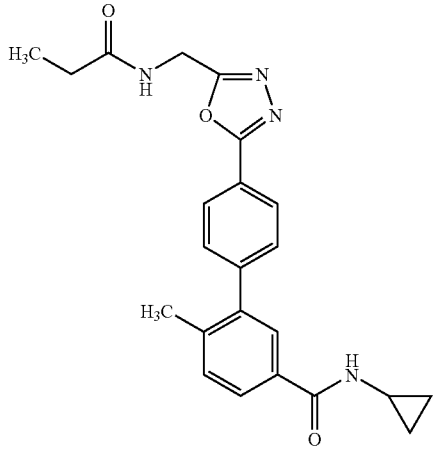

Propionic acid (6.4 mg) and HATU (33 mg) in DMF (1 ml) were stirred for 10 minutes at room temperature. To this solution was added HOBt (11.6 mg), DIPEA (.0.45 ml) and 4'-[5-(aminomethyl)-1,3,4-oxadiazol-2-yl]-N-cyclopropyl-6-methyl-1,1'-biphenyl-3-carboxamide (Example 53) (30 mg) in DMF (2 ml) and the reaction stirred at room temperature for 18 hours. The solvent was evaporated under vacuum and the residue dissolved in DCM and washed with water (2×4 ml). The organic phase was reduced to dryness and the residue purified by bond-elut (SCX, 5 g) eluting with methanol and then by preparative HPLC to give, after evaporation of the solvents, N-cyclopropyl-6-methyl-4'-{5-[(propionylamino)methyl]-1,3,4-oxadiazol-2-yl}-1,1'-biphenyl-3-carboxamide.

NMR: δH [$^2$H$_6$]—DMSO 8.62, (1H, t), 8.46(1H, d), 8.05 (2H, d), 7.79(1H, dd), 7.74, (1H, d), 7.63, (2H, d), 7.42, (1H, d), 4.60(2H, d), 2.85(1H, m), 2.30, (3H, s), 2.20, (2H, q), 1.04, (3H, t), 0.69, (2H, m), 0.57, (2H, m). LCMS: MH$^+$ 405, retention time 2.74 minutes.

Example 66

N-Cyclopropyl-4'-(5-{[(cyclopropylacetyl)amino]methyl}-1,3,4-oxadiazol-2-yl)-6-methyl-1,1'-biphenyl-3-carboxamide

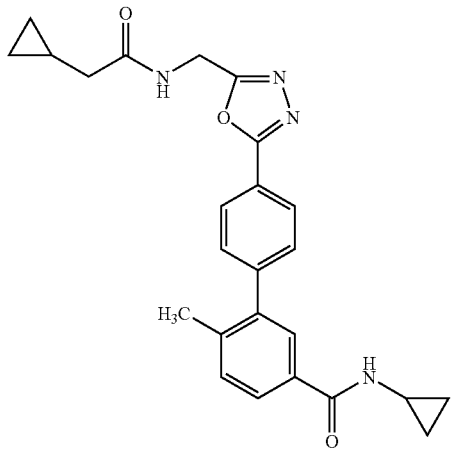

Cyclopropylacetic acid (8.6 mg) and HATU (33 mg) in DMF (1 ml) were stirred for 10 minutes at room temperature. To this solution was added HOBt (11.6 mg), DIPEA (.0.45 ml) and 4'-[5-(aminomethyl)-1,3,4-oxadiazol-2-yl]-N-cyclopropyl-6-methyl-1,1'-biphenyl-3-carboxamide (Example 53) (30 mg) in DMF (2 ml) and the reaction stirred at room temperature for 18 hours. The solvent was evaporated under vacuum and the residue dissolved in DCM and washed with water (2×4 ml). The organic phase was reduced to dryness and the residue purified by bond-elut (SCX, 5 g) eluting with methanol and methanolic ammonia. The methanolic ammonia fraction was further purified by preparative HPLC to give, after evaporation of the solvents, N-cyclopropyl-4'-(5-{[(cyclopropylacetyl)amino]methyl}-1,3,4-oxadiazol-2-yl)-6-methyl-1,1'-biphenyl-3-carboxamide.

NMR: δH [$^2$H$_6$]—DMSO 8.58, (1H, t), 8.45(1H, d), 8.04 (2H, d), 7.77(1H, d), 7.72, (1H, s), 7.62, (2H, d), 7.40, (1H, d), 4.60, (2H, d), 2.84, (1H, m), 2.28, (3H, s), 2.09, (2H, d), 0.98, (1H, m), 0.68, (2H, m), 0.55(2H, m), 0.44(2H, m), 0.15(2H, m). LCMS: MH$^+$431, retention time 2.88 minutes.

Example 67

N-Cyclopropyl-6-methyl-4'-(5-{[(phenylacetyl)amino]methyl}-1,3,4-oxadiazol-2-yl)-1,1'-biphenyl-3-carboxamide

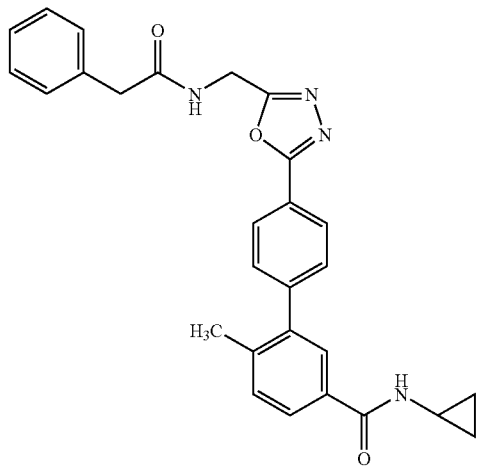

Phenylacetic acid (12 mg) and HATU (33 mg) in DMF (1 ml) were stirred for 10 minutes at room temperature. To this solution was added HOBt (11.6 mg), DIPEA (.0.45 ml) and 4'-[5-(aminomethyl)-1,3,4-oxadiazol-2-yl]-N-cyclopropyl-6-methyl-1,1'-biphenyl-3-carboxamide (Example 53) (30 mg) in DMF (2 ml) and the reaction stirred at room temperature for 18 hours. The solvent was evaporated under vacuum and the residue dissolved in DMSO (0.25 ml), methanol (0.25 ml) was added and the precipitate produced isolated by filtration to give N-cyclopropyl-6-methyl-4'-(5-{[(phenylacetyl)amino]methyl}-1,3,4-oxadiazol-2-yl)-1,1'-biphenyl-3-carboxamide.

NMR: δH [$^2$H$_6$]—DMSO 8.93, (1H, t), 8.46(1H, d), 7.98 (2H, d), 7.79(1H, d), 7.74, (1H, s), 7.62, (2H, d), 7.42, (1H, d), 7.32, (4H, m), 7.25, (1H, m), 4.63, (2H, d), 3.53, (2H, s), 2.85, (1H, m), 2.30, (3H, s), 0.69, (2H, m), 0.57, (2H, m). LCMS: MH$^+$ 467, retention time 3.04 minutes.

Example 68

N-Cyclopropyl-4'-[5-(hydroxymethyl)-1,3,4-oxadiazol-2-yl]-6-methyl-1,1'-biphenyl-3-carboxamide

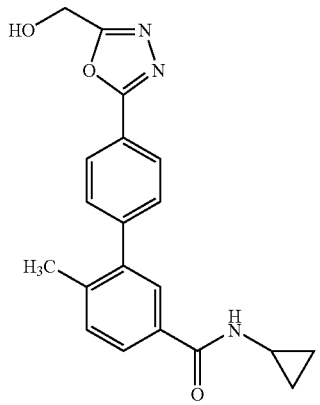

A solution of 4'-[5-(aminomethyl)-1,3,4-oxadiazol-2-yl]-N-cyclopropyl-6-methyl-1,1'-biphenyl-3-carboxamide (Example 53) (30 mg) in acetic acid/water (1:1 v/v, 3 ml) was cooled to 0° C. Sodium nitrite (68 mg) was added and the solution stirred 24 hours at room temperature. Concentrated sodium hydroxide solution was added to the reaction and the mixture extracted with ether (3×20 ml). The combined organic phases were treated with potassium hydroxide in methanol (5%, 3 ml) for 2 hours, washed with water, dried (sodium sulphate) and reduced to dryness under vacuum. The residue was dissolved in 5% potassium hydroxide in methanol and stirred at room temperature for 90 minutes. The methanol was removed in vacuo, the residue partitioned between ethyl acetate/chloroform (1:1)/water and the organic phase dried and reduced to dryness under vacuum. This material was purified by HPLC, to give, after evaporation of the solvent, N-cyclopropyl-4'-[5-(hydroxymethyl)-1,3,4-oxadiazol-2-yl]-6-methyl-1,1'-biphenyl-3-carboxamide.

NMR: δH [$^2$H$_6$]—DMSO 8.46, (1H, d), 8.09, (2H, d), 7.79, (1H, dd), 7.74, (1H, d), 7.64, (2H, d), 7.42, (1H, d), 6.01, (1H, b), 4.75(2H, s), 2.85(1H, m), 2.30, (3H, s), 0.69, (2H, M), 0.57, (2H, m). LCMS: MH$^+$ 350, retention time 2.70 minutes.

Example 69

N-Cyclopropyl-4'-(5-{[(cyclopropylmethyl)amino]methyl}-1,3,4-oxadiazol-2-yl)-6methyl-1,1'-biphenyl-3-carboxamide

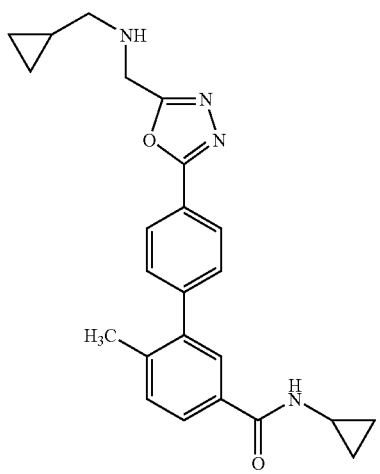

4'-[5-(Chloromethyl)-1,3,4-oxadiazol-2-yl]-N-cyclopropyl-6-methyl-1,1'-biphenyl-3-carboxamide (Intermediate 45) (37 mg) and potassium iodide (5 mg) were mixed in cyclopropylmethylamine (3 ml) and the reaction stirred at room temperature for 18 hours. The excess amine was evaporated under vacuum and the residue purified by preparative HPLC. After evaporation of the solvent this gave N-cyclopropyl-4'-(5-{[(cyclopropylmethyl)amino]methyl}-1,3,4-oxadiazol-2-yl)-6-methyl-1,1'-biphenyl-3-carboxamide.

NMR: δH [$^2$H$_6$]—DMSO 8.46, (1H, d), 8.14(1H, s), 8.09 (2H, d), 7.79(1 H, dd), 7.74, (1H, d), 7.64, (2H, d), 7.42, (1H, d), 4.18(2H, s), 2.85(1H, m), 2.60, (2H, d), 0.93, (1H, m), 0.69, (2H, m), 0.57(2H, m), 0.46(2H, m), 0.18(2H, m). LCMS: MH$^+$ 403, retention time 2.36 minutes.

Example 70

4'-(5-Amino-1,3,4-oxadiazol-2-yl)-N-cyclopropyl-6-methyl-1,1'-biphenyl-3-carboxamide

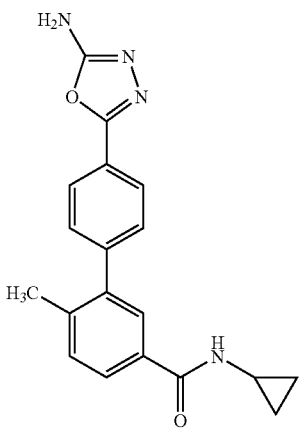

N-Cyclopropyl-4'-(hydrazinocarbonyl)-6-methyl-1,1'-biphenyl-3-carboxamide (Intermediate 40) (35 mg) and a mixture of di(benzotriazolyl)methanimines (30 mg, Synthesis 6, 2001, 897-903) were dissolved in THF (1.5 ml) and the solution heated at reflux for 3 hours. The cooled reaction was absorbed onto silica and applied to a bond-elut (silica, 10 g) and eluted with an ethyl acetate/cyclohexane gradient. The product fractions were combined and evaporated to dryness to give 4'-(5-amino-1,3,4-oxadiazol-2-yl)-N-cyclopropyl-6-methyl-1,1'-biphenyl-3-carboxamide.

NMR: δH [$^2$H$_6$]—DMSO 8.44, (1H, d), 7.88(2H, d), 7.77 (1H, d), 7.72(1H, s), 7.55, (2H, d), 7.40, (1H, d), 7.30, (2H, s), 2.85, (1H, m), 2.30, (3H, s), 0.69, (2H, m), 0.57, (2H, m). LCMS: MH$^+$ 335, retention time 2.71 minutes.

Example 71

N-Cyclopropyl-4'-[5-(ethoxymethyl)-1,3,4-oxadiazol-2-yl]-6-methyl-1,1'-biphenyl-3-carboxamide

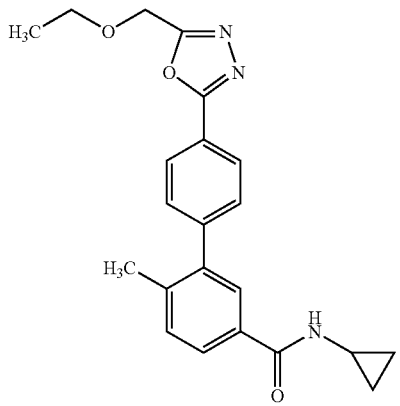

4'-[5-(Chloromethyl)-1,3,4-oxadiazol-2-yl]-N-cyclopropyl-6-methyl-1,1'-biphenyl-3-carboxamide (Intermediate 45) (50 mg) was added to a freshly prepared sodium ethoxide solution (0.087M, 2 ml), and the reaction stirred at room temperature for 72 hours. The reaction was partitioned between ethyl acetate and water, the organic phase dried (sodium sulphate) and reduced to dryness under vacuum. The residue was purified by HPLC to give, after evaporation of the solvent, N-cyclopropyl-4'-[5-(ethoxymethyl)-1,3,4-oxadiazol-2-yl]-6-methyl-1,1'-biphenyl-3-carboxamide.

NMR: δH CDCl$_3$ 8.13, (2H, d), 7.68, (1H, dd), 7.63, (1H, d), 7.46, (2H, d), 7.34, (1H, d), 6.39, (1H, b), 4.78, (2H, s), 3.69, (2H, q), 2.91(1H, m), 2.31(3H, s), 1.29, (3H, t), 0.87, (2H, m), 0.63, (2H, m). LCMS: MH$^+$ 378, retention time 3.09 minutes.

Example 72

N-Cyclopropyl-4'-[5-(cyclopropylmethyl)-1,3,4-oxadiazol-2-yl]-6-methyl-1,1'-biphenyl-3-carboxamide

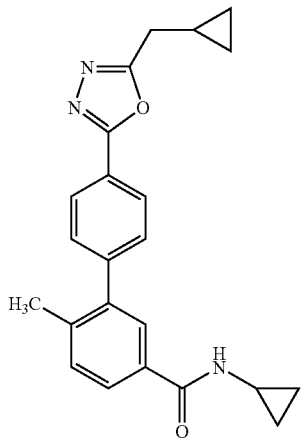

4'-[5-(Azidomethyl)-1,3,4-oxadiazol-2-yl]-N-cyclopropyl-6-methyl-1,1'-biphenyl-3-carboxamide (Intermediate 44) (40 mg), triethylamine (0.051 ml) and ethyl 2-cyclopropylethanimidate hydrochloride (23 mg) in ethanol (3 ml) were heated at 80° C. for 16 hours. The ethanol was removed under vacuum, the residue applied to a bond-elut (silica) and eluted with an ethyl acetate/cyclohexane gradient. Evaporation of the solvent from the product fractions gave N-cyclopropyl-4'-[5-(cyclopropylmethyl)-1,3,4-oxadiazol-2-yl]-6-methyl-1,1'-biphenyl-3-carboxamide.

NMR: δH CDCl$_3$ 8.11, (2H, d), 7.67, (1H, dd), 7.63, (1H, d), 7.46, (2H, d), 7.35, (1H, d), 6.30, (1H, b), 2.94-2.86, (3H, m), 2.31, (3H, s), 1.25(1H, m), 0.88(2H, m), 0.69-0.66, (4H, m), 0.38, (2H, m). LCMS: MH$^+$ 374, retention time 3.25 minutes.

Example 73

N-Cyclopropyl-4'-[5-(methoxymethyl)-1,3,4-oxadiazol-2-yl]-6methyl-1,1'-biphenyl-3-carboxamide

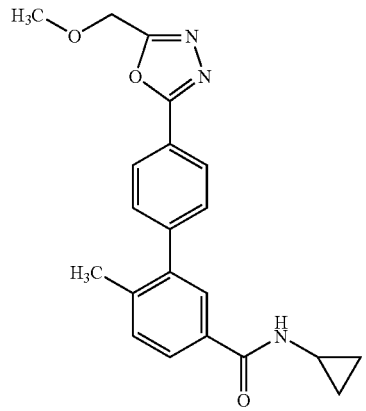

4'-[5-(Chloromethyl)-1,3,4-oxadiazol-2-yl]-N-cyclopropyl-6-methyl-1,1'-biphenyl-3-carboxamide (Intermediate 45) (50 mg) was added to a freshly prepared sodium methoxide solution (0.08M, 12 ml), and the reaction stirred at room temperature for 96 hours. The reaction was partitioned between ethyl acetate and water, the organic phase dried (sodium sulphate) and reduced to dryness under vacuum. The residue was applied to a bond-elut (silica, 5 g) and eluted with an ethyl acetate/cyclohexane gradient. The product fractions were reduced to dryness under vacuum and further purified by HPLC, to give after evaporation of the solvent, N-cyclopropyl-4'-[5-(methoxymethyl)-1,3,4-oxadiazol-2-yl]-6-methyl-1,1'-biphenyl-3-carboxamide.

NMR: δH [$^2$H$_6$]—DMSO 8.46, (1H, d), 8.10, (2H, d), 7.79, (1H, dd), 7.74, (1H, d), 7.63, (2H, d), 7.42, (1H, d), 4.76, (2H, s), 3.41(3H, s), 2.85(1H, m), 2.30, (3H, s), 0.69, (2H, m), 0.56, (2H, m). LCMS: MH$^+$ 364, retention time 2.95 minutes.

Example 74

N-Cyclopropyl-4'-{5-[(cyclopropylmethoxy)methyl]-1,3,4-oxadiazol-2-yl}-6methyl-1,1'-biphenyl-3-carboxamide

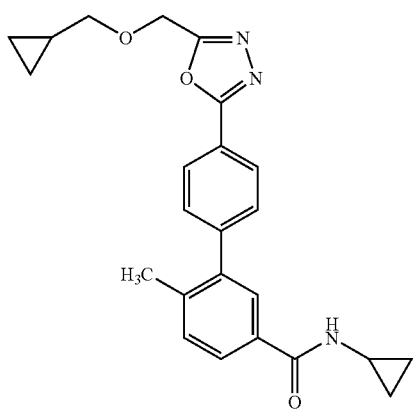

4'-[5-(Chloromethyl)-1,3,4-oxadiazol-2-yl]-N-cyclopropyl-6-methyl-1,1'-biphenyl-3-carboxamide (Intermediate 45) (50 mg) was added to a freshly prepared sodium cyclopropylmethoxide solution (0.08M, 6 ml), and the reaction stirred at room temperature for 26 hours. The reaction was concentrated under vacuum and the residue applied to a bond-elut (silica, 10 g) and eluted with an ethyl acetate/cyclohexane gradient. The product fractions were reduced to dryness under vacuum, to give, N-cyclopropyl-4'-{5-[(cyclopropylmethoxy)methyl]-1,3,4-oxadiazol-2-yl}-6-methyl-1,1'-biphenyl-3-carboxamide.

NMR: δH [$^2$H$_6$]—DMSO 8.45, (1H, d), 8.09, (2H, d), 7.77, (1H, dd), 7.73, (1H, d), 7.62, (2H, d), 7.41, (1H,d), 4.80, (2H, s), 3.41, (2H, d), 2.84(1H, m), 2.29, (3H, s), 1.04, (1H), m), 0.68, (2H, m), 0.56, (2H, m), 0.48, (2H, m), 0.21, (2H, m). LCMS: MH$^+$ 404, retention time 3.24 minutes.

Example 75

N-Cyclopropyl-6-methyl-4'-(5-methyl-1,3,4-triazol-2-yl)-1,1'-biphenyl-3-carboxamide

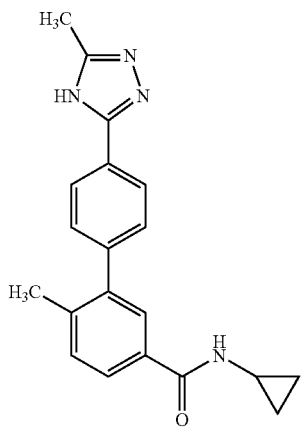

N-Cyclopropyl-4'-[(2-ethanimidoylhydrazino)carbonyl]-6-methyl-1,1'-biphenyl-3-carboxamide (intermediate 46) (80 mg) in xylene (15 ml) was heated at 190° C. under Dean-Stark conditions for 4 hours. The xylene was decanted from the precipitated solid and the solid washed with cyclohexane. The solid was applied to a bond-elut (silica) and eluted with an ethyl acetate/cyclohexane gradient to give, after evaporation of the solvents under vacuum, N-cyclopropyl-6-methyl-4'-(5-methyl-1,3,4-triazol-2-yl)-1,1'-biphenyl-3-carboxamide.

NMR: δH [$^2$H$_6$]—DMSO 13.74, (1H, b), 8.43, (1H, d), 8.05, (2H, d), 7.76-7.72, (2H, m), 7.46, (2H, d), 7.39, (1H, d), 2.85, (1H, m), 2.41(3H, s), 2.30(3H, s), 0.68, (2H, m), 0.56, (2H, m). LCMS: MH$^+$ 333, retention time 2.74 minutes.

Example 76

4'-(4-Acetyl-5-imino-4,5-dihydro-1,3,4-oxadiazol-2-yl)-N-cyclopropyl-6-methyl-1,1'-biphenyl-3-carboxamide

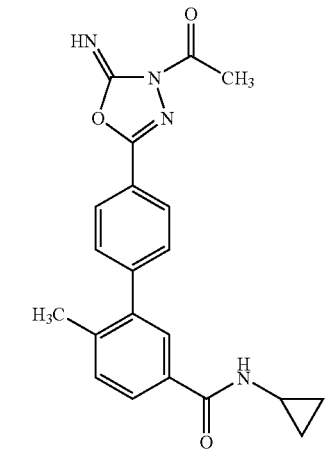

Acetyl chloride (5.1 µl) was added to a solution of 4'-(5-amino-1,3,4-oxadiazol-2-yl)-N-cyclopropyl-6-methyl-1,1'-biphenyl-3-carboxamide (20 mg) and triethylamine (0.01 ml) in THF (2 ml) and the reaction stirred at room temperature for 18 hours. The solvent was evaporated from the reaction and the residue purified by HPLC to give, after evaporation of the solvent, 4'-(4-acetyl-5-imino-4,5-dihydro-1,3,4-oxadiazol-2-yl)-N-cyclopropyl-6-methyl-1,1'-biphenyl-3-carboxamide.

NMR: δH [$^2$H$_6$]—DMSO 8.45, (1H, d), 7.99, (2H, d), 7.78, (1H, d), 7.73, (1H, s), 7.61, (2H, d), 7.42, (1H, d), 2.85, (1H, m), 2.30, (3H, s), 2.16, (3H, s), 0.69, (2H, m), 0.57, (2H, m). LCMS: MH$^+$ 377, retention time 2.65 minutes.

General Method B

Aryl halide (20 mg), {5-[(Cyclopropylamino)carbonyl]-3-fluoro-2-methylphenyl}boronic acid (intermediate 47) (22 mg), tetrakis(triphenylphosphine) palladium (2 mg), sodium-hydrogen carbonate (0.25 ml) and propan-2-ol (1 ml) were mixed in a sealed vessel and heated in a microwave at 150° C. for 10 minutes. Methanol (5 ml) was added, the mixture filtered, and the solvent evaporated in vacuo. The mixture was purified by mass-directed autoprep and the solvents evaporated to give the desired product.

| Compound | Halide | Retention time (Minutes) | MH+ |
|---|---|---|---|
| Example 77 N-Cyclopropyl-5-fluoro-6-methyl-4'-(pyrrol-1-yl)-1,1'-biphenyl-3-carboxamide | 1-(4-iodophenyl)pyrrole | 3.51 | 335 |
| Example 78 4'-(5-Amino-1,3,4-triazol-2-yl)-N-cyclopropyl-5-fluoro-6-methyl-1,1'-biphenyl-3-carboxamide | 2-amino-5-(4-bromophenyl)1,3,4-triazole | 2.66 | 352 |
| Example 79 N-Cyclopropyl-5-fluoro-4'-(imidazol-1-yl)-6-methyl-1,1'-biphenyl-3-carboxamide | 1-(4-bromophenyl)imidazole | 2.36 | 336 |
| Example 80 N-Cyclopropyl-5-fluoro-6-methyl-4'-(tetrazol-5-yl)-1,1'-biphenyl-3-carboxamide | 5-(4-bromophenyl)tetrazole | 3.26 | 338 |
| Example 81 N-Cyclopropyl-5-fluoro-6-methyl-4'-(1-methylpyrazol-3-yl)-1,1'-biphenyl-3-carboxamide | 3-(4-bromophenyl)-1-methylpyrazole | 3.15 | 350 |

Abbreviations
DCM Dichloromethane
DIPEA N,N-Diisopropylethylamine
DME Dimethoxyethane
DMF Dimethylformamide
DMSO Dimethylsulphoxide
EDC 1-(3-Dimethylaminopropyl)-3-ethylcarbodiimide hydrochloride
HATU O-(7-Azabenzotriazol-1-yl)-N,N,N',N'-tetramethyluronium hexafluorophosphate
HOBT 1-Hydroxybenzotriazole hydrate
SPE Solid phase extraction using bond elute cartridges available from Varian
THF Tetrahydrofuran The activity of the compounds of the invention as p38 inhibitors may be demonstrated in the following assays:

p38 Kinase Assay

The peptide substrate used in the p38 assay was biotin-IPTSPITTTYFFFRRR-amide. The p38 and MEK6 proteins were purified to homogeneity from *E. coli* expression systems. The fusion proteins were tagged at the N-terminus with Glutathione-S-Transferase (GST). The maximum activation was achieved by incubating 20 uL of a reaction mixture of 30 nM MEK6 protein and 120 nM p38 protein in the presence of 1.5 uM peptide and 10 mM $Mg(CH_3CO_2)_2$ in 100 mM HEPES, pH 7.5, added to 15 uL of a mixture of 1.5 uM ATP with 0.08 uCi [g-$^{33}$P]ATP, with or without 15 uL of inhibitor in 6% DMSO. The controls were reactions in the presence (negative controls) or absence (positive controls) of 50 mM EDTA. Reactions were allowed to proceed for 60 min at room temperature and quenched with addition of 50 uL of 250 mM EDTA and mixed with 150 uL of Streptavidin SPA beads (Amersham) to 0.5 mg/reaction. The Dynatech Microfluor white U-bottom plates were sealed and the beads were allowed to settle overnight. The plates were counted in a Packard TopCount for 60 seconds. $IC_{50}$ values were obtained by fitting raw data to %I=100*(1−(I-C2)/(C1-C2)), where I was CPM of background, C1 was positive control, and C2 was negative control.

P38 α Fluorescence Polarisation Method

P38 α was prepared in house. SB4777790-R Ligand was diluted in HEPES containing $MgCl_2$, CHAPS, DTT and DMSO. This was added to blank wells of a Black NUNC 384 well plate. P38 α was added to this ligand mixture then added to the remainder of the 384 well plate containing controls and compounds. The plates were read on an LJL Analyst and Fluorescence Anisotropy used to calculate the compound inhibition.

Results

The compounds described in the Examples were tested as described above and had $IC_{50}$ values of <10 μM.

The invention claimed is:
1. A compound of formula (I):

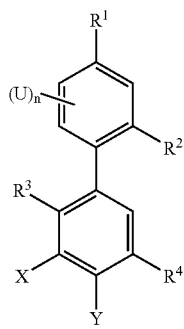

(I)

wherein
R$^1$ is a 5- or 6-membered monocyclic heteroaryl ring containing up to 4 heteroatoms independently selected from oxygen, nitrogen and sulfur, which ring is optionally substituted by up to two substituents selected from $C_{1-6}$alkyl, —(CH$_2$)$_m$—$C_{3-7}$cycloalkyl, halogen, cyano, trifluoromethyl, imino, oxo, —(CH$_2$)$_m$OR$^5$, —(CH$_2$)$_m$COR$^5$, —(CH$_2$)$_m$S(O)$_t$R$^5$, —(CH$_2$)$_m$NR$^5$R$^6$, —(CH$_2$)$_m$CONR$^5$R$^6$, —(CH$_2$)$_m$NHCOR$^5$, —(CH$_2$)$_m$SO$_2$NR$^5$R$^6$, —(CH$_2$)$_m$NHSO$_2$R$^5$, and a 5-membered heteroaryl ring optionally substituted by $C_{1-2}$alkyl;
R$^2$ is selected from hydrogen, methyl, chloro and fluoro;
R$^3$ is selected from methyl and chloro;
R$^4$ is selected from —NH—CO—R$^7$ and —CO—NH—(CH$_2$)$_q$—R$^8$;
R$^5$ is selected from hydrogen, $C_{1-6}$alkyl optionally substituted by up to two OH groups, —(CH$_2$)$_m$—$C_{3-7}$cycloalkyl, —(CH$_2$)$_m$phenyl optionally substituted by R$^{16}$ and —(CH$_2$)$_m$heteroaryl optionally substituted by R$^{16}$,
R$^6$ is selected from hydrogen and $C_{1-6}$alkyl, or
R$^5$ and R$^6$, together with the nitrogen atom to which they are bound, form a 5- or 6-membered heterocyclic ring optionally containing one additional heteroatom independently selected from oxygen, sulfur and N—R$^9$;
R$^7$ is selected from hydrogen, $C_{1-6}$alkyl, —(CH$_2$)$_q$—$C_{3-7}$cycloalkyl, trifluoromethyl, —(CH$_2$)$_r$heteroaryl optionally substituted by R$^{10}$ and/or R$^{11}$, and —(CH$_2$)$_r$phenyl optionally substituted by R$^{10}$ and/or R$^{11}$;
R$^8$ is selected from hydrogen, $C_{1-6}$alkyl, $C_{3-7}$cycloalkyl, CONHR$^{12}$, phenyl optionally substituted by R$^{10}$ and/or R$^{11}$, and heteroaryl optionally substituted by R$^{10}$ and/or R$^{11}$;
R$^9$ is selected from hydrogen and methyl;
R$^{10}$ is selected from $C_{1-6}$alkyl, $C_{1-6}$alkoxy, —(CH$_2$)$_q$—$C_{3-7}$cycloalkyl, —CONR$^{12}$R$^{13}$, —NHCOR$^{13}$, halogen, CN, —(CH$_2$)$_s$NR$^{14}$R$^{15}$, trifluoromethyl, phenyl optionally substituted by one or more R$^{11}$ groups, and heteroaryl optionally substituted by one or more R$^{11}$ groups;
R$^{11}$ is selected from $C_{1-6}$alkyl, $C_{1-6}$alkoxy, halogen, trifluoromethyl, and —(CH$_2$)$_s$NR$^{14}$R$^{15}$;
R$^{12}$ and R$^{13}$ are each independently selected from hydrogen and $C_{1-6}$alkyl, or
R$^{12}$ and R$^{13}$, together with the nitrogen atom to which they are bound, form a 5- or 6-membered heterocyclic ring optionally containing one additional heteroatom independently selected from oxygen, sulfur and N—R$^9$, wherein the ring may be substituted by up to two $C_{1-6}$alkyl groups;
R$^{14}$ is selected from hydrogen, $C_{1-6}$alkyl and —(CH$_2$)$_q$—$C_{3-7}$cycloalkyl optionally substituted by $C_{1-6}$alkyl,
R$^{15}$ is selected from hydrogen and $C_{1-6}$alkyl, or
R$^{14}$ and R$^{15}$, together with the nitrogen atom to which they are bound, form a 5- or 6-membered heterocyclic ring optionally containing one additional heteroatom selected from oxygen, sulfur and N—R$^9$;
R$^{16}$ is selected from halogen, $C_{1-6}$alkyl, hydroxy, $C_{1-6}$alkoxy and trifluoromethyl;
U is selected from methyl and halogen;
X and Y are each selected independently from hydrogen, methyl and halogen;
m is selected from 0, 1, 2 and 3;
n is selected from 0, 1 and 2;
q is selected from 0, 1 and 2;
r is selected from 0 and 1;
s is selected from 0, 1, 2 and 3; and
t is selected from 0, 1 and 2.

2. A compound according to claim 1 wherein R$^1$ is a 5-membered monocyclic heteroaryl ring containing 2, 3 or 4 heteroatoms independently selected from oxygen, nitrogen and sulfur, optionally substituted by up to two substituents selected from $C_{1-4}$alkyl, —(CH$_2$, $_m$—$C_{3-7}$cycloalkyl, imino, —(CH$_2$)$_m$OR$^5$, —(CH$_2$)$_m$COR$^5$, —(CH$_2$)$_m$NR$^5$R$^6$, —(CH$_2$)$_m$NHCOR$^5$, —(CH$_2$)$_m$NHSO$_2$R$^5$ and a 5-membered heteroaryl ring optionally substituted by $C_{1-2}$alkyl.

3. A compound according to claim 1 wherein R$^2$ is hydrogen.

4. A compound according to claim 1 wherein R$^3$ is methyl.

5. A compound according to claim 1 wherein X is fluorine.

6. A compound according to claim 1 wherein R$^7$ is —(CH$_2$)$_r$heteroaryl optionally substituted by R$^{10}$ and/or R$^{11}$.

7. A compound according to claim 1 wherein $R^8$ is selected from $C_{3-6}$cycloalkyl, phenyl optionally substituted by $R^{10}$ and/or $R^{11}$ and heteroaryl optionally substituted by $R^{10}$ and/or $R^{11}$.

8. A pharmaceutical composition comprising an effective amount of a compound according to claim 1 in admixture with one or more pharmaceutically acceptable carriers, diluents or excipients.

9. A process for preparing a compound of formula (I) as claimed claim 1 which comprises reacting a compound of formula (II)

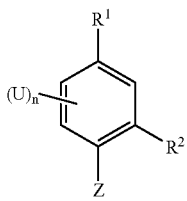

(II)

in which $R^1$, $R^2$, U and n are as defined in claim 1 and Z is halogen, with a compound of formula (III)

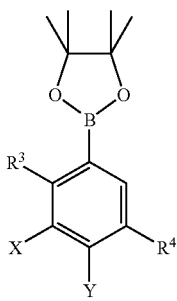

(III)

in which $R^3$, $R^4$, X and Y are as defined in claim 1, in the presence of a catalyst.

10. The compound according to claim 1 wherein $R^4$ is —CO—NH—$(CH_2)_q$—$R^8$.

11. The compound according to claim 10 wherein $R^8$ is a phenyl optionally substituted by $R^{10}$ and/or $R^{11}$.

12. The compound according to claim 11 wherein the $R^{10}$ is $(CH_2)_sNR^{14}R^{15}$.

13. The compound according to claim 12 wherein $R^{14}$ and $R^{15}$ together with the nitrogen atom to which they are bound form a 5- or 6-membered heterocyclic ring optionally further containing one additional oxygen atom.

14. The compound according to claim 2 wherein $R^1$ is an optionally substituted pyrrolyl, thiazolyl, pyrazolyl, imidazolyl, 1,2,4-oxadiazolyl, 1,3,4-oxadiazolyl, 1,3,4-triazolyl or tetrazolyl.

15. The compound according to claim 14 wherein $R^1$ is an optionally substituted thiazolyl.

16. The compound according to claim 15 wherein the thiazolyl is substituted by —$(CH_2)_mNR^5R^6$.

\* \* \* \* \*